(12) United States Patent
Cherif et al.

(10) Patent No.: US 12,230,403 B2
(45) Date of Patent: Feb. 18, 2025

(54) TECHNIQUES FOR DETERMINING ACID-BASE HOMEOSTASIS

(71) Applicant: Fresenius Medical Care Holdings, Inc., Waltham, MA (US)

(72) Inventors: Alhaji Cherif, Kew Gardens, NY (US); Peter Kotanko, New York, NY (US); Doris Helen Fuertinger, Frankfurt am Main (DE)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 815 days.

(21) Appl. No.: 16/815,366

(22) Filed: Mar. 11, 2020

(65) Prior Publication Data

US 2020/0294676 A1  Sep. 17, 2020

Related U.S. Application Data

(60) Provisional application No. 62/816,446, filed on Mar. 11, 2019.

(51) Int. Cl.
| | |
|---|---|
| *G16H 50/50* | (2018.01) |
| *A61M 1/14* | (2006.01) |
| *G16B 5/00* | (2019.01) |
| *G16C 10/00* | (2019.01) |
| *G16C 20/00* | (2019.01) |
| *G16H 10/60* | (2018.01) |
| *G16H 20/10* | (2018.01) |
| *G16H 20/40* | (2018.01) |
| *G16H 20/60* | (2018.01) |
| *G16H 50/20* | (2018.01) |

(52) U.S. Cl.
CPC ............ *G16H 50/50* (2018.01); *G16B 5/00* (2019.02); *G16C 10/00* (2019.02); *G16C 20/00* (2019.02); *G16H 10/60* (2018.01); *G16H 20/10* (2018.01); *G16H 20/40* (2018.01); *G16H 20/60* (2018.01); *G16H 50/20* (2018.01); *A61M 1/14* (2013.01)

(58) Field of Classification Search
None
See application file for complete search history.

(56) References Cited

U.S. PATENT DOCUMENTS

2005/0131663 A1*  6/2005  Bangs .............. G16Z 99/00
703/11

FOREIGN PATENT DOCUMENTS

| EP | 3842084 A1 | 6/2021 |
| WO | 2011130668 A1 | 10/2011 |
| WO | 2020185829 A1 | 9/2020 |

OTHER PUBLICATIONS

Sargent JA. Seminars in Dialysis 31(5): 468-478. (Year: 2018).*
Occhipinti R. "Evidence from mathematical modeling that carbonic anhydrase II and IV enhance CO2 fluxes across Xenopus oocyte plasma membranes." American Journal of Physiology—Cell Physiology. 307: C841-C858. (Year: 2014).*
Ursino M. Prediction of solute kinetics, acid-base status, and blood volume changes during profiled hemodialysis. Annals of Biomedical Engineering 28: 204-216. (Year: 2000).*
International Search Report and Written Opinion for International application No. PCT/US2020/021984, mailed on Aug. 3, 2020, 23 pages.
Constable, Peter D., "Clinical assessment of acid-base status: Comparison of the Henderson-Hasselbalch and strong ion approaches", Veterinary Clinical Pathology 29(4):115-128 (2000).
Goldberg, M., et al., "Computer-Based Instruction and Dagnosis of Acid-Base Disorders: A Systematic Approach", 223(3):269-275 (1973).
Corey, H.E., "Perspectives in Basic Science—Stewart and beyond: New Models of acid-base balance", Kidney International 64:777-787 (2003).
McLaughlin, M.L., "Rational Treatment of Acid-Base Disorders", Drug 39(6):841-855 (1990).
Bushinsky et al., "Arterial PCO2 in Chronic Metabolic Acidosis," Kidney International, vol. 22(3), pp. 311-314 (1982).
Albert et al., "Quantitative Displacement of Acid-Base Equilibrium in Metabolic Acidosis," Annals of Internal Medicine, vol. 66(2), pp. 312-322 (1967) (Abstract).
Maheshwari et al., "An in Silico Method to Predict Net Calcium Transfer During Hemodialysis", 2017 39th Annual International Conference of the IEEE Engineering in Medicine and Biology Society (EMBC), pp. 2740-2743 (2017) (Abstract).
Sargent et al., "Acid-Base Homeostasis During Hemodialysis: New Insights Into the Mystery of Bicarbonate Disappearance During Treatment" Seminars in Dialysis, pp. 1-11, 2018 (Abstract).
Sargent et al., "Changing Dialysate Composition to Optimize Acid-Base Therapy", Seminars in Dialysis, 32(3):248-254, 2019 (Abstract).
Morel et al., "A Comparison of Bicarbonate Kinetics and Acid-Base Status in High Flux Hemodialysis and Online Post-Dilution Hemodiafiltration", International Journal of Artificial Organs, vol. 35(4):288-300, 2012 (Abstract).
Annan, "Mathematical Modeling of the Dynamic Exchange of Solutes During Bicarbonate Dialysis", Mathematical and Computer Modelling, vol. 55(5-6):1691-1704, 2012.

(Continued)

*Primary Examiner* — Olivia M. Wise
*Assistant Examiner* — Robert J. Kallal
(74) *Attorney, Agent, or Firm* — KDW Firm PLLC

(57) ABSTRACT

The described technology may include processes to model acid-base homeostasis in normal patients and under acid-base disorder conditions. In one embodiment, a method may include an acid-base homeostasis analysis. The method may include, via a processor of a computing device: providing a physiological acid-base model configured to model acid-base homeostasis of a virtual patient, the physiological acid-base model to: determine a plurality of operating parameters for an $HCO_3/CO_2$ buffering system having renal and pulmonary regulatory mechanisms, determine acid-base information comprising a bicarbonate concentration, a carbon dioxide concentration, and a free hydrogen ions concentration via simulating the $HCO_3/CO_2$ buffering system, and determine predicted patient information based on the acid-base information. Other embodiments are described.

15 Claims, 34 Drawing Sheets

(56) References Cited

OTHER PUBLICATIONS

Atkinson et al., "pH Sensors and Ion Transporters: Potential Therapeutic Targets for Acid-Base Disorders", International Journal of Pharma Research & Review, vol. 5(3):51-58, 2016.
Batzel et al., "Cardiovascular and Respiratory Systems: Modeling, Analysis, and Control", SIAM, Philadelphia, PA, vol. 34, 2007 (Abstract).
Blower et al. "Sensitivity and Uncertainty Analysis of Complex Models of Disease Transmission: an HIV Model, as an Example", Int. Stat. Rev., 62(2):229-243, 1994 (Abstract).
Boron, Walter F., "Acid-Base Transport by the Renal Proximal Tubule", Journal of the American Society of Nephrology, 17(9):2368-2382, 2006 (Abstract).
Busa, W.B., et al., "Metabolic Regulation Via Intracellular pH", American Journal of Physiology, vol. 246:R409-R438,1984.
Widdicombe, J. & Davies, A., "Respiratory Physiology", 1st edition, Edward Arnold Publishers, 79:102, 1983 (Abstract).
Bushinsky et al., "Randomized, Controlled Trial of TRC101 to Increase Serum Bicarbonate in Patients with CKD", Clinical Journal of the American Society of Nephrology, 13(1), pp. 26-35, 2018.
Chegwidden et al., "The Carbonic Anhydrases: New Horizons", Birkhauser Press, 2000 (Abstract).
Coli et al., "Evaluation of Intradialytic Solute and Fluid Kinetics", Blood Purification, 18(1):37-49, 2000 (Abstract).
Dash et al., "Simultaneous Blood-Tissue Exchange of Oxygen, Carbon Dioxide, Bicarbonate, and Hydrogen Ion", Annals of Biomedical Engineering, 34(7):1129-1148, 2006 (Abstract).
Davenport, "The ABC of Acid-Base Chemistry: The Elements of Physiological Blood-Gas Chemistry for Medical Students & Physicians", The University of Chicago, Chicago, IL, 1974 (Abstract).
DeCoursey, "The Intimate and Controversial Relationship Between Voltage-Gated Proton Channels and the Phagocyte NADPH Oxidase", Immunol Rev., 273(1):194-218, 2016 (Abstract).
Engel et al., "Quantitative Displacement of Acid-Base Equilibrium in Chronic Respiratory Acidosis", Journal of Applied Physiology, 24(3):288-295, 1968.
Fencl et al., "Respiration and Cerebral Blood Flow in Metabolic Acidosis and Alkalosis in Humans", Journal of Applied Physiology, 27(1):67-76, 1969.
Gonzalez et al., "Secondary Response to Chronic Respiratory Acidosis in Humans: A Prospective Study", Kidney International Reports, 3(5): 1163-1170, 2018.
Hainsworth, R. ed., "Acid-Base Balance", Manchester University, UK, 1986 (Abstract).
Hamm et al., "Acid-Base Homeostasis", Clinical Journal of the American Society of Nephrology, 10(12):2232-2242, 2015.
Hoffmann, E.K, and Simonsen, L.O., "Membrane Mechanisms in Volume and pH Regulation in Vertebrate Cells", Physiol Rev., 69(2):315-382, 1989 (Abstract).
Javaheri et al., "Compensatory Hypoventilation in Metabolic Alkalosis", Chest. 81(3):296-301, 1982.

Lang, W., et al., "Prediction of Dilutional Acidosis Based on the Revised Classical Dilution Concept for Bicarbonate", Journal of Applied Physiology, 98(1), 62-71, 2005.
Marino, S., et al., "A Methodology for Performing Global Uncertainty and Sensitivity Analysis in Systems Biology", Journal of Theoretical Biology, 254(1), pp. 178-196, 2008.
Martin et al., "A Mathematical Model of Tumour and Blood pHe Regulation: The HCO3-/CO2 Buffering System", Mathematical Biosciences, 230(1), 1-11, 2011 (Abstract).
Masco, "Acid-Base Homeostasis", Journal of Infusion Nursing, 39(5), pp. 288-295, 2016.
Mitchell et al., "Respiration and Cerebrospinal Fluid pH in Metabolic Acidosis and Alkalosis", Journal of Applied Physiology, 20:905-911, 1965.
Nagami et al., "Regulation of Acid-Base Balance in Chronic Kidney Disease", Advances in Chronic Kidney Disease, 24 (5):274-279, 2017 (Abstract).
Quigley, Raymond "Acid-Base Homeostasis", Clinical Pediatric Nephrology, p. 235, 2016.
Roberts et al., "Evaluation of Respiratory Compensation in Metabolic Alkalosis", Journal of Clinical Investigation, 35(2):261-6, 1956.
Wolf et al., "A Mathematical Model of Blood-Interstitial Acid-Base Balance: Application to Dilution Acidosis and Acid-Base Status", Journal of applied physiology, 110(4):988-1002, 2011.
Schonichen et al., "Considering Protonation as a Posttranslational Modification Regulating Protein Structure and Function", Annual Reviews of Biophysics, 42:289-314, 2013.
Schwartz et al., "The Nature of the Renal Response to Chronic Disorders of Acid-Base Equilibrium", The American Journal of Medicine, 64(3):417-428, 1978 (Abstract).
Skelton et al., "Acid-Base Transport by the Renal Proximal Tubule", Journal of Nephrology, 23(0 16):S4-18, 2010.
Thews et al., "A Comprehensive Model of the Dynamic Exchange Process During Hemodialysis", Medical Progress Through Technology, 16(3), 145-161, 1990 (Abstract).
Ursino et al., "Prediction of Solute Kinetics, Acid-Base Status, and Blood Volume Changes During Profiled Hemodialysis", Annals of Biomedical Engineering, 28(2):204-216 (2000) Abstract.
"Vander's Renal Physiology", Eaton, D., & Pooler, J, editors, 7th edition McGraw-Hill Medical (2009).
Ward et al., "The Respiratory System at a Glance, Third Edition". John Wiley & Sons, Ltd, Publications (UK: Wiley-Blackwell) , 2010 (Abstract).
West, John B., "Respiratory Physiology. 9th Edition", Lippincott Williams and Wilkins, Philadelphia, PA, 2012 (Abstract).
Habran et al., "Importance of Metabolism Variations in a Model of Extracorporeal Carbon Dioxide Removal" 2016 • In Conference Proceedings: Annual International Conference of the IEEE Engineering in Medicine and Biology Society, 4 pages.
International Search Report and Written Opinion for International application No. PCT/US2023/023340, mailed on Sep. 8, 2023, 19 pages.
Forster et al., "Low-flow CO2 removal integrated into a renal-replacement circuit can reduce acidosis and decrease vasopressor requirements," Crit Care 17, R154 (2013), 11 pages.

* cited by examiner

302
VENTILATION FUNCTION

| FUNCTION TYPE | pO$_2$ VALUES | V$_0$ | V$_p$ | I$_p$ | R$^2$ | R$^2_{ADJ}$ | SC (BIC) | AIC |
|---|---|---|---|---|---|---|---|---|
| V$_1$ | 37 | 18.917 | 50.063 | 29.969 | 0.851 | 0.846 | 434.372 | 428.089 |
|  | 47 | 12.288 | 34.757 | 31.702 | 0.984 | 0.98 | 289.909 | 283.432 |
|  | 110 | -3.434 | 513.675 | 29.940 | 0.987 | 0.986 | 187.336 | 181.786 |
|  | 169 | 10.352 | 9898.529 | 36.475 | 0.983 | 0.982 | 171.025 | 165.812 |
| V$_2$ | 37 | 18.912 | 0.196 | 29.969 | 0.851 | 0.846 | 434.372 | 428.089 |
|  | 47 | 12.288 | 0.131 | 31.702 | 0.984 | 0.983 | 289.909 | 283.432 |
|  | 110 | 9.478 | 0.6266 | 36.155 | 0.987 | 0.987 | 186.108 | 180.557 |
|  | 169 | 9.934 | 0.863 | 36.266 | 0.983 | 0.982 | 171.069 | 165.856 |
| UNITS | mmHg | L/MIN | L$^2$/MOL x MIN | mmHg | ... | ... | ... | ... |

BICARBONATE BUFFER KINETIC SYSTEM

| DESCRIPTION | SYMBOLS | VALUES (RANGE) | UNITS | REFS. |
|---|---|---|---|---|
| PARAMETERS | | | | |
| HYDRATION REACTION RATE | $K_{H^+,HCO_3^-}$ | $3.437\ (1.72,\ 6.87) \times 10^{10}$ | L/mol/s | CALCULATED |
| DEHYDRATION REACTION RATE | $K_{CO_2}$ | $2.73\ (1.37,\ 5.46) \times 10^4$ | $s^{-1}$ | [18] |
| PRODUCTION OF HYDROGEN ION | $P_{H^+}$ | $1.2\ (0.6,\ 2.4) \times 10^{-6}$ | mol/L/s | [18] |
| BICARBONATE SUPPLEMENTATION/THERAPY | $J_{HCO_3^-}$ | $0\ (-1.2,\ 1.2 \times 10^{-6})$ | mol/L/s | ASSUMED, [18,13] |
| PRODUCTION OF CARBON DIOXIDE | $P_{CO_2}$ | $3\ (1.5,\ 6) \times 10^{-6}$ | mol/L/s | [18,13] |
| ACID SECRETION RATE | $\Phi_{CO_2}$ | $7.1\ (3.55,\ 14.2) \times 10^{-3}$ | $s^{-1}$ | CALCULATED |
| RENAL FILTRATION RATE | $D_{HCO_3^-}$ | $3.5461\ (1.77,\ 7.09) \times 10^{-4}$ | $s^{-1}$ | [13] |
| VENTILATION RATE | $D_{CO_2}$ | $2.5\ (1.25,\ 5) \times 10^{-2}$ | $L^{-1}$ | [18,13] |
| REMOVAL OF $H^+$ | $\gamma_{H^+}$ | $30.151\ (15.08,\ 60.30)$ | $s^{-1}$ | CALCULATED |
| INITIAL CONDITIONS | | | | |
| HYDROGEN ION CONCENTRATION ($H^+$) | $Y_{H^+}^0$ | $3.98 \times 10^{-8}$ | mol/L | [13] |
| BICARBONATE ION CONCENTRATION ($HCO_3^-$) | $Y_{HCO_3^-}^0$ | $2.4 \times 10^{-2}$ | mol/L | [13] |
| CARBON DIOXIDE CONCENTRATION ($CO_2$) | $Y_{CO_2}^0$ | $1.2 \times 10^{-3}$ | mol/L | [13] |
| MINUTE VENTILATION | $v_0$ | 0.10 | L/s | [45] |

FIG. 4

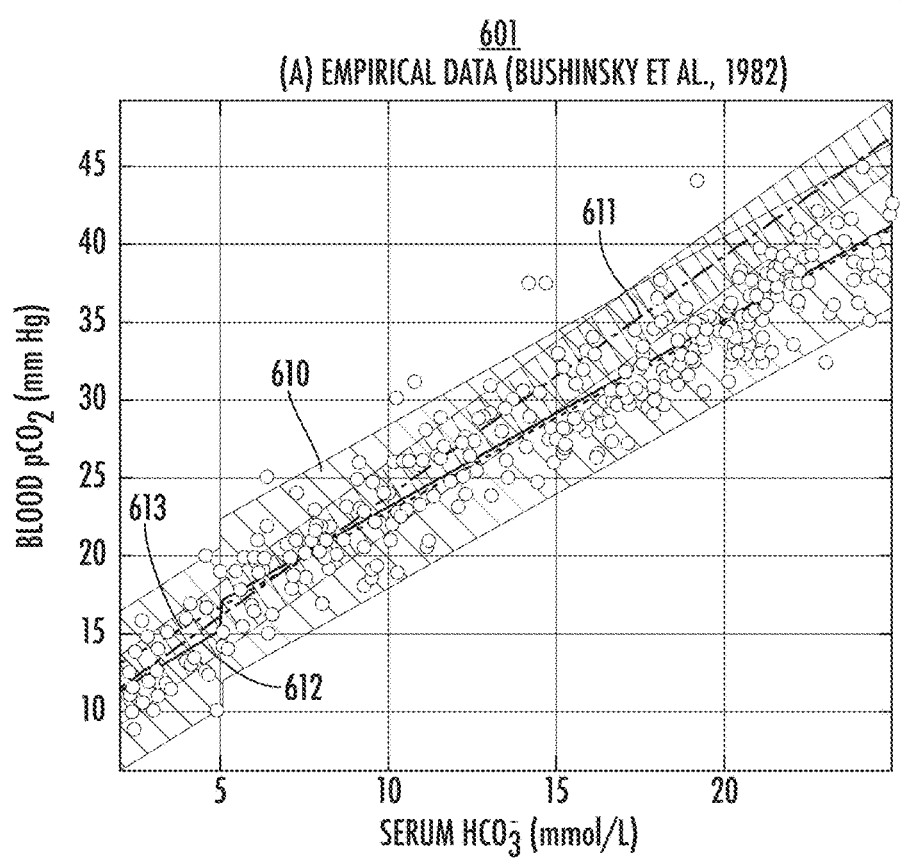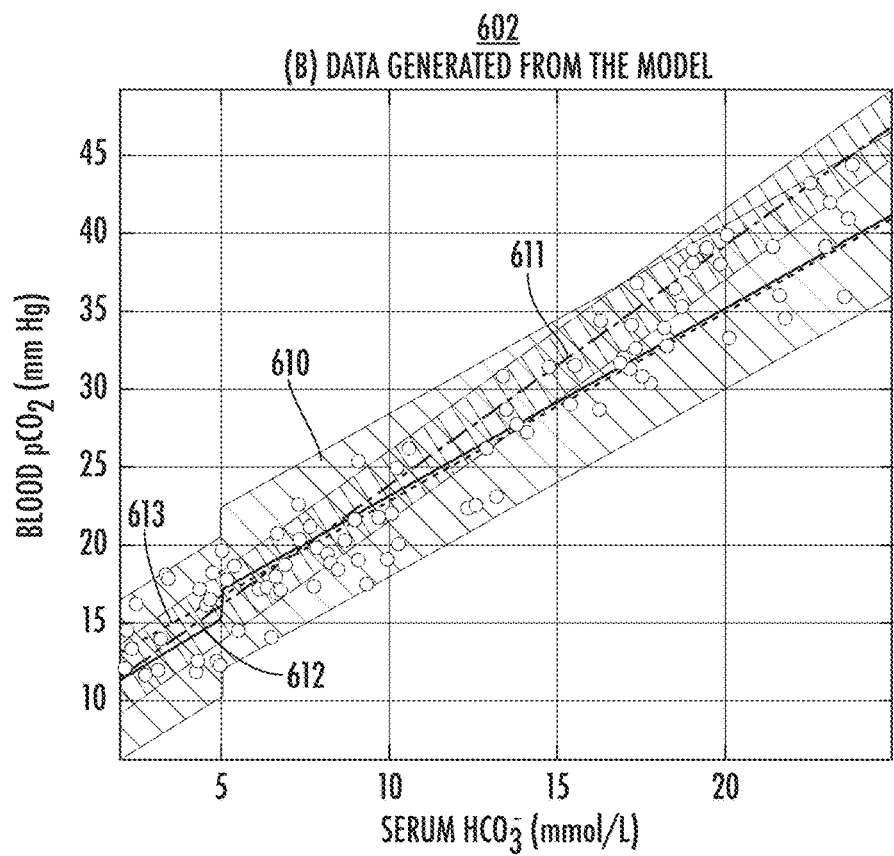
FIG. 6A

| 702 |
| --- |
| SECONDARY COMPENSATORY RESPONSES |

| TYPES | Y | INTERCEPT (B) | SLOPE (M) | X | REFS. |
| --- | --- | --- | --- | --- | --- |
| METABOLIC DISORDERS | | | | | |
| ACIDOSIS | $pCO_2$ | 1.2152 | 10.6494 | $HCO_3^-$ | [1, 8] |
| ALKALOSIS | $pCO_2$ | 20 | 0.7 | $HCO_3^-$ | [23, 20] |
| RESPIRATORY DISORDERS | | | | | |
| ACIDOSIS (CHRONIC) | $HCO_3^-$ | 4.7364 | 0.4760 | $pCO_2$ | [15] |
| ALKALOSIS (CHRONIC) | $HCO_3^-$ | 4.0 | 0.5 | $pCO_2$ | [35] |

FIG. 7

| PARAMETERS | PRCC | | | | | | | |
|---|---|---|---|---|---|---|---|---|
| | HCO₃⁻ | CO₂ | H⁺ | pH | HCO₃⁻ | CO₂ | H⁺ | pH |
| | HEALTHY | | | | COMPLETE RENAL INSUFFICIENCY | | | |
| $P_H$ | 0.3199 | 0.5679 | 0.4186 | -0.4186 | -0.4326 | 0.3910 | 0.7628 | -0.7628 |
| $\gamma_H$ | -0.4630 | -0.6930 | -0.5311 | 0.5311 | 0.6998 | -0.6543 | -0.9292 | 0.9292 |
| $K_{HHCO_3}$ | 0.5190 | 0.7245 | 0.8273 | 0.8273 | -0.6825 | 0.6990 | 0.6320 | 0.6320 |
| $K_{CO_2}$ | -0.4762 | -0.7002 | -0.8358 | -0.8358 | 0.6945 | -0.6702 | -0.6360 | -0.6360 |
| $P_{HCO_3}$ | 0.5935 | 0.3460 | -0.3820 | 0.3820 | 0.8562 | 0.6607 | -0.6768 | 0.6768 |
| $D_{HCO_3}$ | -0.7407 | 0.3999 | 0.5633 | -0.5633 | -- | -- | -- | -- |
| $\Phi_{CO_2}$ | 0.8909 | 0.6333 | -0.7601 | 0.7601 | -- | -- | -- | -- |
| $P_{CO_2}$ | 0.9157 | 0.9161 | 0.1127** | -0.1127** | 0.9030 | 0.9533 | 0.7415 | -0.7415 |
| $D_{CO_2}$ | -0.7728 | -0.8297 | -0.2714 | 0.2715 | -0.6515 | -0.8345 | -0.6390 | 0.6390 |
| | dRTA OR RTA I | | | | pRTA OR RTA II | | | |
| $P_H$ | -0.2916 | 0.3864 | 0.7675 | -0.7675 | 0.3086 | 0.5811 | 0.3373 | -0.3373 |
| $\gamma_H$ | 0.6376 | -0.7442 | -0.9518 | 0.9518 | -0.4972 | -0.6316 | -0.1611 | 0.1611 |
| $K_{HHCO_3}$ | -0.6260 | 0.7546 | -0.6009 | 0.6009 | 0.4013 | 0.5949 | -0.8707 | 0.8707 |
| $K_{CO_2}$ | 0.6572 | -0.7288 | 0.5992 | -0.5992 | -0.4566 | -0.6256 | 0.8828 | -0.8828 |
| $P_{HCO_3}$ | 0.8546 | 0.7110 | -0.5625 | 0.5625 | 0.5889 | 0.2830 | -0.4806 | 0.4806 |
| $D_{HCO_3}$ | -0.7470 | -0.5817 | 0.4915 | -0.4915 | -- | -- | -- | -- |
| $\Phi_{CO_2}$ | -- | -- | -- | -- | 0.8886 | 0.4728 | -0.8224 | 0.8224 |
| $P_{CO_2}$ | 0.9130 | 0.9528 | 0.8516 | -0.8516 | 0.9143 | 0.9196 | -0.1126* | 0.1126* |
| $D_{CO_2}$ | -0.5897 | -0.7536 | -0.5804 | 0.5804 | -0.7729 | -0.8902 | -0.4156 | 0.4156 |

FIG. 8

TABLE 1: MODEL VARIABLES AND PARAMETERS

| SYMBOL | DESCRIPTION | UNITS | VALUE |
|---|---|---|---|
| $C_{H^+}$ | CONCENTRATION OF $H^+$ IN THE PATIENT | M | - |
| $C_{HCO_3^-}$ | CONCENTRATION OF $HCO_3^-$ IN THE PATIENT | M | - |
| $C_{CO_2}$ | CONCENTRATION OF $CO_2$ IN THE PATIENT | M | - |
| $V_{EX}$ | EXTRACELLULAR VOLUME | L | - |
| $c_{HCO_3^-}$ | CONCENTRATION OF DIALYZER $HCO_3^-$ IN THE BLOOD SIDE | M | - |
| $c_{D,HCO_3^-}$ | CONCENTRATION OF DIALYZER $HCO_3^-$ IN THE DIALYSATE SIDE | M | 32 OR 38 |
| $c_{HCO_3^-, OUT}$ | CONCENTRATION OF $HCO_3^-$ AT DIALYZER EXIT | M | - |
| $P_{H^+}$ | ENDOGENOUS PRODUCTION OF $H^+$ | mol·MIN$^{-1}$ | ESTIMATED |
| $P_{CO_2}$ | ENDOGENUOS PRODUCTION OF $CO_2$ | mol·MIN$^{-1}$ | ESTIMATED |
| $\gamma_{H^+}$ | NON-BICARBONATE REMOVAL OR MOBILIZATION OF $H^+$ | L·MIN$^{-1}$ | ESTIMATED |
| $D_{CO_2}, V_0$ | RESPIRATORY RATE | L·MIN$^{-1}$ | ESTIMATED |
| $K_{H^+, HCO_3^-}$ | HYDRATION REACTION/ASSOCIATION RATE | M$^{-1}$ MIN$^{-1}$ | $2.06 \times 10^{11}$ |
| $K_{CO_2}$ | DEHYDRATION REACTION/DISSOCIATION RATE | MIN$^{-1}$ | $1.64 \times 10^5$ |
| A | BLOOD FLOW AREA OF FIBER (INNER CROSS-SECTIONAL AREA OF FIBER) | m$^2$ | $3.46 \times 10^{-8}$ |
| $A_d$ | EFFECTIVE FLOW AREA FOR DIALYSTATE AROUND A FIBER (ANNULUS SPACE BETWEEN FIBERS) | m$^2$ | $4.06 \times 10^{-8}$ |
| $K_0A$ | DIALYZER AREA MASS-TRANSFER COEFFICIENT | mL·MIN$^{-1}$ | 800 |
| L | LENGTH OF FIBER | m | 0.23 |
| N | NUMBER OF FIBERS IN DIALYZER HOUSING | - | 12,300 |
| Pe | PÉCLET NUMBER | - | 0.011+0.004* |
| $Q_p$ | BLOOD FLOW RATE | mL·MIN$^{-1}$ | - |
| $Q_d$ | DIALYSATE FLOW RATE | mL·MIN$^{-1}$ | - |
| $\beta$ | GIBBS-DONNAN CORRECTION FACTOR | - | 1.05 |
| $Q_{pi}$ | BLOOD FLOW RATE (BASELINE) | mL·MIN$^{-1}$ | 350 or 400 |
| $Q_{di}$ | DIALYSATE FLOW RATE (BASELINE) | mL·MIN$^{-1}$ | 500 |
| $Q_{uf}$ | ULTRAFILTRATION RATE ACROSS THE DIALYZER | mL·MIN$^{-1}$ | -** |
| $\sigma_{c_{HCO_3^-}}$ | REFLECTION COEFFICIENT OF CONCENTRATION SPECIES IN THE SERUM | - | 0.999 OR 0 |
| $TIME_{dia}$ | DIALYSIS SESSION DURATION | MIN | 209-240 |

**NOMENCLATURE WITH DESCRIPTION OF SYMBOLS, CORRESPONDING UNITS AND VALUES.
*CALCULATED FOR EACH PATIENT

FIG. 11

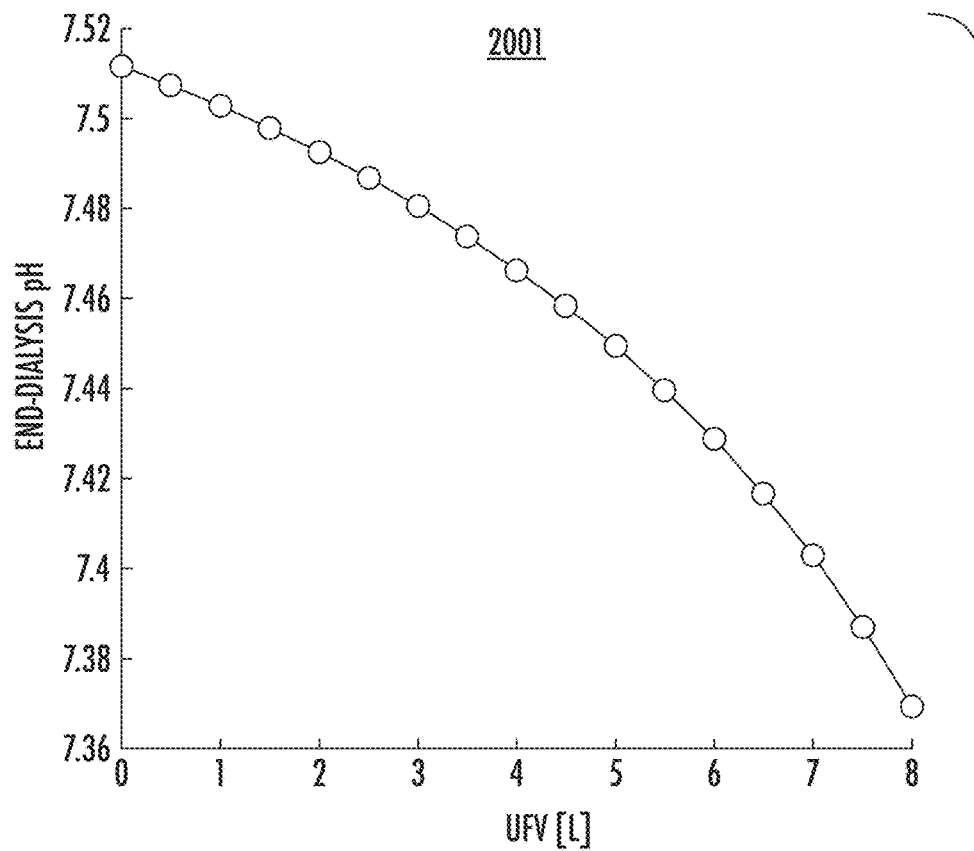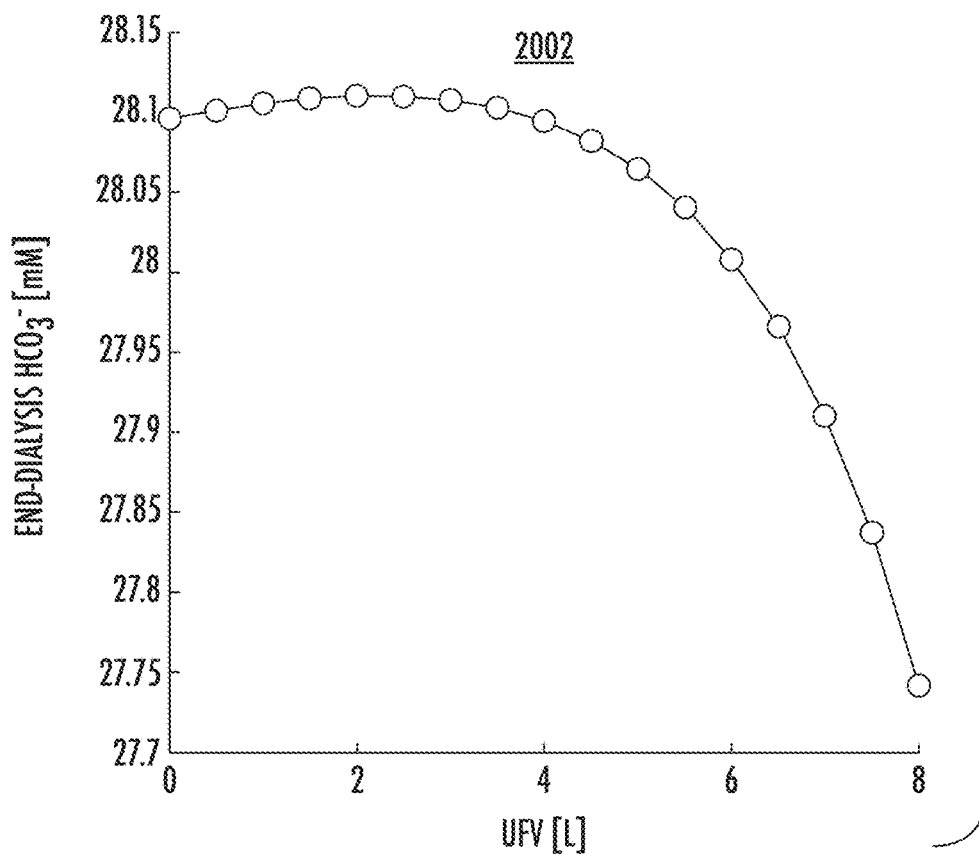
FIG. 20

TECHNIQUES FOR DETERMINING ACID-BASE HOMEOSTASIS

CROSS-REFERENCE TO RELATED APPLICATION

This application claims priority to U.S. Provisional Patent Application Ser. No. 62/816,446, filed on Mar. 11, 2019, entitled "Techniques for Determining Acid-Base Homeostasis," the contents of which are incorporated herein by reference.

FIELD

The disclosure generally relates to processes for modeling the functionality of portions of the human body to determine acid-base homeostasis information, and, more particularly, to modelling acid-base homeostasis under normal conditions and acid-base alteration conditions (or disorders), including during a dialysis process, for providing treatment recommendations.

BACKGROUND

Precise maintenance of pH and acid-base homeostasis is fundamental for optimal functioning of physiological and cellular function. The presence of an acid-base disturbance can affect clinical outcomes and is sometimes associated with an underlying disease. Accordingly, it is important to assess the acid-base status of patients and the extent to which various therapeutic treatments are effective in controlling these acid-base alterations.

The impact of acid-base alterations has far-reaching implications. In addition to physiochemical buffering, acid-base homeostasis is regulated by respiratory and renal systems. Changes in pH affect numerous physiochemical reactions and buffering systems, transport/channel kinetics, muscle contraction, metabolic enzymatic activity, and protein/membrane structures and functions. Alterations in pH can also impact cardiovascular, central nervous, renal and pulmonary systems, tissue metabolism and oxygenation, and bone remodeling, among other things. For example, chronic $H^+$ retention can lead to increased muscle protein degradation and muscle wasting. Furthermore, through different synergistic pathways, $H^+$ retention can increase bone dissolution, cell-mediated bone resorption, and decrease bone formation. Similarly, $H^+$ retention can also result in renal injury and nephrolithiasis and may accelerate progression of chronic kidney disease (CKD).

Clinical studies are an important tool for understanding acid-base regulatory systems in patients, particularly those with abnormal health conditions. However, clinical studies are expensive, time-consuming, and resource-intensive. Accordingly, virtual models of biological systems have been used to attempt to model acid-base conditions without the need for real-world patients, regulations, and cost. Although some models have been described for modeling acid-base conditions, such modeling has been severely limited. For example, conventional models have focused on very specific conditions, such as tumor-blood pH exchange kinetics, $HCO_3$ dilution, and/or the like, and/or have disregarded the effects of treatment processes, such as dialysis therapy. Accordingly, conventional virtual models have ignored important physiological aspects affecting pH and acid-base homeostasis and, therefore, do not accurately reflect acid-base homeostasis in many real patient populations. As a result, conventional virtual models are not able to provide precise and comprehensive acid-base homeostasis information and/or treatment recommendations.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

In accordance with various aspects of the described embodiments, a method of acid-base homeostasis analysis may include providing a physiological acid-base model configured to model acid-base homeostasis of a virtual patient, the physiological acid-base model to determine a plurality of operating parameters for an $HCO_3/CO_2$ buffering system having renal and pulmonary regulatory mechanisms, determine acid-base information comprising a bicarbonate concentration, a carbon dioxide concentration, and a free hydrogen ions concentration via simulating the $HCO_3/CO_2$ buffering system, and determine predicted patient information based on the acid-base information. In some embodiments, the method of acid-base homeostasis analysis may be a computer-implemented method performed via a processor of a computing device.

In various embodiments of the method, the predicted patient information may include at least one of a serum pH level, a $pCO_2$ level, or a $HCO_3$ level. In various embodiments of the method, the plurality of operating parameters may be configured to indicate a health condition of the virtual patient. In exemplary embodiments of the method, the health condition may include one of a normal physiological state and an acid base disorder, the acid base disorder comprising one of metabolic acidosis, metabolic alkalosis, respiratory acidosis, and respiratory alkalosis. In various embodiments of the method, the $HCO_3/CO_2$ buffering system may be configured to simulate an acid-base disorder based on a selection of the plurality of operating parameters to disequilibriate one or more of $pCO_2$ and $HCO_3$. In some embodiments of the method, the predicted patient information may include at least one secondary compensatory response induced by the acid-base disorder. In various embodiments of the method, the method may include determining at least one of the plurality of operating parameters associated with correcting a simulated acid-base disorder.

In some embodiments of the method, the bicarbonate concentration may be determined via the following:

$$\frac{dY_{HCO_3^-}}{dt} = J_{HCO_3^-} + \phi_{CO_2} Y_{CO_2} - D_{HCO_3^-} Y_{HCO_3^-} - K_{H^+,HCO_3^-} Y_{H^+} Y_{HCO_3^-} + K_{CO_2} Y_{CO_2}.$$

In some embodiments of the method, the carbon dioxide concentration may be determined via the following:

$$\frac{dY_{CO_2}}{dt} = P_{CO_2} - D_{CO_2} V_0 Y_{CO_2} + K_{H^+,HCO_3^-} Y_{H^+} Y_{HCO_3^-} - K_{CO_2} Y_{CO_2}.$$

In exemplary embodiments of the method, the free hydrogen ions concentration may be determined via the following:

$$\frac{dY_{H^+}}{dt} = P_{H^+} - \gamma_{H^+}Y_{H^+} - K_{H^+,HCO_3^-}Y_{H^+}Y_{HCO_3^-} + K_{CO_2}Y_{CO_2}.$$

In various embodiments of the method, the method may include determining at least one treatment recommendation based on the prediction information. In some embodiments of the method, the at least one treatment recommendation may include at least one of an $HCO_3$ supplement dosage, an acid-binder dosage, dialysis bicarbonate dialysate dosage, or diet instructions. In various embodiments of the method, the method may include determining at least one primary parameter of an acid-base disorder of the patient, and determining the at least one treatment recommendation based on the at least one primary parameter to treat the acid-base disorder. In various embodiments of the method, the at least on primary parameter may include at least one cause of an acid-base disorder of the patient.

In accordance with various aspects of the described embodiments an apparatus may include at least one processor, a memory coupled to the at least one processor, the memory comprising instructions that, when executed by the at least one processor, cause the at least one processor to perform an acid-base homeostasis analysis process to, access an intradialytic acid-base model configured to model acid-base homeostasis of a virtual patient having impaired acid-base homeostasis functional, the intradialytic acid-base model to determine a plurality of operating parameters for an $HCO_3/CO_2$ buffering system having renal and pulmonary regulatory mechanisms, determine acid-base information comprising a bicarbonate concentration, a carbon dioxide concentration, and a free hydrogen ions concentration via simulating the $HCO_3/CO_2$ buffering system, and determine predicted patient information based on the acid-base information.

In some embodiments of the apparatus, the predicted patient information may include a serum pH level. In some embodiments of the apparatus, the plurality of operating parameters may be configured to indicate a health condition of the virtual patient, the health condition comprising one of a normal physiological state and an acid base disorder, the acid base disorder comprising one of metabolic acidosis, metabolic alkalosis, respiratory acidosis, and respiratory alkalosis, and/or mixed disorder. In various embodiments of the apparatus, the $HCO_3/CO_2$ buffering system may be configured to simulate an acid-base disorder based on a selection of the plurality of operating parameters to disequilibriate one or more of $pCO_2$ and $HCO_3$. In exemplary embodiments of the apparatus, the predicted patient information may include at least one secondary compensatory response induced by the acid-base disorder.

In some embodiments of the apparatus, the bicarbonate concentration may be determined via the following:

$$\frac{dY_{HCO_3^-}}{dt} = J_{HCO_3^-} + \phi_{CO_2}Y_{CO_2} - D_{HCO_3^-}Y_{HCO_3^-} - K_{H^+,HCO_3^-}Y_{H^+}Y_{HCO_3^-} + K_{CO_2}Y_{CO_2}.$$

In some embodiments of the apparatus, the carbon dioxide concentration may be determined via the following:

$$\frac{dY_{CO_2}}{dt} = P_{CO_2} - D_{CO_2}V_0Y_{CO_2} + K_{H^+,HCO_3^-}Y_{H^+}Y_{HCO_3^-} - K_{CO_2}Y_{CO_2}.$$

In some embodiments of the apparatus, the free hydrogen ions concentration may be determined via the following:

$$\frac{dY_{H^+}}{dt} = P_{H^+} - \gamma_{H^+}Y_{H^+} - K_{H^+,HCO_3^-}Y_{H^+}Y_{HCO_3^-} + K_{CO_2}Y_{CO_2}.$$

In accordance with various aspects of the described embodiments is a method of acid-base homeostasis analysis may include providing an intradialytic acid-base model configured to model acid-base homeostasis of a virtual patient having an impaired functionality affecting acid-base homeostasis, the intradialytic model comprising a dialysis patient model configured to simulate a patient undergoing hemodialysis (HD), and a dialyzer model configured to simulate an HD dialyzer system; and determining predicted patient information based on acid-base information generated via simulating the intradialytic acid-base model. In some embodiments, the method of acid-base homeostasis analysis may be a computer-implemented method performed via a processor of a computing device.

In some embodiments of the method, the predicted patient information may include a serum pH level. In some embodiments of the method, the dialysis patient model to simulate patient information may include a distribution volume ($V_{ex}$) and concentrations of acid-base variables ($C_{ex}=\{C_{H^+}, C_{HCO_3^-}, C_{CO_2}\}$). In some embodiments of the method, the dialyzer model may be configured to model renal regulation of $HCO_3$ and $H^+$ via simulating a dialysis process on the virtual patient.

In some embodiments of the method, the intradialytic acid-base model may be configured to dynamically model acid-base homeostasis of the virtual patient via the following:

$$\frac{d(C_{H^+}V_{ex})}{dt} = \underbrace{P_{H^+}}_{\text{Endogenous } H^+ \text{ production}} - \underbrace{\gamma_{H^+}C_{H^+}}_{\text{Lumped non-bicarbonate}} - \underbrace{(K_{H^+,HCO_3^-}C_{H^+}C_{HCO_3^-} + K_{CO_2}C_{CO_2})V_{ex}}_{\text{Henderson–Hasselbach kinetics}},$$

$$\frac{d(C_{HCO_3^-}V_{ex})}{dt} = \underbrace{-Q_PC_{HCO_3^-}}_{\text{Flux from patient}} + \underbrace{(Q_P - Q_{uf})C_{HCO_3^-,out}}_{\text{Post-dialyzer flux to patient}} -$$

$$\underbrace{(K_{H^+,HCO_3^-}C_{H^+}C_{HCO_3^-} + K_{CO_2}C_{CO_2})V_{ex}}_{\text{Henderson–Hasselbach kinetics}},$$

$$\frac{d(C_{CO_2}V_{ex})}{dt} = \underbrace{P_{CO_2}}_{\text{Endogenous } CO_2 \text{ production}} - \underbrace{D_{CO_2}V_0C_{CO_2}}_{\text{Respiratory ventilation}} +$$

$$\underbrace{(K_{H^+,HCO_3^-}C_{H^+}C_{HCO_3^-} + K_{CO_2}C_{CO_2})V_{ex}}_{\text{Henderson–Hasselbach kinetics}}.$$

In accordance with various aspects of the described embodiments a method of treating an acid-base disorder of a patient may include receiving acid-base information generated via an acid-base model configured to model acid-base homeostasis of a patient, the acid-base information comprising at least one primary parameter indicating a cause of the acid-base disorder; and determining at least one treatment recommendation to affect the at least one primary parameter to treat the acid-base disorder. In some embodiments, the method of acid-base homeostasis analysis may be a computer-implemented method performed via a processor of a computing device.

In some embodiments of the method, the acid-base disorder may include at least one of metabolic acidosis, metabolic alkalosis, respiratory acidosis, or respiratory alkalosis. In various embodiments of the method, the at least one primary parameter may affect a pH level of the patient. In some embodiments of the method, the at least one primary parameter may include at least one cause of an acid-base disorder of the patient. In exemplary embodiments of the method, the at least one treatment recommendation may include at least one of an $HCO_3$ supplement dosage, an acid-binder dosage, dialysis bicarbonate dialysate dosage, or diet instructions.

In some embodiments of the method, the at least one primary parameter may include at least one of ventilation rate, $CO_2$ production rate, acid secretion rate, renal filtration rate, $HCO_3$ therapy, dehydration rate, hydration rate, acid removal rate, or $H^+$ production rate.

In some embodiments of the method, the method may include determining $HCO_3$ buffer capacity of at least one patient. For example, the buffer capacity among patients may be different and could impact the amount of $HCO_3^-$ needed to increase pH per unit, thereby affecting a treatment recommendation.

In some embodiments of the method, the method may include determining patient-specific acid-base dose response curves. In various embodiments, the at least one acid-base model may operate to simulate serum pH in both normal conditions and acid-base disorders. In some embodiments of the method, the acid-base model may include a physiological acid-base model. In various embodiments of the method, the acid-base model may include an intradialytic acid-base model.

In various embodiments, the acid-base model may operate to predict secondary compensations, for example, in response to an acid-base disorder and/or treatment thereof. In exemplary embodiments, the acid-base model may capture at least one qualitative response of therapeutic corrections of the acid base disorders. In some embodiments, the acid-base model may predict potential therapeutic targets for the acid-base disorder.

BRIEF DESCRIPTION OF THE DRAWINGS

By way of example, specific embodiments will now be described, with reference to the accompanying drawings, in which:

FIG. 3 illustrates parameter information for an acid-base model according to some embodiments;

FIG. 4 illustrates parameter information for an acid-base model according to some embodiments;

FIG. 6A illustrates physiological acid-base model validation results under metabolic acidosis conditions according to some embodiments;

FIG. 7 illustrates a table of linear equation information for secondary compensatory responses for acid-base disorders according to some embodiments;

FIG. 8 illustrates parameter descriptions and values for a quantification process with sensitivity analysis according to some embodiments;

FIG. 11 illustrates a table of intradialytic acid-base model parameters and values according to some embodiments;

FIGS. 13-26 illustrate intradialytic acid-base model validation information according to some embodiments.

DETAILED DESCRIPTION

Figure 1:
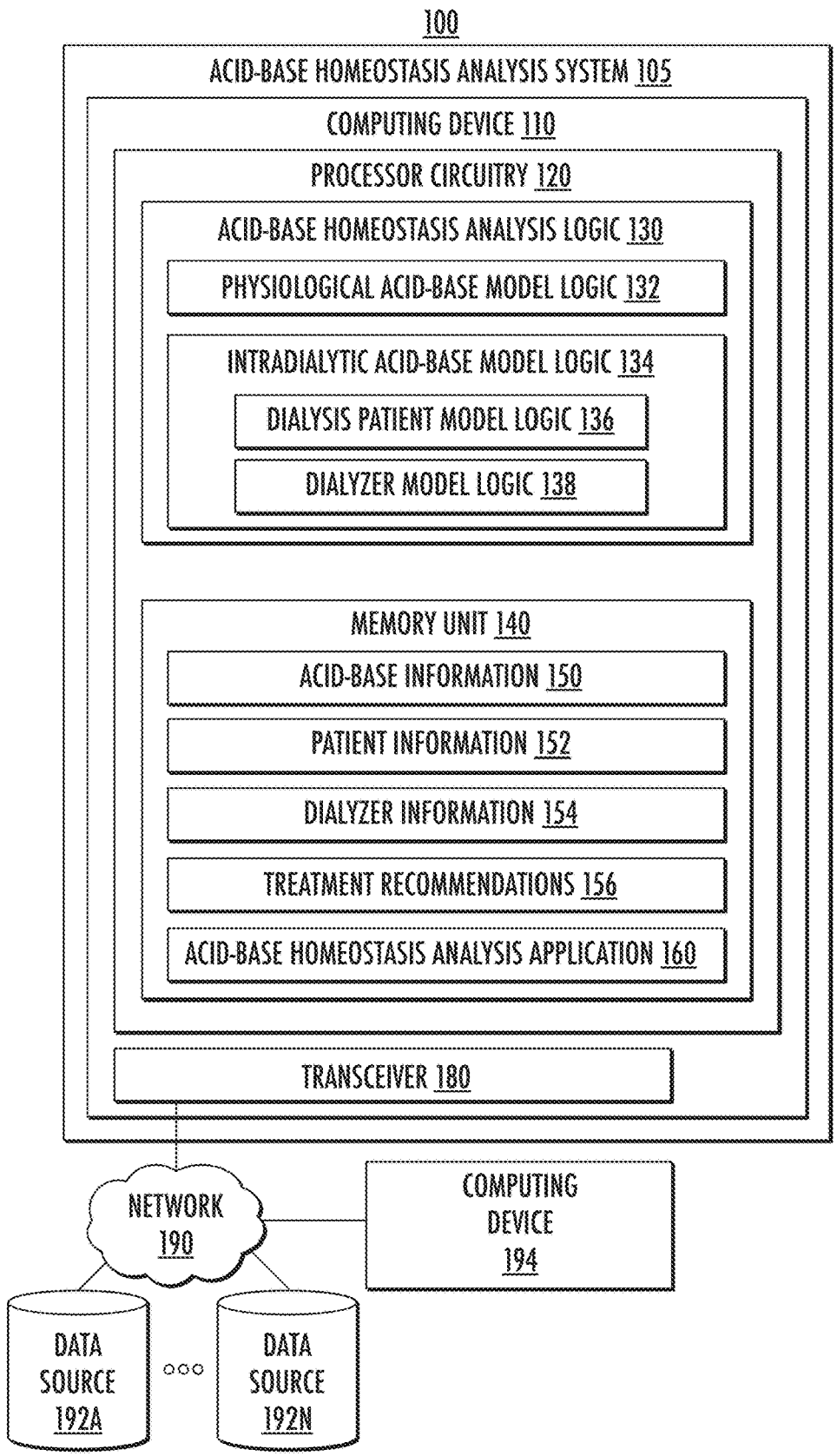
FIG. 1 illustrates a first exemplary operating environment in accordance with the present disclosure.
Figure 2:
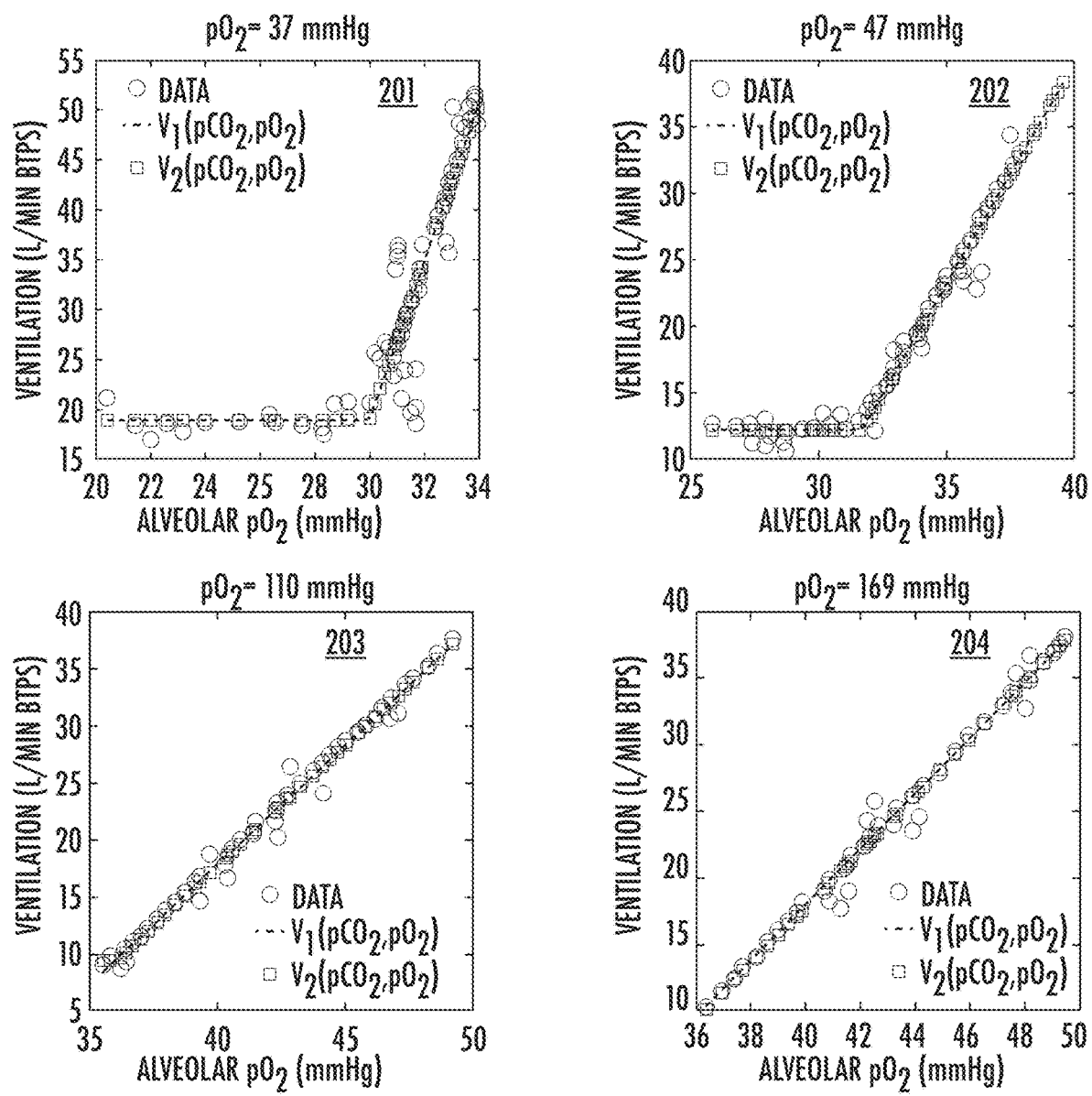
FIG. 2 illustrates empirical data for a ventilation function.

The present embodiments will now be described more fully hereinafter with reference to the accompanying drawings, in which several exemplary embodiments are shown. The subject matter of the present disclosure, however, may be embodied in many different forms and should not be construed as limited to the embodiments set forth herein. Rather, these embodiments are provided so that this disclosure will be thorough and complete and convey the scope of the subject matter to those skilled in the art. In the drawings, like numbers refer to like elements throughout.

The described technology may generally include an acid-base homeostasis analysis process operative to simulate pH and acid-base homeostasis for virtual patients and/or virtual patient populations. In some embodiments, a virtual patient may be or may include a patient, a physiological system (for instance, renal system, pulmonary system, respiratory system, organs thereof, functions thereof, and/or the like), a patient population, portions thereof, virtual models thereof, and/or the like. In some embodiments, the acid-base homeostasis analysis process may use one or more acid-base models that may include the major physiological components and mechanisms governing pH and acid-base homeostasis in patients, including healthy (or normal) patients, patients with abnormalities or disorders, and/or patients undergoing treatment regimens (for instance, dialysis, such as hemodialysis (HD)). In various embodiments, the acid-base models may include one or more physiological acid-base models (for instance, a general model of a patient) and one or more intradialytic acid-base models to simulate dialysis patients and dialyzer operation. In various embodiments, intradialytic acid-base models may include one or more of a dialysis patient model (for instance, a model with impaired functionality corresponding to dialysis patients, such as impaired renal regulation), and a dialyzer model to simulate intradialytic dynamics associated with pH and acid-base homeostasis.

In some embodiments, the acid-base models may operate as a dynamic model of the physiological regulation of a $HCO_3/CO_2$ buffering system. As described in more detail below, in various embodiments, the acid-base models may be configured using, at least in part, Henderson-Hasselbalch kinetics. For example, some embodiments may include acid-base models of the HCO3-/CO2 buffering system with Henderson-Hasselbalch mass-action kinetics, which incorporate body production of both CO2 and H+, non-bicarbonate buffering, and the physiologic regulation of the HCO3-/CO2 buffer system through ventilation and renal excretion. In exemplary embodiments, acid-base models may include a dialyzer model quantitating the intradialytic dynamics of HCO3- and H+, which may be parameterize to model anuric patients receiving HD. In exemplary embodiments, the acid-base models may simulate a normal physiological state and several acid-base disorders, including, without limitation, metabolic acidosis and alkalosis, and respiratory acidosis and alkalosis.

The acid-base models according to some embodiments may provide multiple technological advantages over conventional models, systems, methods, and/or the like, including improvements in computing technology. In one non-limiting technological advantage, acid-base models according to some embodiments may provide for accurate predictions of patient pH and/or acid-base homeostasis physiological conditions, such as the prediction serum pH under a range of physiological conditions. In another non-limiting technological advantage, acid-base models according to some embodiments may provide for qualitative validation (for example, via comparisons of in-silico results with clinical data on acid-base homeostasis and alterations), demonstrating clear relationships between primary acid-base disturbances and secondary adaptive compensatory responses. In an additional non-limiting technological advantage, acid-base models according to some embodiments may be used to provide predicted primary disturbances that accurately produce clinically observed compensatory responses. In another non-limiting technological advantage, acid-base models according to some embodiments may provide for, for instance via sensitivity analysis, identification of key parameters that may be the most effective in regulating systemic pH in healthy individuals and those with certain conditions, such as chronic kidney disease (CKD), distal and proximal renal tubular acidosis, and other conditions.

In a non-limiting technological advantage, acid-base models according to some embodiments may provide for more complete models than those provided using conventional techniques, including, without limitation, non-bicarbonate buffering of the $HCO_3/CO_2$ buffer system, renal and pulmonary regulation of the acid-base kinetics, bicarbonate and bicarbonate buffering, and others described herein. In an additional non-limiting technological advantage, acid-base models according to some embodiments may provide for an improvement in computing technology by providing concrete, identifiable pathophysiologic insights that can, for example, serve as a tool to assess the safety and efficacy of different therapeutic interventions to control or correct acid-base disorders that may not be provided by conventional computing technology. Other technological advantages are provided in this Detailed Description. Embodiments are not limited in this context.

Regulation of pH and acid-base homeostasis in the blood and in the extracellular fluid plays a pivotal role in many aspects of cellular metabolism and other physiological functions. The impact of acid-base alterations has far-reaching implications. In addition to physiochemical buffering, acid-base homeostasis is regulated by respiratory and renal systems. Changes in pH affect numerous physiochemical reactions and buffering systems, transport/channel kinetics, muscle contraction, metabolic enzymatic reactivities, and protein/membrane structures and functions. Alterations in pH also impact cardiovascular, central nervous, renal and pulmonary systems, tissue metabolism and oxygenation, and bone remodeling, to name some examples. For instance, chronic $H^+$ retention can lead to increased muscle protein degradation and muscle wasting. In addition, through different synergistic pathways, $H^+$ retention can, among other things, increase bone dissolution, cell-mediated bone resorption, and decrease bone formation. Similarly, $H^+$ retention can also result in renal injury and nephrolithiasis and may accelerate progression of CKD.

Pulmonary ventilation is controlled by partial arterial pressure of $CO_2$ ($pCO_2$), partial pressure of oxygen, and pH. Central chemoreceptors (located near the ventral surface of the medulla oblongata of the brain) and peripheral chemoreceptors (located in the carotid bodies and aortic bodies of the aortic arch) respond to changes in $pCO_2$ by triggering a respiratory response, which in turn affects bicarbonate ($HCO_3$ or $HCO_3^-$) concentration and, thereby, changes in the pH level. Similarly, the kidney is responsible for the regulation of $HCO_3$ through reabsorption, production, and, in some situations, excretion of $HCO_3$. Kidneys reabsorb almost all of the altered $HCO_3$ in the proximal and distal tubular segments of the nephrons and produce new $HCO_3$ to replace the amount consumed by acids through excretion of titratable acids and ammonium.

Pure alterations in acid-base homeostasis may include one of four primary disorders: metabolic acidosis, metabolic alkalosis, respiratory acidosis, and respiratory alkalosis. In addition to these pure acid-base alterations, combinations can occur ("mixed" acid-base disorders). An acid-base disorder is metabolic or respiratory depending on whether the changes in $HCO_3$ or in $pCO_2$ are due to abnormalities of renal or respiratory functions, respectively. In particular, an acid-base disorder is termed metabolic when the primary abnormality can be attributed to changes in $HCO_3$, either as a result of an imbalance between net $H^+$ production and renal $HCO_3$ reabsorption, or due to $HCO_3$ renal or gastrointestinal absorptive and secretion defects. An acid-base disorder may be termed respiratory if the primary abnormality is due to changes in $pCO_2$ caused by imbalances between metabolic production and pulmonary excretion of $CO_2$ or an abnormality in respiratory function. The status of acid-base disorders is acidotic or alkalotic if the blood pH is below or above the normal physiological range, respectively. In some embodiments, the normal physiological range may be a pH of about 7.4±0.02. Accordingly, acidosis or alkalosis may refer to the process in which $H^+$ concentration is increased or decreased, respectively.

In some embodiments, acid-base models may operate to examine quantitative alterations of systemic buffer kinetics, for instance, modelling serum pH regulation using the $HCO_3/CO_2$ system, including renal and respiratory regulatory mechanisms. In various embodiments, acid-base models may simulate acid-base disorders, including, for example, metabolic acidosis and alkalosis and respiratory acidosis and alkalosis. In various embodiments, acid-base models may be used to perform uncertainty quantification and sensitivity analyses, for instance, to identify parameters that can be altered to treat or correct a pathophysiological disorder.

FIG. 1 illustrates an example of an operating environment 100 that may be representative of some embodiments. As shown in FIG. 1, operating environment 100 may include an acid-base homeostasis analysis system 105. In various embodiments, acid-base homeostasis analysis system 105 may include a computing device 110 communicatively coupled to network 190 via a transceiver 180. In some embodiments, computing device 110 may be a server computer or other type of computing device.

Computing device 110 may be configured to manage, among other things, operational aspects of an acid-base homeostasis process according to some embodiments. Although only one computing device 110 is depicted in FIG. 1, embodiments are not so limited. In various embodiments, the functions, operations, configurations, data storage functions, applications, logic, and/or the like described with respect to computing device 110 may be performed by and/or stored in one or more other computing devices (not shown), for example, coupled to computing device 110 via network 190 (for instance, one or more of client or peer devices 194). A single computing device 110 is depicted for illustrative purposes only to simplify the figure. Embodiments are not limited in this context.

Computing device 110 may include a processor circuitry 120 that may include and/or may access various logics for performing processes according to some embodiments. For instance, processor circuitry 120 may include and/or may access acid-base homeostasis analysis logic 130, physiological acid-base model logic 132, intradialytic acid-base model logic 134, dialysis patient model logic 136, and/or dialyzer model logic 138. Processing circuitry 120, acid-base homeostasis analysis logic 130, physiological acid-base model logic 132, intradialytic acid-base model logic 134, dialysis patient model logic 136, and/or dialyzer model logic 138, and/or portions thereof may be implemented in hardware, software, or a combination thereof. As used in this application, the terms "logic," "component," "layer," "system," "circuitry," "decoder," "encoder," "control loop," and/or "module" are intended to refer to a computer-related entity, either hardware, a combination of hardware and software, software, or software in execution, examples of which are provided by the exemplary computing architecture 2800. For example, a logic, circuitry, or a module may be and/or may include, but are not limited to, a process running on a processor, a processor, a hard disk drive, multiple storage drives (of optical and/or magnetic storage medium), an object, an executable, a thread of execution, a program, a computer, hardware circuitry, integrated circuits, application specific integrated circuits (ASIC), programmable logic devices (PLD), digital signal processors (DSP), field programmable gate array (FPGA), a system-on-a-chip (SoC), memory units, logic gates, registers, semiconductor device, chips, microchips, chip sets, software components, programs, applications, firmware, software modules, computer code, a control loop, a computational model or application, an AI model or application, an ML model or application, variations thereof, combinations of any of the foregoing, and/or the like.

Although acid-base homeostasis analysis logic 130 is depicted in FIG. 1 as being within processor circuitry 120, embodiments are not so limited. For example, acid-base homeostasis analysis logic 130, physiological acid-base model logic 132, intradialytic acid-base logic 132, dialysis patient model logic 136, and/or dialyzer model logic 138, and/or any component thereof may be located within an accelerator, a processor core, an interface, an individual processor die, implemented entirely as a software application (for instance, an acid-base homeostasis analysis application 160), and/or the like.

Memory unit 140 may include various types of computer-readable storage media and/or systems in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (for example, USB memory, solid state drives (SSD) and any other type of storage media suitable for storing information. In addition, memory unit 140 may include various types of computer-readable storage media in the form of one or more lower speed memory units, including an internal (or external) hard disk drive (HDD), a magnetic floppy disk drive (FDD), and an optical disk drive to read from or write to a removable optical disk (for example, a CD-ROM or DVD), a solid state drive (SSD), and/or the like.

Memory unit 140 may store various types of information and/or applications for an acid-base homeostasis process according to some embodiments. For example, memory unit 140 may store acid-base information 150, patient information 152, dialyzer information 154, treatment recommendations 156, and/or acid-base homeostasis analysis application 160. In some embodiments, some or all of acid-base information 150, patient information 152, dialyzer information 154, treatment recommendations 156, and/or acid-base homeostasis analysis application 160 may be stored in one or more data stores 192a-n accessible to computing device 110 via network 190. For example, one or more of data stores 192a-n may be or may include a clinical data repository or database, a health information system (HIS), an electronic medical record (EMR) system, a dialysis information system (DIS), a picture archiving and communication system (PACS), a Centers for Medicare and Medicaid Services (CMS) database, U.S. Renal Data System (USRDS), a proprietary database, and/or the like. In some embodiments, memory 140 and/or data sources 192a-n may store historical patient population information, for example, used according to some embodiments to verify acid-base model outcomes.

In some embodiments, acid-base homeostasis analysis logic 130, for example, via physiological acid-base model logic 132 and/or acid-base homeostasis analysis application 160, may operate to simulate acid-base homeostasis according to some embodiments. In various embodiments, acid-base homeostasis analysis logic 130, for example, via intradialytic acid-base model logic 134 and/or acid-base homeostasis analysis application 160, may operate to simulate acid-base homeostasis for a dialysis patient undergoing dialysis treatment according to some embodiments. Dialysis patient model logic 136 may operate to implement a dialysis patient model according to various embodiments. Dialyzer model logic 138 may operate to implement a dialyzer model according to some embodiments.

In various embodiments, acid-base information 150 may include parameters, variables, values, and/or the like used by acid-base homeostasis analysis logic 130 and acid-base models implemented by acid-base homeostasis analysis logic 130 and/or components thereof (see, for example, FIGS. 2, 5, 6, and 9). In various information, acid-base information 150 may include information generated by an acid-base model. For example, in various embodiments, acid-base information 150 may include predicted patient information determined by a model. For example, predicted patient information may include predicted pH (for instance, serum pH), $pCO_2$, and/or $HCO_3$ (see, for example, FIGS. 6A, 9A-9C, and 12-16).

In exemplary embodiments, patient information 152 may include information associated with virtual patients modeled via acid-base models according to some embodiments and/or actual patients of historical information, for instance, used to teach or validate the acid-base models. Non-limiting examples of patient information 152 may include gender, age, weight, dry weight, treatment regimen (for instance, HD) and doses (for example, $HCO_3$), pre/post dialysis information (for example, pH, $pCO_2$, $pO_2$, HCO3), and/or the like. In various embodiments, dialyzer information 154 may include information associated with an actual or virtual (i.e., modelled) dialyzer used for an acid-base model and/or validation thereof, such as ultrafiltration volume (UFV), UF rate (UFR), dialyzer type, machine model, treatment mode (hemodialysis, hemodiafiltration, etc), operating parameters, and/or the like.

In some embodiments, treatment recommendations 156 may include treatment recommendations, suggestions, plans, information, and/or the like generated by an acid-base model according to various embodiments. For example, an acid-base model according to some embodiments may generate a treatment recommendation 156 for a real-world patient and/or patient population based on a model outcome generated for a corresponding virtual patient and/or patient population. Non-limiting examples of treatment recommendations may include administering $HCO_3^-$ supplementation, acid-binders, hemodialysis bicarbonate dialysate, and/or patient diet instructions (for instance, restricting overconsumption of acidogenic diets). In a particular example, a treatment recommendation 156 may include a prescription of an optimized dialysate bicarbonate concentration to restore acid-base homeostasis without generating an "overshoot" metabolic alkalosis. In some embodiments, a treatment recommendation 156 for a patient and/or patient population (for instance, population of patients with particular characteristics (e.g., gender, weight, health condition, and/or the like)) may be generated based on a primary parameter and/or predicted patient information for patients and/or patient populations (and/or virtual implementations thereof) associated with the patient and/or patient population. In some embodiments, a primary parameter (see, for example, the population of parameters listed in FIG. 4) may include one or more parameters that influence a condition (see, for example, FIGS. 9A-9C). For example, for healthy individuals, the predominant parameters affecting pH are those involving renal function (acid secretion rate ($\phi_{CO_2}$) and $HCO_3^-$ reabsorption rate ($D_{HCO_3^-}$)), $HCO_3^-$ therapy ($J_{HCO_3^-}$), reaction rates or $pK_a$ of the buffer system, production ($P_H$) and removal or non-bicarbonate buffering of protons ($\gamma_H$). Therapies targeting these parameters may have a strong effect on correcting pH disturbances. Accordingly, these may be primary parameters for pH acid-base homeostasis for healthy individuals. For individuals with metabolic acidosis, primary parameters may include respiratory $CO_2$ removal ($D_{CO_2}$), $HCO_3^-$ supplementation or therapy ($P_{HCO_3^-}$, for example, $NaHCO_3$ or HD), hydration reaction rate ($K_{H^+,HCO_3^-}$), and/or removal of excess protons (for example, through acid-binder supplementation) will be effective.

Acid-base models according to some embodiments may model an acid-base disorder for a certain patient population to determine predicted patient information (e.g., pH level, $pCO_2$ level, and/or $HCO_3$ level). The acid-base models may be used to determine predicted patient information for certain treatments (predicted treatment information), which may model treatment results for a patient. In some embodiments, a treatment recommendation may include maintaining/regulating acid-base homeostasis. Due to the accuracy of the acid-base models described according to some embodiments in predicting treatment outcomes, the acid-base models may be used to generate useful treatment recommendations for patients compared with conventional systems. In some embodiments, primary parameters may be determined based on predicted patient information (for instance, running an acid-base model to determine primary parameters affecting an acid-base disorder). Treatment recommendations 156 may be targeted to affect primary parameters in order to effectively address a condition. Embodiments are not limited in this context.

Some embodiments may provide an acid-base model in the form of a physiological acid-base model (for example, implemented via physiological acid-base model logic 132). In various embodiments, a physiological acid-base model may provide a physiologically-based model describing acid-base homeostasis under normal (or substantially normal) physiologic conditions that may be used, for example, to analyze the effects of pathophysiologic acid-base perturbations on the acid-base status of a patient (or virtual patient). In exemplary embodiments, a physiological acid-base model may operate to model, process, analyze, experiment, or otherwise simulate, among other things, the physiological regulation of $HCO_3^-/CO_2$ buffering system with Henderson-Hasselbalch mass-action kinetics, endogenous production of both $CO_2$ and $H^+$, non-bicarbonate buffering, and/or renal and respiratory regulations.

Various embodiments may provide acid-base models in the form of intradialytic models (for instance, implemented via intradialytic acid-base model logic 134, dialysis patient model logic 136, and/or dialyzer model logic 138). In some embodiments, the intradialytic models may be or may include a dialysis patient model (for instance, implemented via dialysis patient model logic 136) that may include an implementation of a physiological acid-base model for a dialysis patient, for example, characterized by impaired renal regulation that has been replaced by dialysis (for instance, hemodialysis (HD)). In various embodiments, the intradialytic models may be or may include a dialyzer model (for instance, implemented via dialyzer model logic 138) operative to model a dialyzer, for example, to model, process, analyze, experiment, or otherwise simulate a dialyzer (for instance, an HD dialyzer) to incorporate intradialytic dynamics.

As described in more detail below, the acid-base models according to some embodiments may be used to predict treatment outcomes and/or to provide treatment recommendations for various acid-base disorders. In some embodiments, certain model parameters may be altered to determine their effect on acid-base homeostasis. For instance, changes to an acid secretion rate parameter and a renal filtration rate parameter (for example, reducing or eliminating these parameters (e.g., setting their model value to zero)) may simulate an acid-base disorder, such as renal failure, metabolic acidosis, metabolic alkalosis, respiratory acidosis, respiratory alkalosis, and/or the like. Based on the particular configuration and operating processes of acid-base models according to some embodiments, they may be used to accurately predict changes to parameters (see, for example, FIGS. 3 and 4) affecting acid-base homeostasis.

In some embodiments, acid-base homeostasis logic 130 may operate to receive patient information 152 for a particular patient (for instance, gender, age, health (for example, renal failure, normal, and/or the like), $HCO_3$ level, pH, and/or the like) and determine a treatment recommendation 156 for maintaining acid-base homeostasis and/or treating an acid-base disorder. For example, in a healthy person, correcting a deficient $HCO_3$ level may be different than for a patient experiencing metabolic acidosis (see, for example, FIGS. 9A-C). In some embodiments, acid-base models may be used to model, predict, or otherwise process various treatment models (for instance, acid-binder therapies, $HCO_3$ therapies, and/or the like) to determine, predict, or otherwise analyze treatment outcomes that may be used to determine actual patient therapy regimens. In some embodiments, acid-base homeostasis logic 130 may include, implement, or otherwise process a feedback loop (or iterative) function for ongoing use of the acid-base models to adjust acid-base conditions, including through dialysis modifications (for example, adjusting ultrafiltration rate and/or volume), or administration of drugs, bicarbonate, etc. based on continuous predicted patient information. In some embodiments, as a treatment is administered (for example, during dialysis, supplement dosages, and/or the like), the treatment information may be used as input into an acid-base model to generate updated predicted patient information, which may then be used to determine treatment results and/or to update a treatment recommendation (including in real or substantially real time, for example, during a dialysis treatment).

A physiological acid-base model according to some embodiments may operate to model the effect of systemic acid-base homeostasis. In some embodiments, a physiological acid-base model may be implemented using a system of coupled nonlinear ordinary differential equations, for example, to describe the acid-base buffering kinetics through the $HCO_3$—$CO_2$ system and incorporating the relevant physiological regulatory mechanisms. In some embodiments, physiological acid-base models may focus on $HCO_3$—$CO_2$ buffering kinetics, which is the most effective buffer system that controls systemic pH.

The pH of extracellular fluid is mainly regulated by the following three mechanisms, which act on different timescales: (i) chemical acid-base buffering, (ii) respiratory control, and (iii) renal filtration. The following Equation (1) provides an illustrative and non-restrictive $HCO_3$ buffering system according to some embodiments:

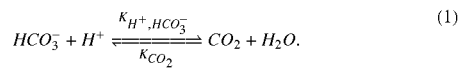

$$HCO_3^- + H^+ \underset{K_{CO_2}}{\overset{K_{H^+,HCO_3^-}}{\rightleftharpoons}} CO_2 + H_2O. \quad (1)$$

In some embodiments, in Equation (1), it may be assumed that carbonic anhydrase (CA) accelerates the carbonic acid reactions.

Chemical acid-base buffering prevents excessive changes in pH, where the timescale of this process is usually in seconds. The ability of the lung to increase or decrease ventilation allows it to regulate $CO_2$ removal as a gas in the expired air from the extracellular fluid, thereby adjusting the pH. In particular, due to continuous production of $CO_2$ as a by-product of cellular metabolism, the ventilation rate must be able to accommodate alterations in $CO_2$ in order to equilibrate the pH of the extracellular fluid. Although the process is fast, for example, occurring in a matter of minutes, it is less effective than chemical buffering. If the acid-base imbalance persists, then kidneys excrete either excess acid or base, an adaptation process that takes hours to days.

The kidneys, representing a very powerful regulatory system, have the ability to secrete large amounts of $H^+$ into the tubular lumen during metabolic acidosis. Also, excretion and reabsorption of $HCO_3$ take place in the proximal tubule and distal tubule. In particular, in the proximal tubule, $H^+$ is secreted through a $Na^+/H^+$ countertransport-facilitated process, while $HCO_3$ is reabsorbed by combining with $H^+$ to form carbonic acid ($H_2CO_3$) which is converted into $CO_2$ and $H_2O$ (via carbonic anhydrase enzymatic activity). In the intercalated cells, $H^+/Cl^-$ cotransporter facilitates the secretion of $H^+$. Although this process only accounts for 5% of the secreted $H^+$, it provides a gradient for the further secretion of more $H^+$ into the tubule lumen. Most of the secreted $H^+$ is used to reclaim the filtered $HCO_3$, and this rate of $HCO_3$ reabsorption is related to the rate of acid excretion.

To model the acid-base homeostatic process, physiological acid-base models according to some embodiments may track the concentrations of bicarbonate ($Y_{HCO_3^-}$), carbon dioxide ($Y_{CO_2}$) and free hydrogen protons ($Y_{H^+}$). Using Henderson-Hasselbalch mass-action kinetics with renal and pulmonary regulatory mechanisms, the homeostatic dynamics of the $HCO_3/CO_2$ acid-base system, as modelled by physiological acid-base models according to some embodiments may be configured according to the following Equations (2)-(4) (i.e., the physiological acid-base model equations or bicarbonate buffer kinetic system):

$$\frac{dY_{H^+}}{dt} = P_{H^+} - \gamma_{H^+} Y_{H^+} - K_{H^+,HCO_3^-} Y_{H^+} Y_{HCO_3^-} + K_{CO_2} Y_{CO_2}, \quad (2)$$

$$\frac{dY_{HCO_3^-}}{dt} = J_{HCO_3^-} + \phi_{CO_2} Y_{CO_2} - D_{HCO_3^-} Y_{HCO_3^-} - K_{H^+,HCO_3^-} Y_{H^+} Y_{HCO_3^-} + K_{CO_2} Y_{CO_2}, \quad (3)$$

$$\frac{dY_{CO_2}}{dt} = P_{CO_2} - D_{CO_2} V_0 Y_{CO_2} + K_{H^+,HCO_3^-} Y_{H^+} Y_{HCO_3^-} + K_{CO_2} Y_{CO_2},. \quad (4)$$

In some embodiments, in Equations (2)-(4) t∈$\mathbb{R}_0$:= [0, +∞) the following initial conditions: $Y_{H^+}(0)=H_0$, $Y_{HCO_3^-}(0)=B_0$, and $Y_{CO_2}(0)=C_0$, may set a patient (or virtual patient) to a normal physiological state. The parameter $P_{H^+}$ represents the cellular production of $H^+$, $\gamma_{H^+}$, denotes $H^+$ loss either due to renal clearance and/or non-bicarbonate buffering (for example, buffering with albumin, $Ca^{2+}$, $PO_4^{3-}$). The hydration and de-hydration reaction rates are given by the parameters $K_{H^+,HCO_3^-}$ and $K_{CO_2}$, respectively, where the values may be adjusted to reflect the carbonic anhydrase activity. In addition, $J_{HCO_3^-}$ denotes $HCO_3^-$ therapy and/or supplementation, $\phi_{CO_2}$ represents the acid secretion rate, $P_{CO_2}$ is the body or cellular (mitochondrial) production of $CO_2$, and $D_{HCO_3^-}$ represents the renal filtration rate of $HCO_3^-$. The effective ventilation rate ($D_{CO_2} V_0$) captures the pulmonary removal of $CO_2$, where $V_0$ is the minute volume ventilation, and $D_{CO_2}$ is the ventilation rate. In some embodiments, the kinetics of $H_2O$ is not included in Equations (2)-(4) because $H_2O$ is assumed to be abundant as a solvent. In some embodiments, Equations (2)-(4) may be formulated via general expressions (see, for example, Equations (5) and (6)), for instance, with non-linear ventilation ($D_{CO_2}V_0Y_{CO_2}$).

In various embodiments, the first two terms in Equation (2) may account for production of $P_{H^+}(t)$ of $H^+$ from the body, either through consumption and/or through other processes (for example, cellular metabolism), and for removal of $H^+$ as either a titratable acid and/or ammonium or non-carbonate buffering (for instance, buffering with phosphate and/or calcium). These two terms collectively correspond to $H^+$ mobilization due to buffering with non-bicarbonate buffers and other processes. The third and last terms in Equation (2) correspond to buffering reaction kinetics.

For Eq. (3), the first term, $J_{HCO_3^-}$, represents $HCO_3^-$ therapy, the second and third terms, $\phi_{CO_2}Y_{CO_2}$-$D_{HCO_3^-}Y_{HCO_3^-}$, may describe renal filtration processes, where it is assumed that the amount of $HCO_3^-$ lost to kidney from the blood through filtration may be related to filtered load, and the equivalence of $HCO_3^-$ reabsorption and acid excretion is through the splitting of $CO_2$ by intracellular carbonic anhydrase enzymatic activity. For example, an increase in $CO_2$ concentration may increase the conversion of $CO_2$ into $H^+$ and $HCO_3^-$ in a normally functioning kidney, which may result in higher acid secretion into the urine and $CO_2$ absorption into the bloodstream. Accordingly, the second term of Equation (3) may describe acid secretion, whereas the third term is the $HCO_3^-$ load to be filtered.

Similarly, Equation (4) may be directed to buffering kinetics, where the first term, $P_{CO_2}$, may be production of $CO_2$ in the body (for example, a cellular metabolic or mitochondrial process), and the second term, $D_{CO_2}V_0Y_{CO_2}$, is the removal of $CO_2$ through respiratory ventilation by the lung, which may depend on blood volume, cardiac output, arteriovenous difference (for example, the concentration difference between arterial and venous blood) of $CO_2$. To simplify the model, some embodiments may assume that ventilation rate $V_0$ is constant; however, $V_0$ may depend on $pCO_2$, oxygen partial pressure ($pO_2$), and/or pH.

In some embodiments, the term $D_{CO_2}V_0Y_{CO_2}$, may be nonlinear and may represent the effective ventilation rate, $D_{CO2} V(Y_{CO2}) Y_{CO_2}$, where $D_{CO2}$ becomes the ventilation rate and V denotes the minute volume ventilation. The functional relationship may be motivated by empirical data in FIG. 2, and by the simplification of the processes controlling ventilation. The empirical ventilation function may take the form of one of the following Equations (5) or (6):

$$V_1(pCO_2, pO_2) = V_0 + V_p e^{-0.05 pO2(t)} \max\{0, pCO_2(t) - I_p\} \quad (5),$$

$$V_2(pCO_2, pO_2) = V_0 + V_p(102.4 - S_{O_2}(t)) \max\{0, pCO_2(t) - I_p\} \quad (6),$$

where $V_0$ and $V_p$ represent baseline and slope parameters, and $I_p$ is the cutoff threshold. In the ventilation term, the role of pH sensors in the medulla oblongata in regulating bicarbonate buffering homeostasis is disregarded as de minimus. The ventilation term $V_1(pCO_2, pO_2)$ above relates the interaction between partial pressure $pCO_2$ and $pO_2$ and their effects on ventilation. In $V_2(pCO_2, pO_2)$, $V_2(pCO_2, pO_2)$ uses an oxygen saturation function, $S_{O_2}$, which may be expressed in terms of $pO_2$. $Y_{CO_2}$ and $pCO_2$ are related by $Y_{CO_2}=0.03[(mmol/L)/mmHg] \times pCO_2$. In some embodiments, we may also assume that $pO_2$ is constant. At normal $pO_2$, ventilation increases by 2.5 L/min for every 1 mm Hg increase of $pCO_2$ (see FIG. 2 and parameter values listed in FIG. 3). From the above Equations (5) and (6) and FIG. 2, lowering $pO_2$ increases ventilation for a given $pCO_2$ and the steepness of the net effective slope of ventilation. The term $V_0$ can be replaced by either of the functional expressions above under the assumption that $pO_2$ is constant or exogenously provided. In some embodiments, the simplified version may be used to determine acid-base dynamics according to some embodiments, thereby reducing the number of model parameters that need to be identified. In other embodiments, all the effects of ventilation may be lumped into ventilatory rate parameters. In some embodiments, Equations (5) and (6) may provide general physiological acid-base models (for example, with Equations (2)-(4) being a specific implementation thereof).

FIG. 4 depicts illustrative parameter information for the bicarbonate buffer kinetic system of the physiological acid-base model, for example, as used in Equations (2)-(4). The calculated values in table 402 of FIG. 4 were derived from steady-state assumptions. For the examples provided herein (see, for example, FIGS. 5A-5B, 6A, 6B, and FIGS. 9A-9C), Equations (2)-(4) were solved using stiff ode15s solver in MATLAB®, provided by The MathWorks, Inc., Natick, Massachusetts, USA, where the physiological acid-base model is parameterized to normal physiological initial conditions of $pCO_{2=40}$ mmHg, $HCO_3^-=24$ mmol/L, and pH=7.2 (other model parameters are obtained from historical data, see table 402 of FIG. 4).

In various embodiments, the physiological acid-base model may be used in the context of prescribing therapeutic interventions and for precision and predictive medicine. Accordingly, the physiological acid-base model may operate to accurately and verifiably describes clinically observed pathophysiological conditions, for example, both in terms of serum pH and secondary physiologic compensatory responses. To that effect, the physiological acid-base model may be used to simulate normal physiological condition, and pathophysiological disorders, for example: (i) respiratory acidosis, (ii) respiratory alkalosis, (iii) metabolic acidosis, and (iv) metabolic alkalosis (the acid-base disorders).

Figure 5A:
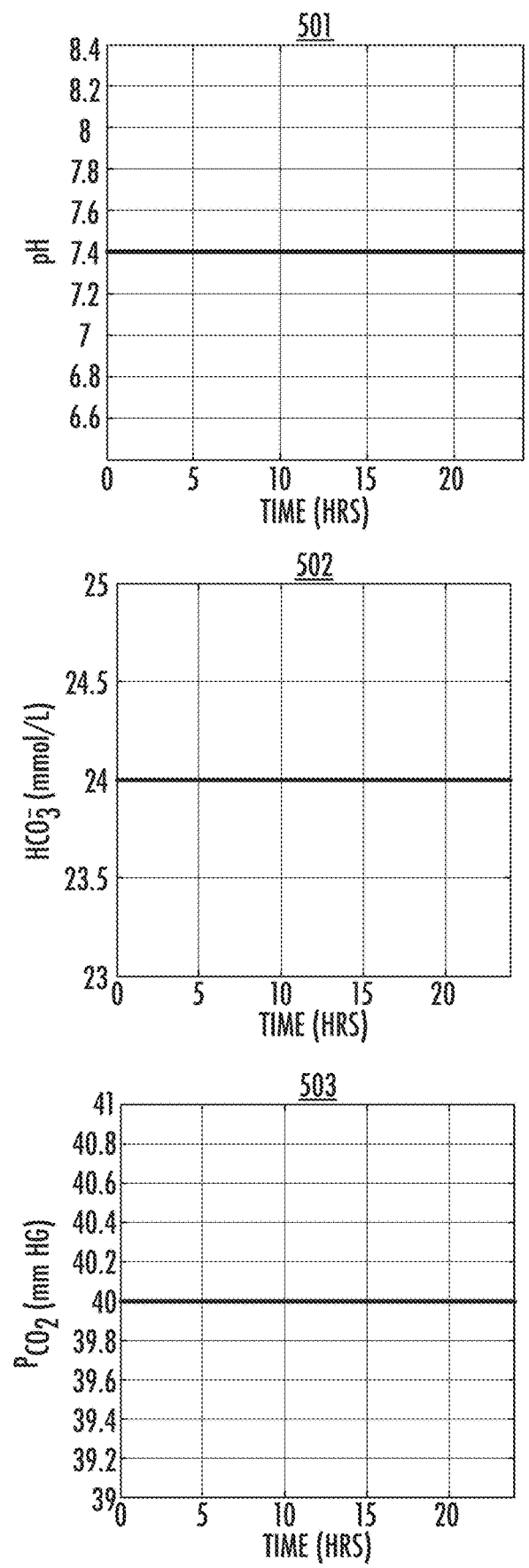
FIG. 5A illustrates results of a simulation of the physiological acid-base model under normal conditions according to some embodiments.

In the normal physiological state, the normal range of $HCO_3^-$ is 24±2 mmol/L, and the range for $pCO_2$ is 40±2 mm Hg, resulting in a normal pH range of 7.40±0.02. FIG. 5A depicts results (for example, acid-base information or predicted patient information) of simulation of the physiological acid-base model under normal conditions. As shown in graphs 501-503 of FIG. 5A, under normal physiological conditions, the blood pH is set to the steady state value of 7.4, with a $pCO_2$ value of 40 mmHg and $HCO_3^-$ of 24 mmol/L.

To simulate acid-base disorders (i)-(iv), various parameter values may be altered, for example, to disequilibrate $pCO_2$ and $HCO_3^-$ either individually or jointly, thereby changing the value of pH. In particular, creating an imbalance between body (for instance, mitochondrial) $CO_2$ production and pulmonary $CO_2$ excretion may result in changes in $pCO_2$, while disturbing $H^+$ production and renal $HCO_3^-$ generation and $HCO_3^-$ reclamation/$H^+$ excretion may affect $HCO_3^-$ levels In metabolic acidosis, the rate of renal generation of $HCO_3^-$ fails to equate the rate of the exogenous and/or endogenous $H^+$ production, often caused by an increased influx of $H^+$ (through exogenous and/or endogenous means such as intoxication or ketoacidosis), a decreased renal $HCO_3^-$ generation (for example, renal failure) or excessive loss of renal (for example, proximal tubular acidosis) or gastrointestinal (for example, diarrhea) absorptive capabilities.

Figure 5B:
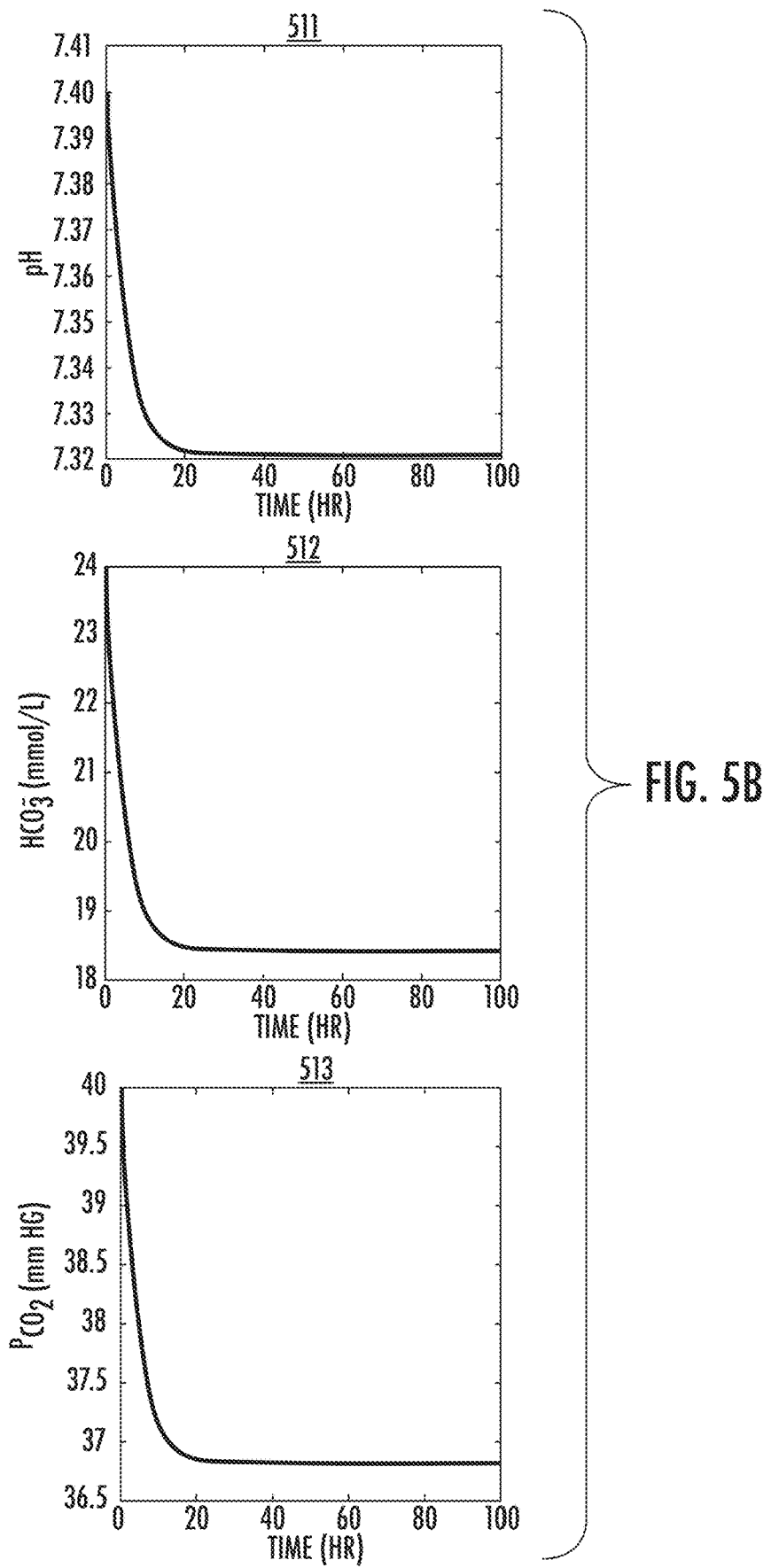
FIG. 5B illustrates results of a simulation of the physiological acid-base model under metabolic acidosis conditions according to some embodiments.

FIG. 5B depicts results (for example, acid-base information or predicted patient information) of simulation of the physiological acid-base model under metabolic acidosis conditions. As shown in graphs 511-513 of FIG. 5B, as the bicarbonate concentration drops, the $pCO_2$ level may decrease and reach a new equilibrium. This may be due to, as a secondary compensatory response, the respiratory center being stimulated to increase alveolar ventilation, creating a rate differential between mitochondrial production and pulmonary excretion of $CO_2$. In the dynamics observed in graphs 511-513, the cause of metabolic acidosis may be due to modeled diseases such as CKD and distal renal tubular acidosis. In metabolic alkalosis, the disorder is caused by an increased influx of $HCO_3^-$ into the extracellular fluid due to the inability of the kidney to excrete excess $HCO_3^-$ as a result of either decreased GFR as in volume depleted patients or an increased rate of renal absorption of $HCO_3^-$ (for example, enhanced renal tubular $HCO_3$ reclamation).

Figure 5C:
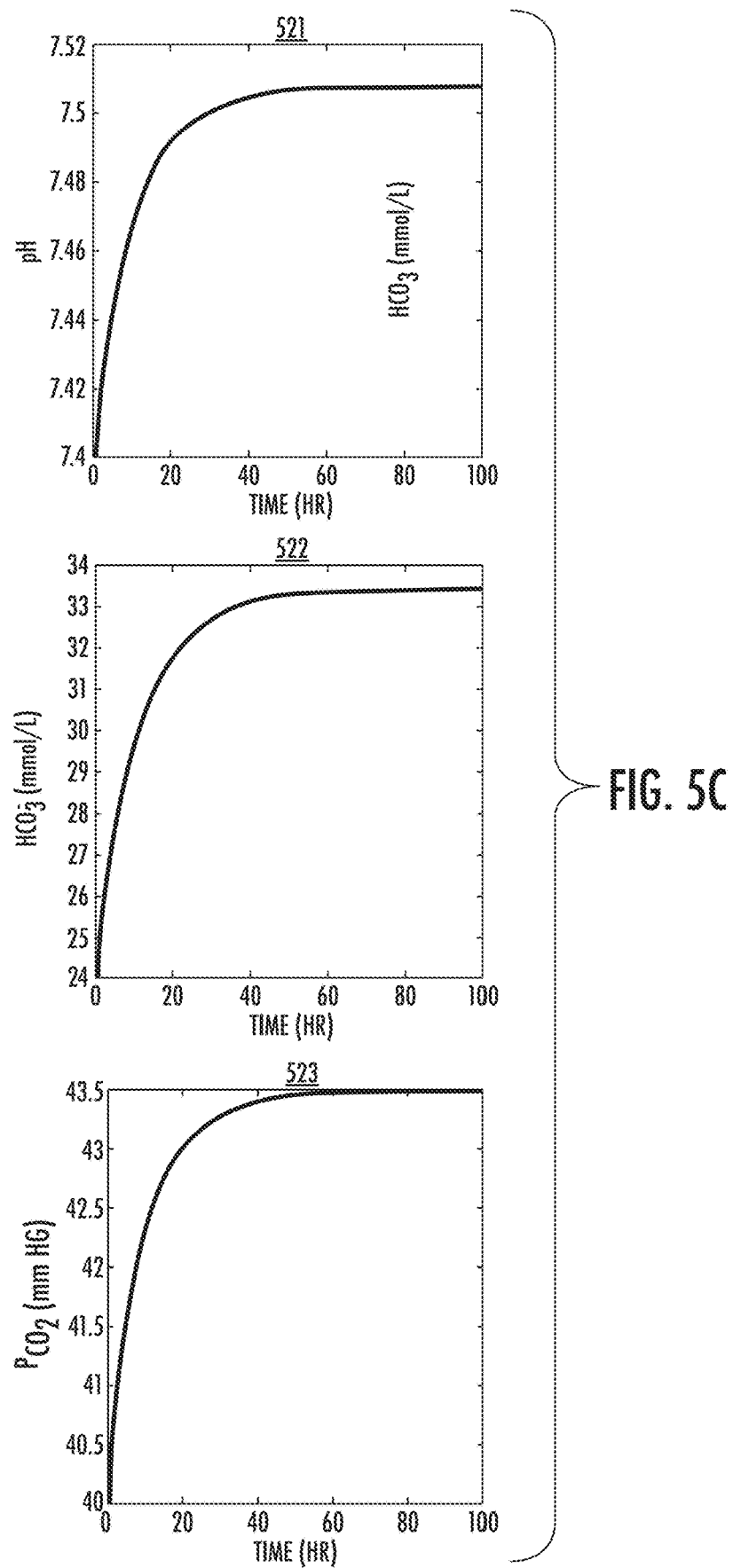
FIG. 5C illustrates results of a simulation of the physiological acid-base model under metabolic alkalosis conditions according to some embodiments.

The inability to reabsorb $HCO_3^-$ may contribute to an increase in blood $HCO_3^-$. FIG. 5C depicts results (for example, acid-base information or predicted patient information) of simulation of the physiological acid-base model under metabolic alkalosis conditions. For example, graphs 521-523 may illustrate the temporal behavior of the physiological acid-base model in metabolic alkalosis, where pH level increases as a consequence of increased serum $HCO_3^-$ and $pCO_2$ as a secondary compensatory respiratory response induced by hypoventilation. As shown in FIGS. 5B and 5C, each of acid-base disorders (i) and (ii) (the metabolic disorders) may equilibrate at different timescales. These observations are consistent with empirical studies where the compensatory responses take 12-24 hours for metabolic acidosis (see, for example, FIG. 5B), and approximately 24-72 hours for metabolic alkalosis (see, for example, FIG. 5C).

In some embodiments, the physiological acid-base model may operate to simulate respiratory disorders (iii) and (iv) by altering pulmonary excretion of $CO_2$ (for example, hyper- or hypoventilation, where $CO_2$ production and removal are changed). Simulations of (iii) and (iv) provide results that changes in $CO_2$ induce clinically expected alterations in $HCO_3$ and $H^+$, before the effect of secondary renal compensatory responses affect the level of reabsorbed $HCO_3^-$ and restore pH to normal range.

Figure 5D:
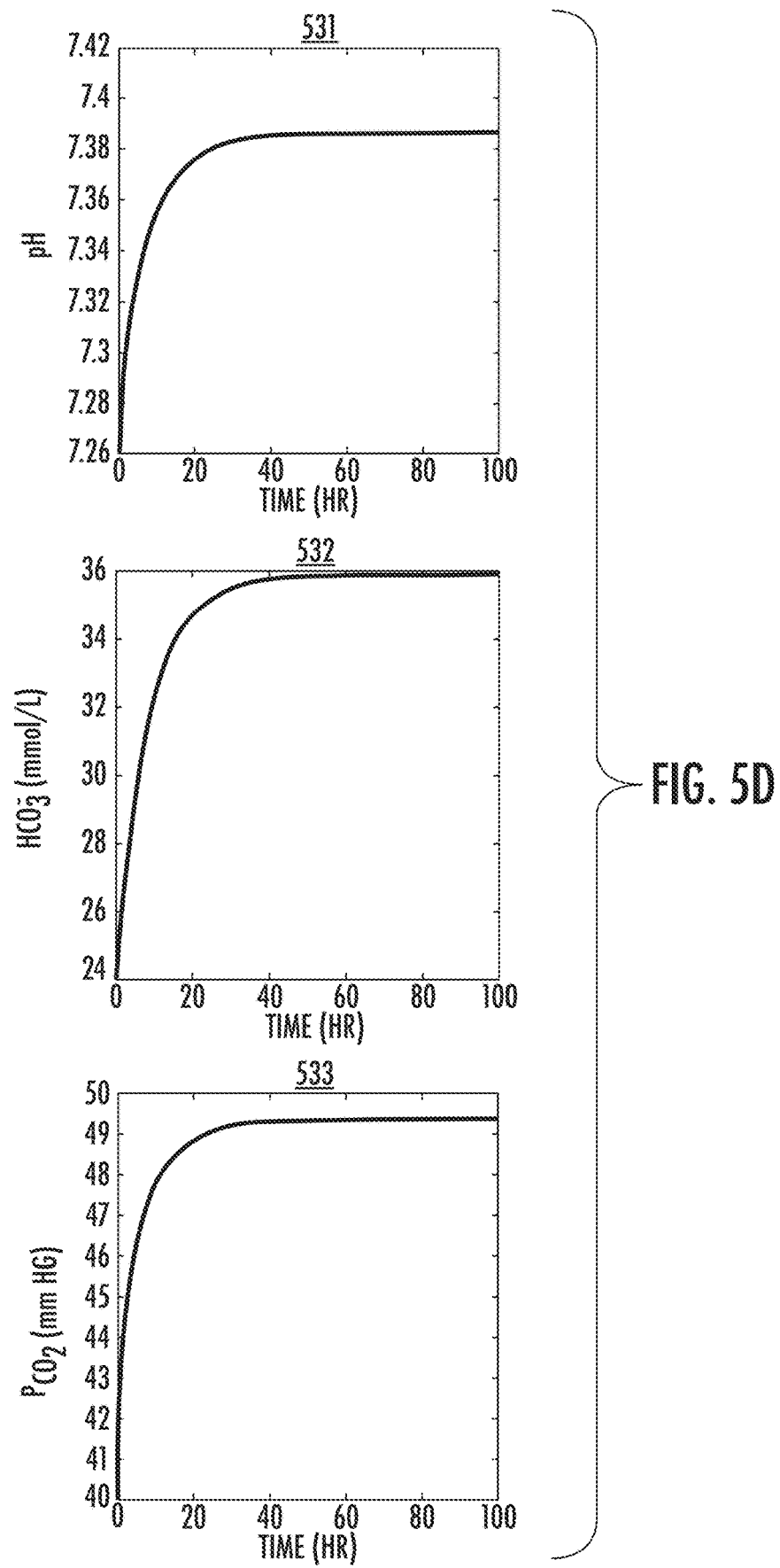
FIG. 5D illustrates results of a simulation of the physiological acid-base model under respiratory acidosis conditions according to some embodiments.
Figure 5E:
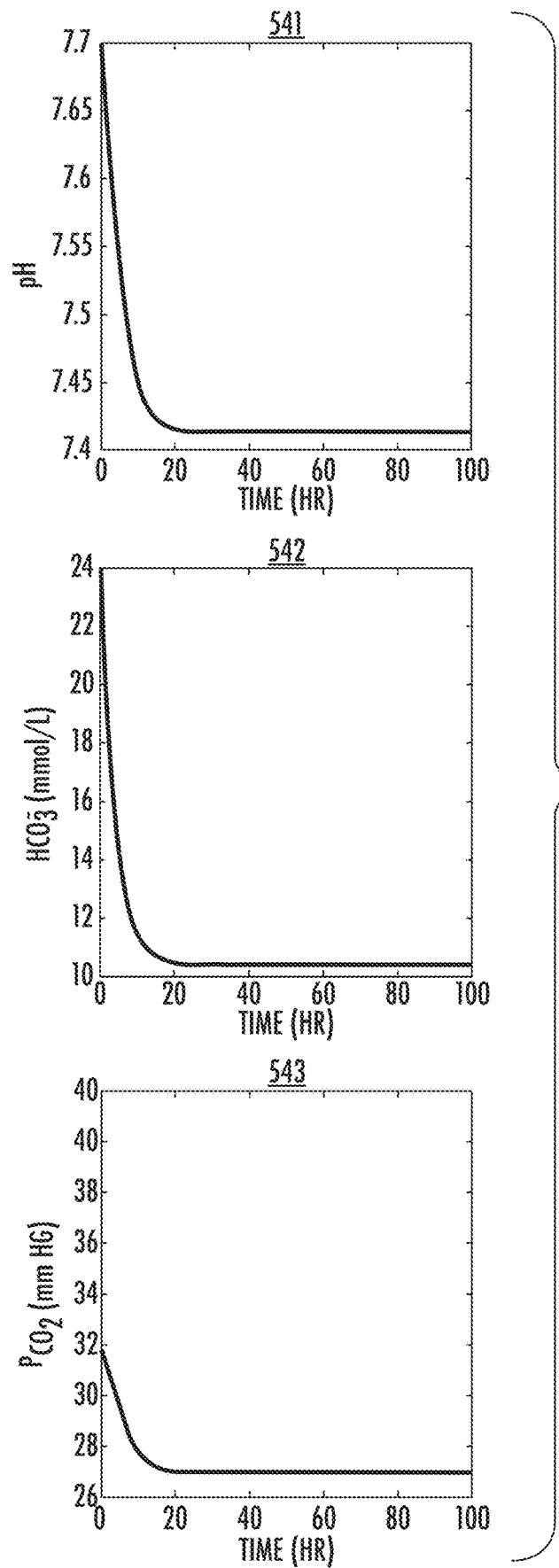
FIG. 5E illustrates results of a simulation of the physiological acid-base model under respiratory alkalosis conditions according to some embodiments.

FIG. 5D depicts results (for example, acid-base information or predicted patient information) of simulation of the physiological acid-base model under respiratory acidosis conditions and FIG. 5E depicts results (for example, acid-base information or predicted patient information) of simulation of the physiological acid-base model under respiratory alkalosis conditions. As shown in graphs 531-533 of FIG. 5D, during respiratory acidosis, pH level decreases initially before renal mechanism restores pH homeostasis to a value close to 7.4. Referring to graphs 541-543 of FIG. 5E, for respiratory alkalosis, the trajectory is reversed, where pH level increases before decreasing to a level above pH=7.4 while both $pCO_2$ and $HCO_3^-$ decreases. Historical information and clinical studies indicate that the timescale of renal compensation to equilibrate pH level is within 1-2 days in the case of respiratory alkalosis and 2-3 days in the case of respiratory acidosis. In addition, $pCO_2$ is inversely proportional to alveolar ventilation. Moreover, the steady-state values of the secondary compensatory responses predicted by the primary disturbances in both metabolic and respiratory disorders (i)-(iv) are in good agreement with clinical studies examining these disorders.

As indicated in FIGS. 5A-5E, the physiological acid-base model qualitatively predicts clinical observations (for example, determined as acid-base information or predicted patient information), at least in terms of pH, the directionality of primary disturbances and secondary compensatory responses, and timescales. To quantitatively compare the results of the model to that of clinical data on acid-base disorders, multiple types of disturbances may be generated by altering relevant parameters to induce metabolic and respiratory disorders, and to track the steady-state values of the state variables in order to compare them with clinically observed values.

FIG. 6A depicts physiological acid-base model validation results under metabolic acidosis conditions. In FIG. 6A, graph 601 depicts empirical clinical data described in Bushinsky et al., "Arterial PCO2 in Chronic Metabolic Acidosis," Kidney International, Vol. 22(3), pp. 311-314 (1982) ("Bushinsky"). Graph 601 shows the empirical serum $HCO_3^-$ value with respect to $pCO_2$ level as a result of secondary respiratory compensation, where each data point corresponds to a single patient with metabolic acidosis due to acetazolamide-induced (23 patients), $NH_4Cl$-induced (40 patients), renal tubular (48 patients), uremic (113 patients), and mixed (118 patients) acidosis. Graph 602 shows similar results of physiological acid-base model steady-state values for those involved exhibiting metabolic acidosis, where $H^+$ production and buffering, and renal filtration terms and $HCO_3^-$ depletion are uniformly randomly generated.

As indicated by graphs 601 and 602, the simulated serum $HCO_3^-$ with respect to $pCO_2$ (secondary respiratory compensation) is within the 95% confidence interval 610 of the clinical data. Line 611 represents a plot of the Winters Equation of Albert et al., "Quantitative Displacement of Acid-Base Equilibrium in Metabolic Acidosis," Annals of Internal Medicine, Vol. 66(2), pp. 312-322 (1967)," line 612 represents the Bushinsky Equation from Bushinsky, and line 613 represents a linear regression line fit to the clinical data. Simulation of the physiological acid-base model generated results within a 95% confidence interval of the empirical data observed by Bushinsky.

Figure 6B:
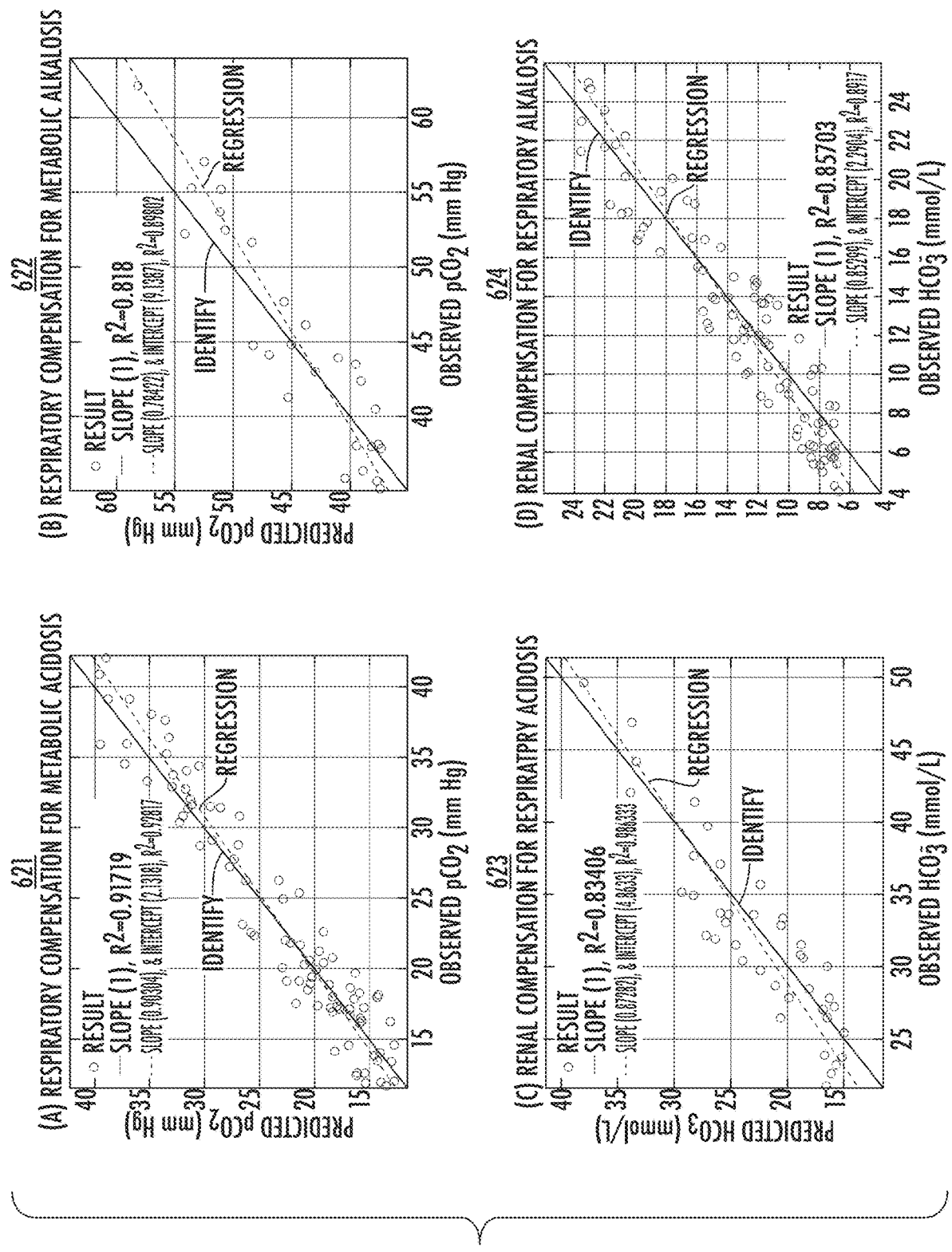
FIG. 6B illustrates physiological acid-base model validation results for the acid-base disorders according to some embodiments.

FIG. 6B depicts physiological acid-base model validation results for the acid-base disorders. More specifically, FIG. 6B shows graphs 621-624 depicting comparisons of physiological acid-base model in silico secondary compensatory responses to that of clinically observed secondary compensatory responses in metabolic acidosis (graph 621), and metabolic alkalosis (graph 622), respiratory alkalosis (graph 623), and respiratory acidosis (graph 624). FIG. 7 depicts a table of linear equation information for secondary compensatory responses for acid-base disorders according to some embodiments. In FIG. 7, table 702 depicts equations and values for linear equations of the form y=b+mx according to some embodiments.

Comparing the secondary respiratory compensation predicted by the physiological acid-base model with that of the observed clinical values (for example, as computed from the empirical equation in table 702 of FIG. 7), a linear relationship was obtained. Referring to FIG. 6B, the linear relationship included a regression line with a slope of 0.903 and intercept of 2.13, has an $R^2=0.928$ as compared to identity line with $R^2=0.917$ (see, for example, graph 621).

Similarly, for metabolic alkalosis, the physiological acid-base model according to some embodiments provides a predictable relationship between the primary metabolic disturbance of excess $HCO_3^-$ and the corresponding secondary respiratory compensation. Taking the $HCO_3^-$ values predicted by the physiological acid-base model and calculating the clinically expected $pCO_2$ values from table 702 of FIG. 7, the results may be compared with the predicted $pCO_2$ values from the physiological acid-base model. The predicted and the expected secondary compensations are in good agreement with expected results (see, for example, graph 622). As in graph 621, most of the points in graph 622 are on the identity line with a $R^2=0.818$, while the regression line has a slope of 0.7842 and intercept of 9.139, with $R^2=0.898$, which implies that the predicted and the expected secondary respiratory compensation to metabolic alkalosis are very similar.

Parallel observations are made in the case of respiratory disorders (see, for example, graphs 623 and 624). As shown in FIG. 6B, there is clearly a linear correlation between the simulation results of the physiological acid-base model and the expected observations. For example, for respiratory acidosis, the identity line has $R^2=0.8341$ whereas the regression line has $R^2=0.8633$ with the slope of 0.873 and intercept of 4.863 (graph 623), and for respiratory alkalosis, the identity line has $R^2=0.8570$ whereas the regression line has $R^2=0.8917$ with the slope of 0.853 and intercept of 2.290 (graph 624). Accordingly, in all of the quantitative validations for the acid-base disorders, the physiological acid-base model accurately and effectively predicted the secondary responses to the primary disturbances of the acid-base disorders.

In some embodiments, a quantification process may operate to quantify the levels of uncertainty and sensitivity of physiological acid-base model output of Equations (2)-(4). In some embodiments, the quantification process may characterize the level of uncertainty each of the model parameters exhibits. Latin hypercube sampling (LHS) (for example, with 10,000 uniformly distributed samples) may be used to quantify the uncertainties associated with the parameter values and their effects on the in-silico results. In conjunction with the uncertainty quantification, the quantification process may use partial rank correlation coefficient (PRCC) to quantitate the impact of sensitivity of all the state variables to each of the model parameters.

FIG. 8 illustrates parameter descriptions and values for a quantification process according to some embodiments. Table 802 of FIG. 8 provides the results of the sensitivity analysis with sensitivity coefficients (PRCC values). In table 802, The results are all significant with p<0:001 (except: (p=0.004246) and (p=0.004299)); the symbol "--" denotes the parameters used to induce different metabolic disorders (for example, set to zero or otherwise reduced, eliminated, or disabled).

Figure 9A:
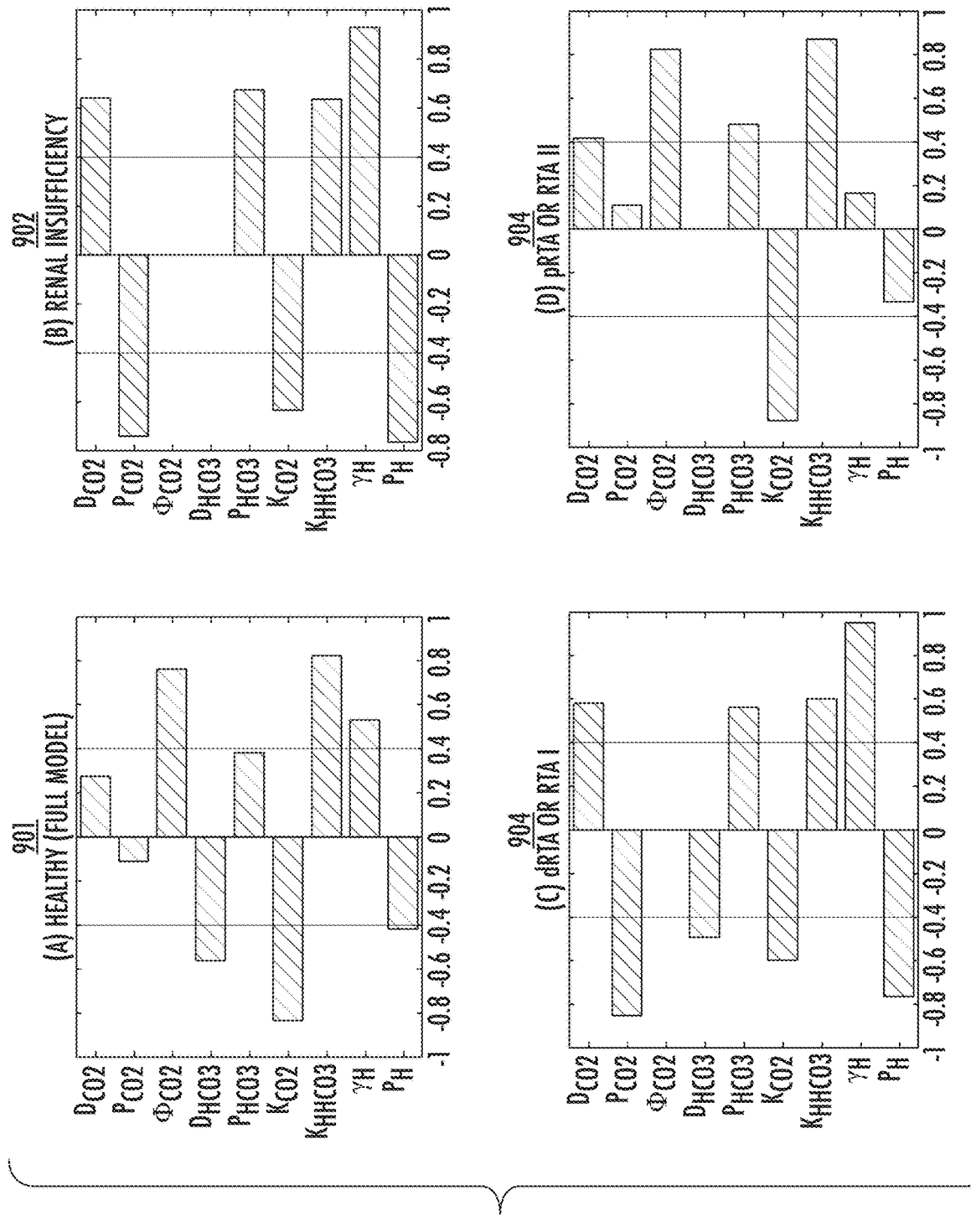
FIGS. 9A-9C illustrate results of a quantification process sensitivity analysis according to some embodiments.
Figure 9B:
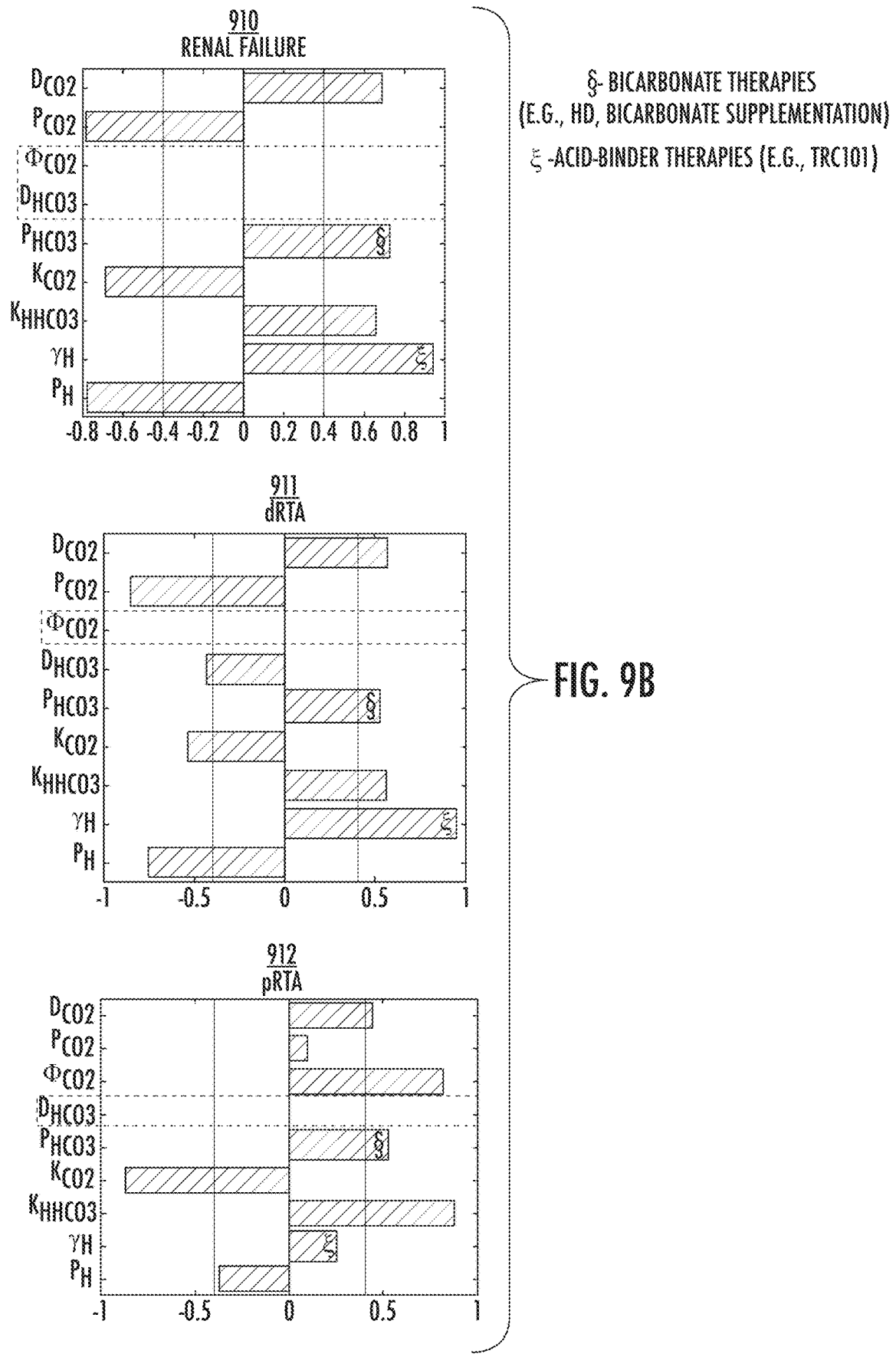
Figure 9C:
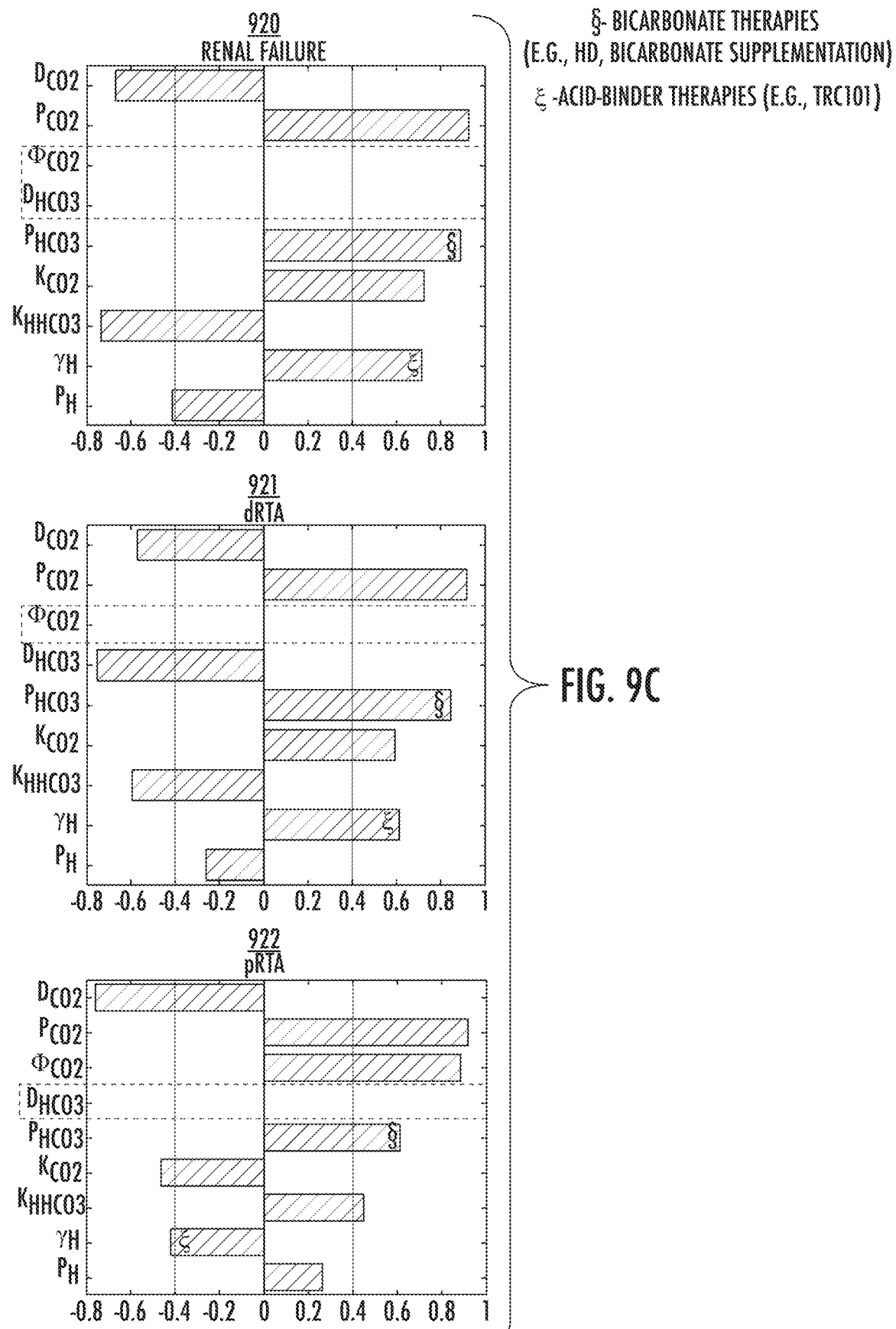

FIGS. 9A-9C illustrates results of a quantification process sensitivity analysis according to some embodiments. For the results depicted in FIG. 9A, sensitivity analyses with respect to steady-state values of pH were for normal physiological condition, and for metabolic acidosis as a result of renal insufficiency, proximal, and distal tubular acidosis.

For healthy individuals, graph 901 shows that the predominant (or primary) parameters affecting pH are those involving renal function (acid secretion rate ($\phi_{CO_2}$) and $HCO_3^-$ reabsorption rate ($D_{HCO_3^-}$)), $HCO_3^-$ therapy ($J_{HCO_3^-}$), reaction rates or $pK_a$ of the buffer system, production ($P_H$) and removal or non-bicarbonate buffering of protons ($\gamma_H$). Therapies targeting these primary parameters may have a strong effect on correcting pH disturbances, where the sign of the correlation indicates the directionality of therapeutic targets. That is, since acid secretion rate, $\phi_{CO_2}$, bicarbonate therapy, $J_{HCO_3^-}$, forward reaction (hydration) rate, $K_{H^+,HCO_3^-}$, and removal or non-bicarbonate buffering of protons $\gamma_H$ are positively correlated with respect to pH levels, therapeutic interventions increasing these parameters should increase pH level. For example, $HCO_3^-$ supplementation or usage of acid-binders will increase serum pH. Similarly, due to negative correlation, therapeutic intervention decreasing $HCO_3^-$ reabsorption rate ($D_{HCO_3^-}$), backward (dehydration) reaction rate and hydrogen body production, $P_H$, will also increase pH.

For individuals with metabolic acidosis, correcting acidosis requires correcting the pH level to near normal. Sensitivity analysis, as shown in graph 902 suggests that, for metabolic acidosis due to renal insufficiency or failure (RF), targeting primary parameters, such as increasing respiratory $CO_2$ removal ($D_{CO_2}$), $HCO_3^-$ supplementation or therapy ($P_{HCO_3^-}$, for example, $NaHCO_3$ or HD), hydration reaction rate ($K_{H^+,HCO_3^-}$), and/or removal of excess protons (for example, through acid-binder supplementation) may be effective. Alternatively, similar correction of pH can be achieved by decreasing body production of $CO_2$ ($P_{CO_2}$), dehydration reaction rate ($K_{CO_2}$), and/or body production of acid (for example, through dietary restriction of protein-rich diets).

Referring to graph 903, for distal or Type I renal tubular acidosis (dRTA or RTA-I), the directionality of most of the primary (sensitive or predominant) parameters shown in the case of RF are also observed in the case of RTA type II or proximal tubular (pRTA or RTA-II, see, for example, graph 904). In addition, decreasing $HCO_3^-$ renal reabsorption ($D_{HCO_3^-}$) can help increase the $HCO_3^-$ level of pH to normal. Unlike RTA-I, the set of primary parameters may be different in the case of RTA-II. For instance, graph 904 shows that, increasing ventilation rate ($D_{CO_2}$), acid secretion rate ($\phi_{CO_2}$), $HCO_3^-$ supplementation or therapy ($J_{HCO_3^-}$), and/or hydration reaction rate ($K_{H^+,HCO_3^-}$), or decreasing dehydration reaction rate ($K_{CO_2}$) can increase the level pH and thereby correct metabolic disorder.

In the case of RTA-II, body production of $CO_2$ may not be effective in correcting pH levels as observed in the case of RTA-I. In all of the analyses, the reaction rates may be important and can strongly change the effect of the buffer since they determine the $pK_a$ value of the system. The sensitivity analysis suggests that altering (for example, as indicated by a treatment recommendation) the primary parameters according to some embodiments under different induced acidemia may help increase the pH, and therapeutic strategies for some of the disorders may be different depending on the particular pathophysiology.

FIGS. 9B and 9C further illustrate sensitivities for therapeutic targets for various acid-base disorders. For example, FIG. 9B depicts graphs 910-912 for bicarbonate therapies (for example, HD, bicarbonate supplementation) and acid-binder therapies (for example, TRC 101) for correcting pH. FIG. 9B depicts graphs 920-922 for bicarbonate therapies and acid-binder therapies for correcting $HCO_3^-$. As highlighted in graphs 910 and 920, a renal failure condition may be generated by setting the acid secretion rate and the renal filtration rate to zero; as highlighted in graphs 911 and 921, a dRTA condition may be generated via setting the acid secretion rate to zero; and as highlighted in graphs 912 and 922, a pRTA condition may be generated via setting the renal filtration rate to zero.

In some embodiments, acid-base models may include intradialytic-based models, which may demonstrate, determine, predict, or otherwise process acid-base homeostasis conditions, including acid-base disorders. Metabolic acidosis is one of the many sequelae associated with the progression of CKD and/or end-stage renal disease (ESRD), and involves a lack of acid-base homeostasis, resulting in bicarbonate depletion with acid retention. This condition may lead to adverse consequences such as increased protein and bone catabolism and impaired cardiac contractility, worsening of CKD-mineral bone disorder (BMD), and increased morbidity and mortality. In hemodialysis HD patients, HD is used to restore acid-base homeostasis by transferring $HCO_3^-$ from the dialysate into the patient, thereby working to correct metabolic acidosis.

Some embodiments may include intradialytic acid-base models of patient's physiologic regulation of the $HCO_3^-/CO_2$ buffering system with Henderson-Hasselbalch mass-action kinetics, endogenous production of both $CO_2$ and $H^+$, non-bicarbonate buffering, and respiratory regulation to simulate the systemic effects of intradialytic correction, for example, of metabolic acidosis. In various embodiments, the intradialytic acid-base models may include a dialysis patient model and a dialyzer model. In some embodiments, the dialysis patient model may be coupled with a spatiotemporal model dialyzer to quantitate intradialytic dynamics of $HCO_3^-$ and $H^+$ (see, for example, FIG. 10). The intradialytic acid-base models may be validated by, inter alia, comparing its predictions to clinical observations of intradialytic acid-base dynamics in a patient population. As described in more detail in this Detailed Description, the intradialytic acid-base models may operate to accurately predict clinical observations of intradialytic serum $HCO_3^-$, $pCO_2$, and/or pH. The intradialytic acid-base models may operate to characterize the differential contributions of the constituents of acid-base homeostasis, and provide for determinations of contributions, which may be variable and/or depend on patient-specific characteristics, such as buffer capacity, apparent $HCO_3^-$ space, and parameters describing relevant physiologic regulatory mechanisms.

The maintenance of acid-base homeostasis is one of the main functions of the kidney, and acid-base homeostasis is also important in cellular processes. In CKD and ESRD patients, the ability of the kidney to maintain this homeostatic function is impaired, resulting in acid-base disorders, such as metabolic acidosis. In general, metabolic acidosis is characterized by either bicarbonate renal or gastrointestinal absorptive and/or secretive defects, which is affected by changes in bicarbonate as a result of an inequality between accumulated metabolic production of acid and hydrogen ions, and renal bicarbonate reabsorption. Metabolic acidosis results in bicarbonate depletion with acid retention, leading to a concatenation of adverse consequences such as increased protein and skeletal muscle catabolism, bone demineralization, impaired cardiac contractility, further CKD progression, worsening of CKD-BMD, growth and thyroid hormone abnormalities, soft-tissue and vascular calcification, insulin resistance, $\beta_2$-microglobulin accumulation, and increased morbidity, hospitalization, and/or mortality. Thus, correcting metabolic acidosis is necessary for adequate management of the multisystemic complications associated with CKD/ESRD.

Several small-scale prospective interventional and observational clinical studies have found that correcting metabolic acidosis with alkali therapy preserves kidney, bone and muscle health, in which it was shown that, for instance, sodium bicarbonate may increase muscle mass, preserve renal function, and improve vascular endothelial functions, insulin sensitivity, parathyroid gland sensitivity to calcium. Clinical guidelines suggest treating metabolic acidosis in CKD patients with alkali therapy for serum bicarbonate level less than 22 mEq/L. Patients can be treated with oral sodium bicarbonate, acid-binders (e.g., veverimer, formerly known as TRC101), hemodialysis bicarbonate dialysate, and/or by means of dietary modification restricting overconsumption of acidogenic diets.

Most CKD/ESRD patients depend on HD to maintain level of serum electrolytes and correct acid-base abnormalities. In HD patients, HD is a common modality used to restore acid-base homeostasis by providing base from the dialysate to neutralize acids endogenously produced during the interdialytic periods in the patients, thereby correcting metabolic acidosis. However, during dialysis, CKD/ESRD patients are subjected to a sharp dialytic influx of bicarbonate $HCO_3^-$, frequently resulting in metabolic alkalosis. If dialysate $HCO_3^-$ concentration is not properly prescribed, the rapid acid-base shift may result in adverse consequences with multi-systemic effects such as an abrupt fall in ionized calcium, diminishing diaphragmatic respiratory drive via pH-mediated peripheral chemosensory pathway, increased potassium removal and calcium phosphate precipitation, arrhythmia and hemodynamic instability.

Several studies have shown differential responses to a large intradialytic influx of dialysate bicarbonate, where patients with subclinical metabolic acidosis experience carbon dioxide mediated ventilatory stimulation, while those with pronounced clinical metabolic acidosis exhibit dominant inhibitory respiratory drive. In addition, observational studies have also shown that high serum bicarbonate was associated with subclinical cardiovascular diseases and hearth failure and/or increased arterial calcifications. Therefore, it is paramount that intradialytic bicarbonate concentration be properly prescribed to correct metabolic acidosis without large swings in serum bicarbonate. Accordingly, intradialytic acid-base models according to some embodiments may operate to simulate the physiological regulation of the $HCO_3^-/CO_2$ buffering system that may allow for treatment recommendations, such as prescribing the precise intradialytic bicarbonate concentration needed to correct metabolic acidosis without generating metabolic alkalosis.

Conventional models describing acid-base homeostasis in different systems and during hemodialysis have been deficient because, inter alia, they did not incorporate other constituents of the bicarbonate buffering system. In addition, conventional modelling systems focus on exchange processes between patients and dialyzer, neglecting to incorporate the physiological regulation of these electrolytes and solutes.

The physiological acid-base model according to some embodiments may provide a physiologically-based modeling structure for determining aspects of acid-base homeostasis under normal physiologic conditions and acid-base disorders, and provide for the investigation into the effects of pathophysiologic acid-base perturbations on the acid-base status. In some embodiments, the intradialytic acid-base model may be an extension of the physiological acid-base model extended to, among other things, investigate the intradialytic dynamics of a bicarbonate buffering system.

HD patients are heterogenous due to a multitude of factors and a single one-size-fits-all prescription may not be beneficial. Aiming for the optimal hemodialysis bicarbonate prescription to correct metabolic acidosis without generating alkalosis requires a sound quantitative understanding of physiologic regulation of acid-base homeostasis during HD, for the prescription of optimal pre- and post-dialysis serum bicarbonate level cannot be attained using a standard procedure for all patients as acid production rate, apparent bicarbonate space, ultrafiltration rate, and/or other relevant factors vary from patient to patient.

Accordingly, intradialytic acid-base models are built on the physiological acid-base models according to some embodiments. Certain embodiments incorporate physiologically-based models that simulate the physiological regulation of $HCO_3^-/CO_2$ buffering system with Henderson-Hasselbalch mass-action kinetics, endogenous production of both $CO_2$ and $H^+$, non-bicarbonate buffering, and renal and respiratory regulation. The intradialytic acid-base models may include a dialysis patient model to be applied to HD patients where the renal regulation is impaired and is replaced by dialysis. In addition, the dialysis patient model may be associated with a dialyzer model to simulate intradialytic dynamics. In some embodiments, the dialyzer model may include, may be the same or substantially the same as, or may be an adaptation of the dialyzer model described in Maheshwari et al., "An In Silico Method to Predict Net Calcium Transfer During Hemodialysis," 2017 39th Annual International Conference of the IEEE Engineering in Medicine and Biology Society (EMBC), pp. 2740-2743 (2017). In some embodiments, the intradialytic acid-base models may be calibrated using historical patient data, and model predictions generated by the intradialytic acid-base models may be used to provide insights into the intradialytic acid-base dynamics that are not attainable using conventional techniques and models.

Figure 10:
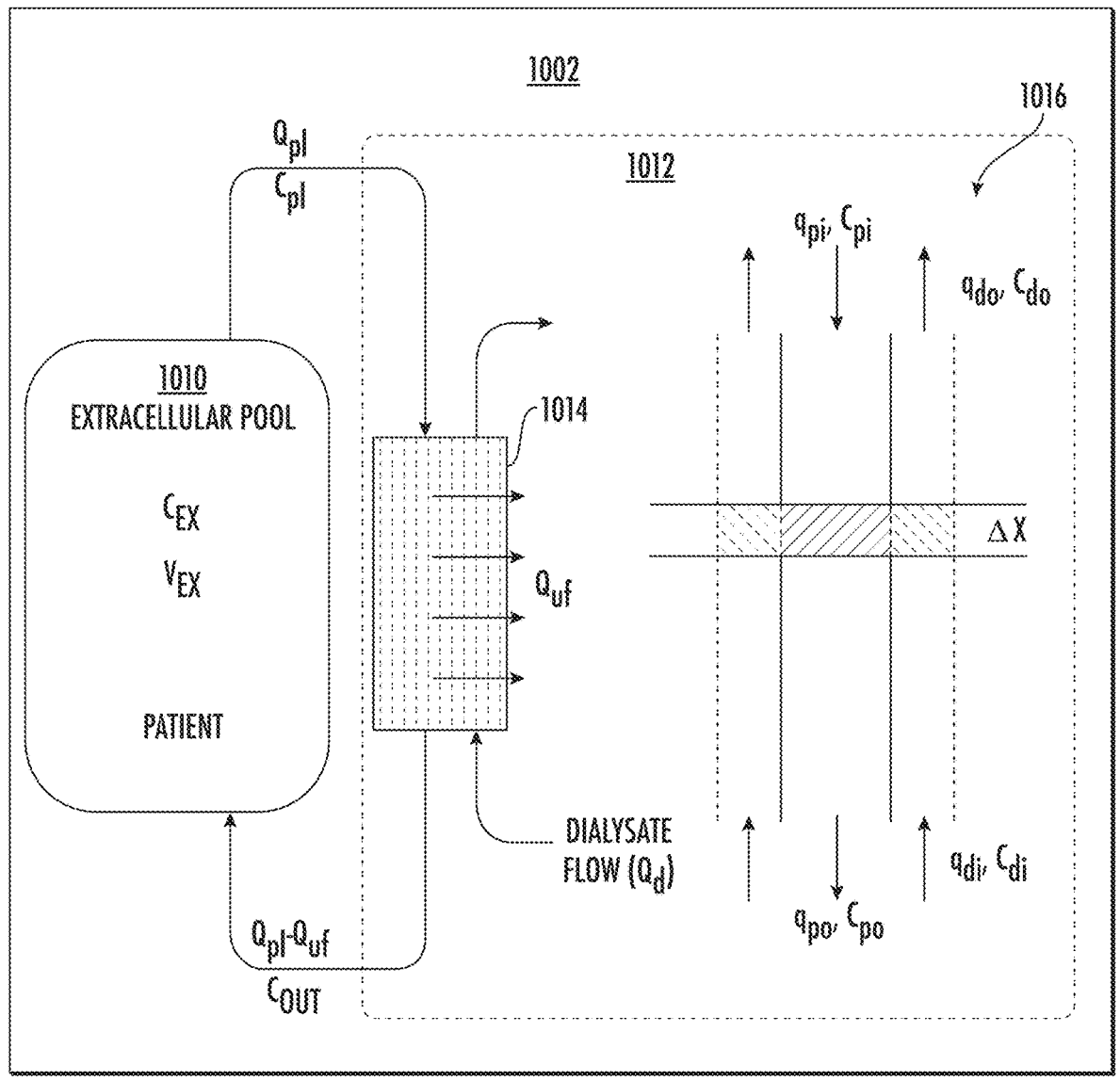
FIG. 10 illustrates a block diagram of an intradialytic acid-base model according to some embodiments.

FIG. 10 illustrates a block diagram of an intradialytic acid-base model according to some embodiments. As shown in FIG. 10, an intradialytic acid-base model 1002 may include a dialysis patient model or compartment 1010 and a dialyzer model or compartment 1012 having a dialyzer 1014. In various embodiments, patient compartment 1010 may include the distribution volume ($V_{ex}$) and concentrations of acid-base variables (for example, $C_{ex}=\{C_{H^+}, C_{HCO_3^-}, C_{CO_2}\}$). In some embodiments, $Q_p$, $Q_d$, and $Q_{uf}$ are the plasma flow rate, dialysate flow rate, and ultrafiltration rate, respectively. A single dialyzer fiber 1016 may depict the counter-current flows interaction between blood and dialysate flows in dialyzer 1014, in which there is an intradialytic transfer between blood and dialysate through the infinitesimal fiber segment $\Delta x$. The subscripts for q and C denote plasma (pl) or extracellular fluid (ex), dialyzer input (di) and output (do), dialyzer blood inlet (pi), and outlet (out).

For the dialysis patient model, some embodiments may use a physiologically-based dynamic model describing the regulation of $HCO_3^-/CO_2$ buffering system with Henderson-Hasselbalch mass-action kinetics, in which we incorporate the endogenous production of both $CO_2$ and $H^+$, non-bicarbonate buffering, and the physiologic regulation of the $HCO_3^-/CO_2$ buffering system through ventilation and renal excretion. Although there are other buffer systems, some embodiments may focus mainly on the $HCO_3^-/CO_2$ buffering system, which is the most abundance and effective buffer system in the body. Under physiologic conditions, pH is regulated mainly by chemical acid-base buffering, respiratory control and renal glomerular filtration. The chemical acid-base buffering is modeled using Henderson-Hasselbalch mass-action kinetics, in which, in some embodiments, the action of carbonic anhydrase is fast, and $K_{H^+,HCO_3^-}$ and $K_{CO_2}$ association and disassociate rates, respectively.

During normal cellular metabolic activities, $CO_2$ and $H^+$ are produced as by-products; this endogenous production is captured by $P_{CO_2}$ and $P_{H^+}$ for $CO_2$ and $H^+$, respectively. In addition, acid is mobilized or buffered with other non-bicarbonate buffers such as phosphate, and this is represented by $\gamma_{H^+}C_{H^+}$, where $\gamma_{H^+}$ is the mobilization or removal rate. In normal physiologic conditions, the kidney, the second regulatory organ, is responsible for regulating $HCO_3^-$ level by either secreting excess H+ into tubular lumen during metabolic acidosis, and/or excreting or reabsorbing $HCO_3^-$ in the proximal and distal segments of nephrons. Unlike the physiological acid-base model according to some embodiments, the dialysis patient model may not include (or may include lower functioning of) the renal regulation of $HCO_3^-$ and $H^+$ because the dialysis patient model is adapted to dialysis patients where the ability of excrete acid is impaired. As a result, in some embodiments, the dialysis patient model may assume that there is little or even no renal function. In some embodiments, the renal function is replaced by the use of the dialyzer (for example, by dialyzer fluxes) implemented via the dialyzer model. For example, the expressions $-Q_p C_{HCO_3^-}$ and $(Q_p-Q_{uf})C_{HCO_3^-,out}$ may account for bicarb flux from patient and post-dialyzer flux to patient, respectively, which is characterized by blood flow rate, $Q_p$, and ultrafiltrate rate, $Q_{uf}$. For the third regulatory mechanism, in order to regulate $CO_2$ removal, lung increases or decreases ventilation, which is triggered by the response of central and peripheral chemoreceptors to changes in $pCO_2$, and $D_{CO_2}V_0Y_{CO_2}$ describes removal of $CO_2$ through ventilation by lung characterized by blood volume, cardiac output, arteriovenous difference of $CO_2$. The parameters $D_{CO_2}$ and $V_0$ are ventilation rate and minute ventilation, respectively. In some embodiments, the dialysis patient model describing acid-base homeostasis may be according to the following Equations (7)-(9):

$$\frac{d(C_{H^+}V_{ex})}{dt} = \underbrace{P_{H^+}}_{\text{Endogenous } H^+ \text{ production}} - \underbrace{\gamma_{H^+}C_{H^+}}_{\text{Lumped non-bicarbonate}} - \underbrace{(K_{H^+,HCO_3^-}C_{H^+}C_{HCO_3^-} + K_{CO_2}C_{CO_2})V_{ex}}_{\text{Henderson-Hasselbach kinetics}}, \quad (7)$$

$$\frac{d(C_{HCO_3^-}V_{ex})}{dt} = \underbrace{-Q_p C_{HCO_3^-}}_{\text{Flux from patient}} + \underbrace{(Q_p - Q_{uf})C_{HCO_3^-,out}}_{\text{Post-dialyzer flux to patient}} - \underbrace{(K_{H^+,HCO_3^-}C_{H^+}C_{HCO_3^-} + K_{CO_2}C_{CO_2})V_{ex}}_{\text{Henderson-Hasselbach kinetics}}, \quad (8)$$

$$\frac{d(C_{CO_2}V_{ex})}{dt} = \underbrace{P_{CO_2}}_{\text{Endogenous } CO_2 \text{ production}} - \underbrace{D_{CO_2}V_0C_{CO_2}}_{\text{Respiratory ventilation}} + \underbrace{(K_{H^+,HCO_3^-}C_{H^+}C_{HCO_3^-} + K_{CO_2}C_{CO_2})V_{ex}}_{\text{Henderson-Hasselbach kinetics}}. \quad (9)$$

During dialysis, a patient loses a significant amount of fluid. This is assumed to occur at a constant ultrafiltration rate, $Q_{uf}$, and fluid removal by ultrafiltration occurs in proportion to the compartmental distribution volume. Accordingly, in some embodiments, extracellular fluid volume may be determined according to the following Equation (10):

$$\frac{dV_{ex}}{dt} = -\underbrace{Q_{uf}}_{\text{Ultrafiltration rate}}. \quad (10)$$

In some embodiments, the dialyzer model may include two spatial temporal models describing both blood and dialysate sides using hyperbolic partial differential equations. The concentration of $HCO_3^-$ in the blood side may be determined according to the following Equation (11):

$$\frac{\partial c_{HCO_3^-}}{\partial t} = -\underbrace{\frac{1}{N \cdot A}\frac{\partial(Q_p c_{HCO_3^-})}{\partial x}}_{\text{Axial convection}} + \underbrace{\frac{1}{N \cdot A}\frac{\partial Q_p}{\partial x}c_{HCO_3^-}(1-\sigma_{HCO_3^-})}_{\text{Radial convection}} - \quad (11)$$

-continued $$\underbrace{\frac{Pe}{e^{Pe}-1}\frac{1}{N\cdot A\cdot L}K_o A\left(c_{HCO_3^-}-\frac{c_{D,HCO_3^-}}{\beta}\right)}_{\text{Gibbs-Donnan corrected effective diffusion}},$$

where N is the number of fibers, A denotes fiber cross-sectional area, $$\sigma_{c_{HCO_3^-}}$$

represents the $HCO_3^-$ reflection coefficient, $$Pe = \frac{(1-\sigma_{c_{HCO_3^-}})Q_{uf}}{K_o A}$$

defines the Peclet, L is the fiber length, $K_o A$ is the effective membrane mass-transfer coefficient for $HCO_3^-$, $\beta$ is Gibbs-Donnan correction factor (i.e., a Gibbs-Donnan corrected dialyzer model). In some embodiments, $\beta$ and may be set to a constant value of 1.05 which corresponds to 5% of $HCO_3^-$. In various embodiments, for the dialyzer side, it may be assumed that the dialysate flow is uniform and equally shared by the N fibers present in the dialyzer housing. The hyperbolic partial differential equation describing the concentration within annulus dialysate flow boundary may have the form of the following Equation (12):

$$\frac{\partial c_{D,HCO_3^-}}{\partial t} = \underbrace{\frac{1}{N\cdot A_d}\frac{\partial(Q_d c_{D,HCO_3^-})}{\partial x}}_{\text{Axial convection}} - \underbrace{\frac{1}{N\cdot A_d}\frac{\partial Q_d}{\partial x}c_{HCO_3^-}(1-\sigma_{c_{HCO_3^-}})}_{\text{Radial convection}} + \underbrace{\frac{Pe}{e^{Pe}-1}\frac{1}{N\cdot A_d\cdot L}K_o A\left(c_{HCO_3^-}-\frac{c_{D,HCO_3^-}}{\beta}\right)}_{\text{Gibbs-Donnan corrected effective diffusion}}, \quad (12)$$

where $A_d$ circular cross-sectional area of annulus space for dialysate flow around a fiber. In various embodiments, plasma flow rate ($Q_p$) may decrease along the fiber length in the dialyzer due to ultrafiltration, the decrease may be linearly along the fiber length. In some embodiments, the dialysate flow rate may increase by the amount of fluid removed by ultrafiltration from the blood side to the dialysate side, resulting in counter-current kinetics. The spatial aspects of plasma and dialysate flow rates may be determined according to the following equations (13) and (14):

$$Q_p = Q_{pi} - \frac{x}{L}Q_{uf}, \quad (13)$$

$$Q_d = Q_{di} + \frac{(L-x)}{L}Q_{uf}, \quad (14)$$

where $Q_{pi}$ and $Q_{di}$ are initial plasma and dialysate flow rates.

In some embodiments, Equations (7)-(14) may constitute components of intradialytic acid-base models describing, simulating, predicting, or otherwise processing intradialytic acid-base dynamics. FIG. 11 illustrates table 1102 of intradialytic acid-base model parameters and values according to some embodiments.

Validation of Intradialytic Acid-Base Models

Intradialytic acid-base models according to some embodiments have been both qualitatively and quantitatively validated under the normal physiological condition and acid-base disorders, where the intradialytic acid-base models were able to accurately predict several observed clinical responses in terms of both pH and compensatory responses. In particular, validated observations included that changes in $CO_2$ alters $HCO_3^-$ and $H^+$ levels, before the renal compensation restores pH close to the normal physiological range by affecting the amount of reabsorbed $HCO_3^-$. Similar predictions were made in metabolic disturbances, in which pH never returns to the normal range due to ineffectiveness of respiratory compensation. In addition, comparison of clinical data of patients with chronic metabolic acidosis with the in silico prediction of the model yields $R^2$ values of 0.928 and 0.917 for linear regression line (with a slope of 0.903 and intercept of 2.13) and identity line (with a slope of 1 and zero intercept), respectively (see FIG. 6A, graph 602, and FIG. 6B, graph 621). As indicated by the validation information, acid-base models according to some embodiments may be used to investigate intradialytic acid-base balance, for example, to accurately predict HCO3, pCO2 and pH. The intradialytic acid-base models could be used as a tool to effectively prescribe $dHCO_3^-$ (for example, improper dialysate $HCO_3$ prescription may exacerbate an acid-base disorder or other imbalance) and to predict intradialytic acid-base dynamics before the next HD session. In addition, the intradialytic models could also provide insights into combination therapy where HD is combined with other pharmacologic treatments to maintain patients' acid-base homeostasis during and between HD sessions. Embodiments are not limited in this context.

To calibrate the dialysis patient model, a method of lines approach is employed to solve the model equations using stiff ode15s solver in MATLAB®, where the model is parameterized according to parameter values obtained from literature (see, for example, table 902 of FIG. 9), with the exception of endogenous $H^+$ and $CO_2$ production rates ($P_{H^+}$) and ($P_{CO_2}$), respectively, non-bicarbonate buffering rate ($\gamma_{H^+}$), and respiratory ventilation rate ($D_{CO_2}$). These parameters are estimated individually from patient-specific data. These parameters may be found for each patient by minimizing the weighted differences between the model quantities and data using the least-square cost function of Equation (15):

$$J(\Theta, \sigma_1^2, \sigma_2^2, \sigma_3^2) = \quad (15)$$

$$\omega_1\left(\frac{1}{\sigma_1^2}\sum_{j=1}^{T_2}|D_j^{(1)}-M_j^{(1)}|^2 + \frac{1}{\sigma_2^2}\sum_{j=1}^{T_2}|D_j^{(2)}-M_j^{(2)}|^2\right) +$$

$$\frac{\omega_2}{\sigma_3^2}\sum_{j=1}^{T_3}|D_j^{(3)}-M_j^{(3)}|^2.$$

In Equation (13), $\Theta=(P_{H^+}, P_{CO_2}, \gamma_{H^+}, D_{CO_2})$, and $D_j^{(k)}$ and $M_j^{(k)}$ denote clinical data and model observation, respective, with k=1, 2, 3 for $\{HCO_3^-, pH, pCO_2\}$, respectively, and j=1, 2, . . . , $T_k$. $T_k$ does not necessarily have to be equal; however, in some embodiments, it is assumed that $T_1=T_2=T_3=T_f$, which is patient-specific treatment duration. Each residual may be weighted with a scaling factor $\omega_1=1$ or $\omega_2=10$ as well as variance in the observation in order to weigh the relative importance of the measurements. The variances $\sigma_1^2$, $\sigma_2^2$ and $\sigma_3^2$ are estimated for each patient-specific data. An iterative approach may be employed until the convergence or termination criteria is met. Nelder-Mead optimization may be used in MATLAB® to minimize the above least-square cost function.

The model simulation results may be compared with patient-specific data for validation. Illustrative and non-limiting patient-specific data may be or may include data obtained from Sargent et al., "Acid-base homeostasis during hemodialysis: New insights into the mystery of bicarbonate disappearance during treatment," Seminars in Dialysis, pp. 1-11 (2018) and/or "Changing dialysate composition to optimize acid-base therapy. Seminars in Dialysis, Vol. 32:248-254 (2019) ("Sargent"), and/or Morel et al., "A comparison of bicarbonate kinetics and acid-base status in high flux hemodialysis and online post-dilution hemodiafiltration," International Journal of Artificial Organs, 35(4), pp. 288-300 (2012) ("Morel"). For example, patient-specific data for HD patients from Sargent and Morel were obtained for example, with patient information including age, height, post-HD weight, and dry weight.

The four model parameters $\Theta = (P_{H^+}, P_{CO_2}, \gamma_{H^+}, D_{CO_2})$ were adapted from the model calibration phase to compare the performance of the dialysis patient model with respect to each patient-specific data. The calibrated model was employed to characterize intradialytic acid-base dynamics, and to investigate the systemic effects of intradialytic correction of me.

From the data obtained from Sargent, 14 HD patients (8 female, age 67.1±14.2) were studied receiving standard bicarbonate HD, where the treatment duration was 209±5.8 min, dialysate $HCO_3^-$ concentration was 32 mmol/L, blood and dialysate flow rates were 400 ml/min and 500 ml/min, respectively, and the ultrafiltration rate was 8.6±2.9 ml/min. Similarly, the Morel data include 6 anuric patients with pre- and post-HD/HDF acid-base status. Of the 6 patients, 2 patients had detailed temporal dynamics (1 female/1 male, 37.5±26.2) receiving bicarbonate HD, where the treatment duration was 240 min, the dialysate $HCO_3^-$ concentration was 38 mmol/L, blood and dialysate flow rates were 350 ml/min and 500 ml/min, respectively.

In both studies, patients had functioning arteriovenous fistula. In the Sargent study, a Dialog+ HD system (B. Braun Avitum AG, Germany) with poly-nephron dialyzer (surface area of 1.5-1.9 m$^2$) was used, and in the Morel study, a 5008 dialysis machine (FMC AG, Germany) with poly-sulfone dialyzer FX 80 (surface area of 1.8 m$^2$) was used.

For example, in one validation study, the intradialytic acid-base model was parameterized to calculate the intra-dialytic pattern of serum $HCO_3^-$ in 16 anuric patients (9 females; age 67±12 years patient cohort derived from Sargent and Morel (14 patients from Sargent; 2 patients from Morel) receiving standard bicarbonate HD, where the treatment duration was 213±11 min, $dHCO_3^-$ concentration was 32.8±2.1 mmol/L, blood and dialysate flow rates were 375±35 ml/min and 500 ml/min, respectively, and ultrafiltration rate was 8.5±2.9 ml/min. The acid-base status may include a pre-HD pH of 7.39±0.04, a post-HD pH of 7.51±0.04, a pre-HD $HCO_3^-$ of 21.6±2.7 mmol/L, a post-HD $HCO_3^-$ of 27.4±1.4 mmol/L, a pre-HD $pCO_2$ of 36.9±3.1 mmHg, and a post-HD $pCO_2$ of 35.7±2.7 mmHg.

Figure 12:
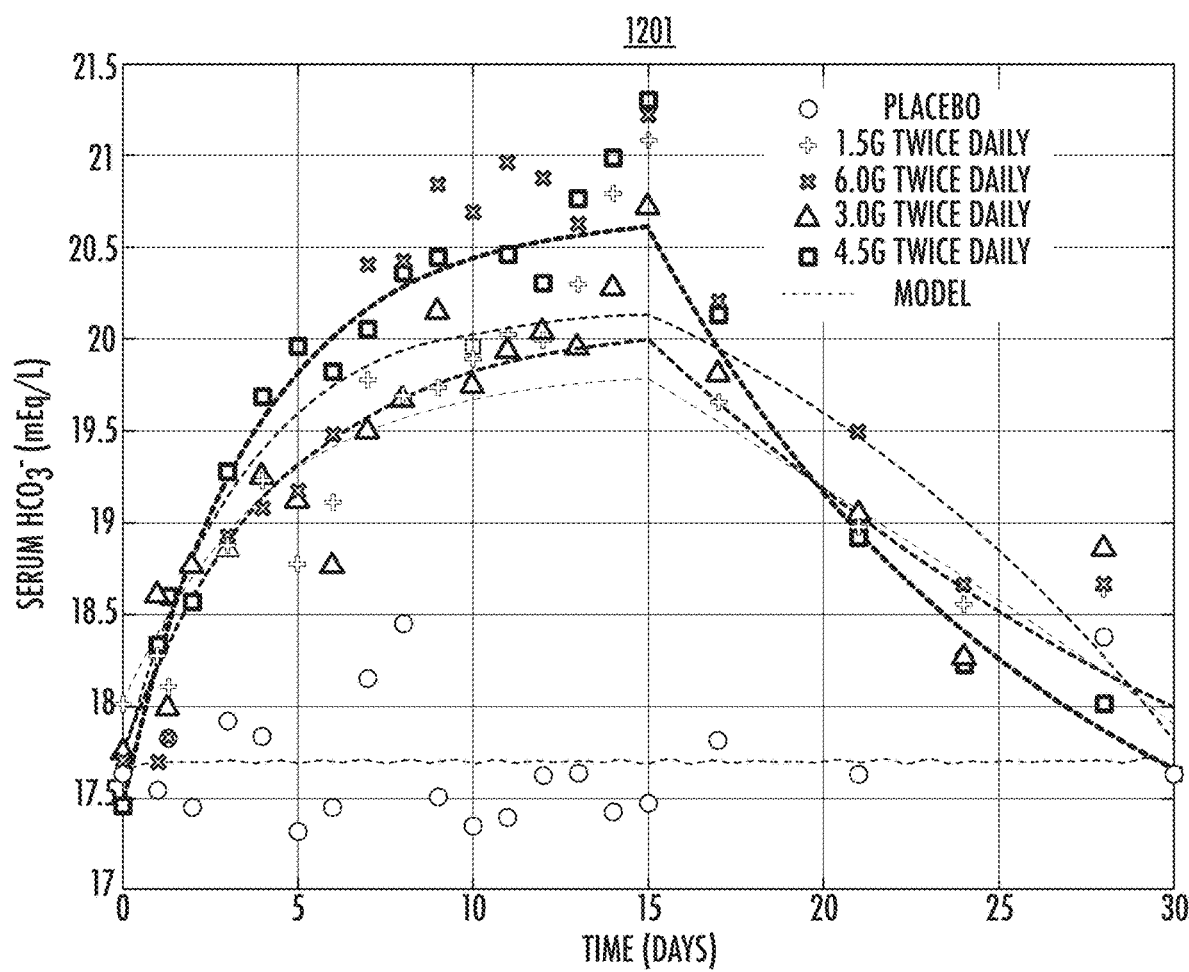
FIG. 12 illustrates a graph of acid-base information.

FIG. 12 depicts graph 1201 of correction of acidosis for various serum $HCO_3^-$ regimens (based on data adopted from Bushinsky). In general, FIG. 12 depicts an application of an acid-base model according to some embodiments, for example, application of an acid-base model to acid-binder (for example, TRC101) treatment regimens (model results shown in dashed lines corresponding to data points).

Figure 13:
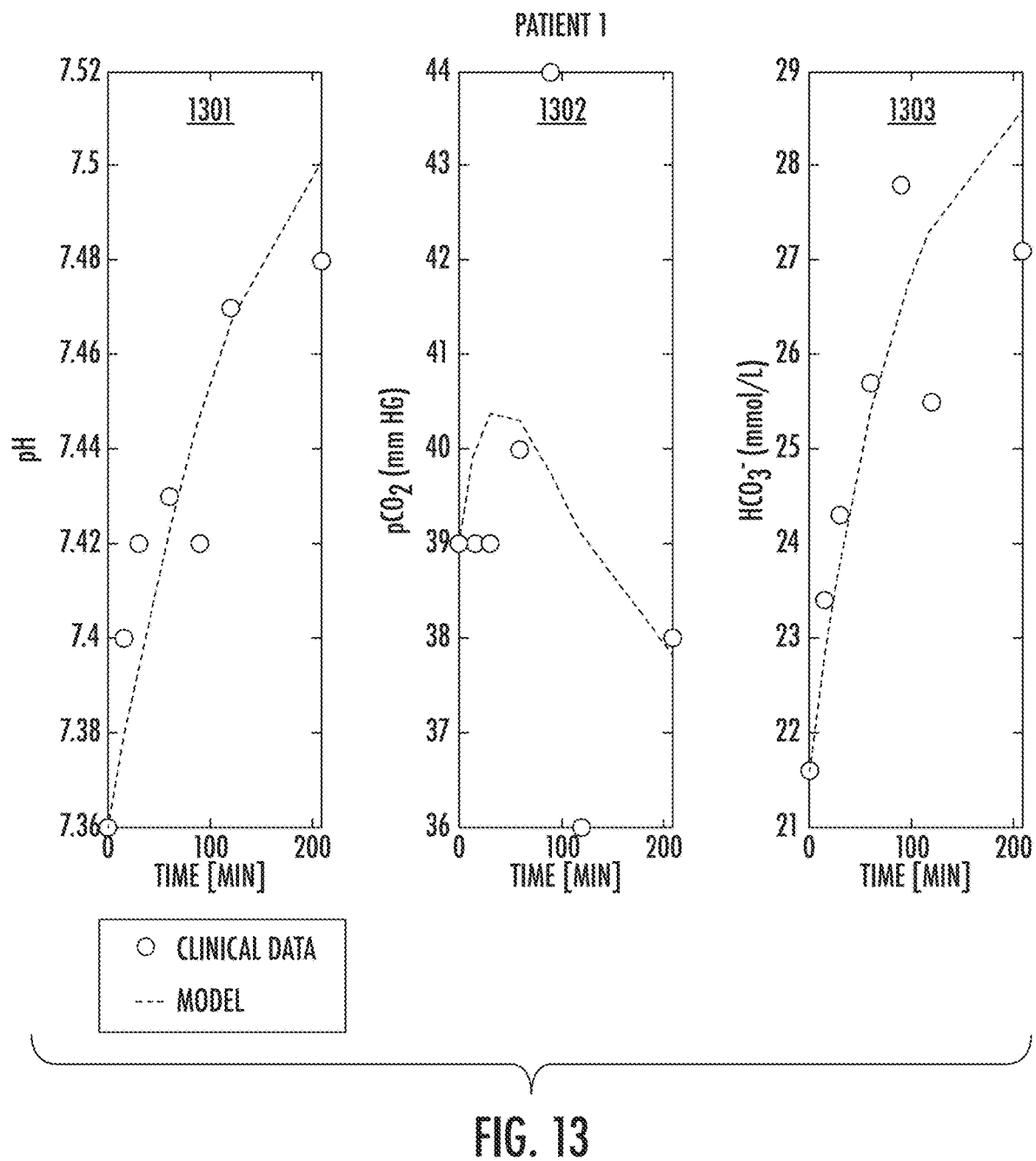
Figure 14:
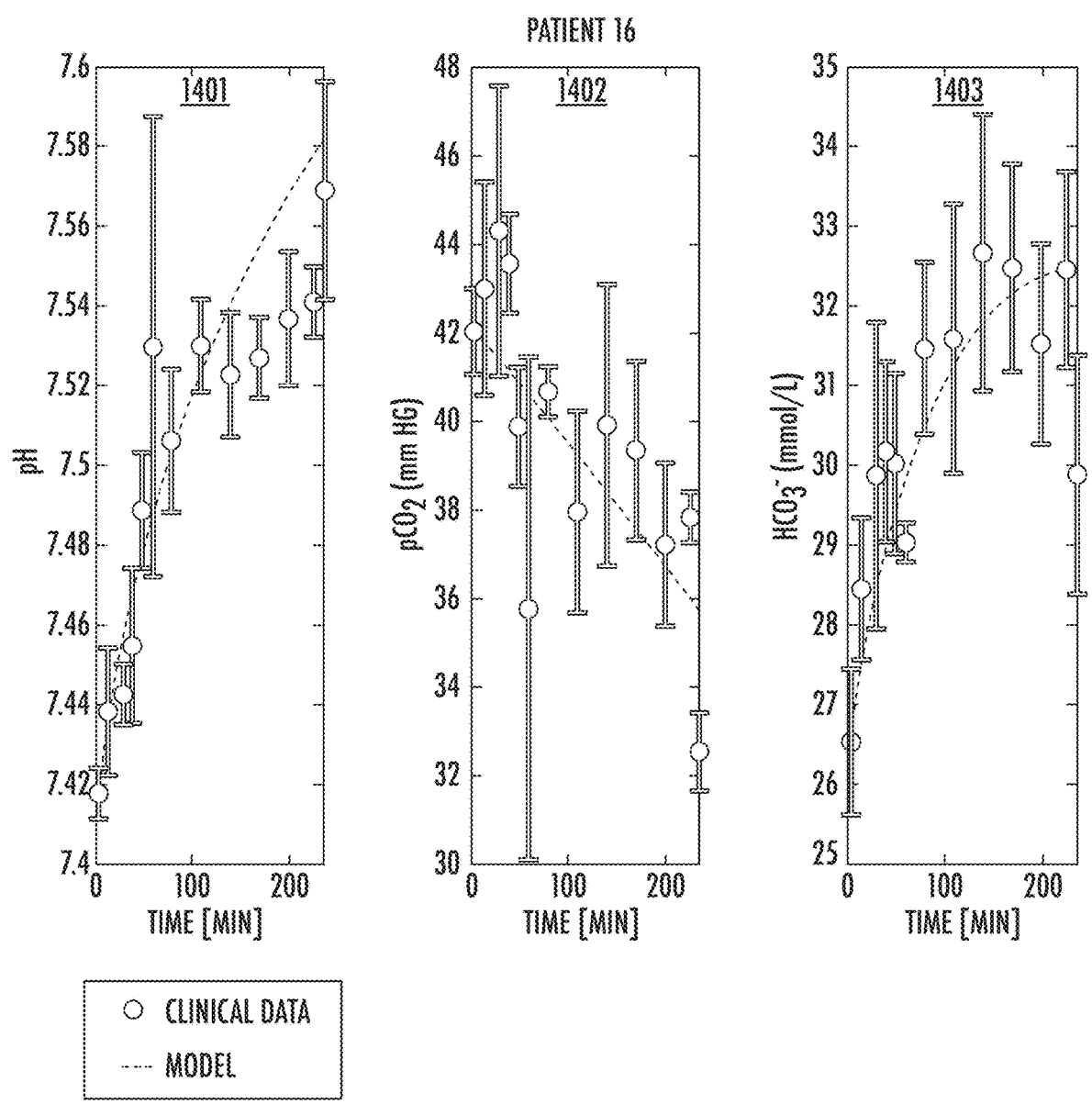

FIGS. 13-23 illustrate intradialytic acid-base model validation information. As shown in graphs 1301-1303 of FIG. 13 for patient 1 and graphs 1401-1403 of FIG. 14 for patient 16, model predictions (dashed line) accurately predict clinical observations of intradialytic serum $HCO_3^-$, $pCO_2$, and pH. In addition, empirically calculated buffer capacity may linearly align with those obtained from the values predicted by the intradialytic acid-base models. Referring to FIGS. 13 and 14, metabolic acidosis is generally observed in patients (PTS) with end-stage kidney disease. It can result in increased protein and bone catabolism and impaired cardiac contractility. In hemodialysis (HD) patients, the intradialytic transfer of HCO3 from the dialysate (dHCO3) into the patient is required to correct metabolic acidosis. Some embodiments may include dynamic acid-base models of physiologic regulation of the HCO3/CO2 buffering system to investigate the systemic effects of intradialytic correction of metabolic acidosis.

Figure 15:
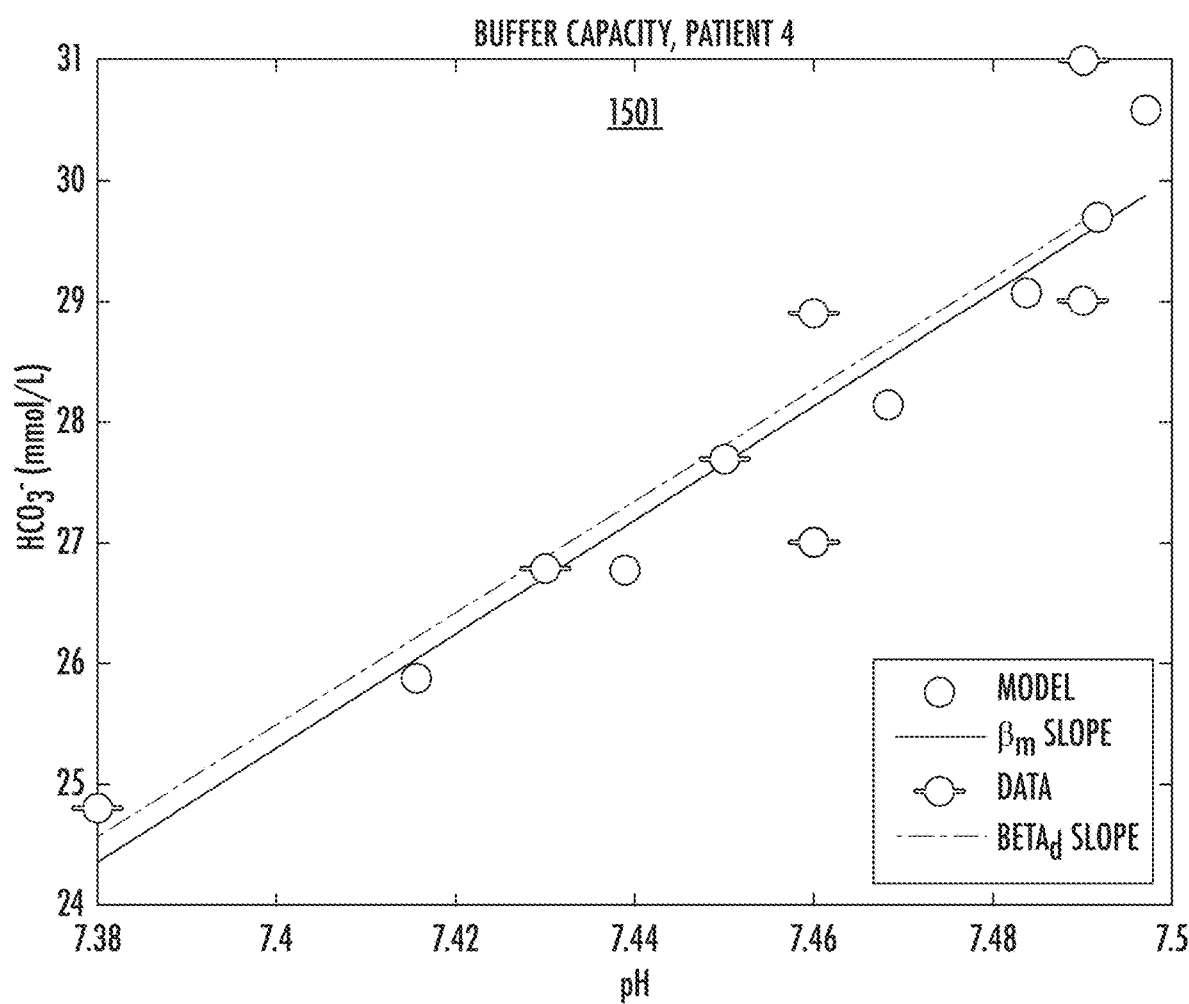
Figure 16:
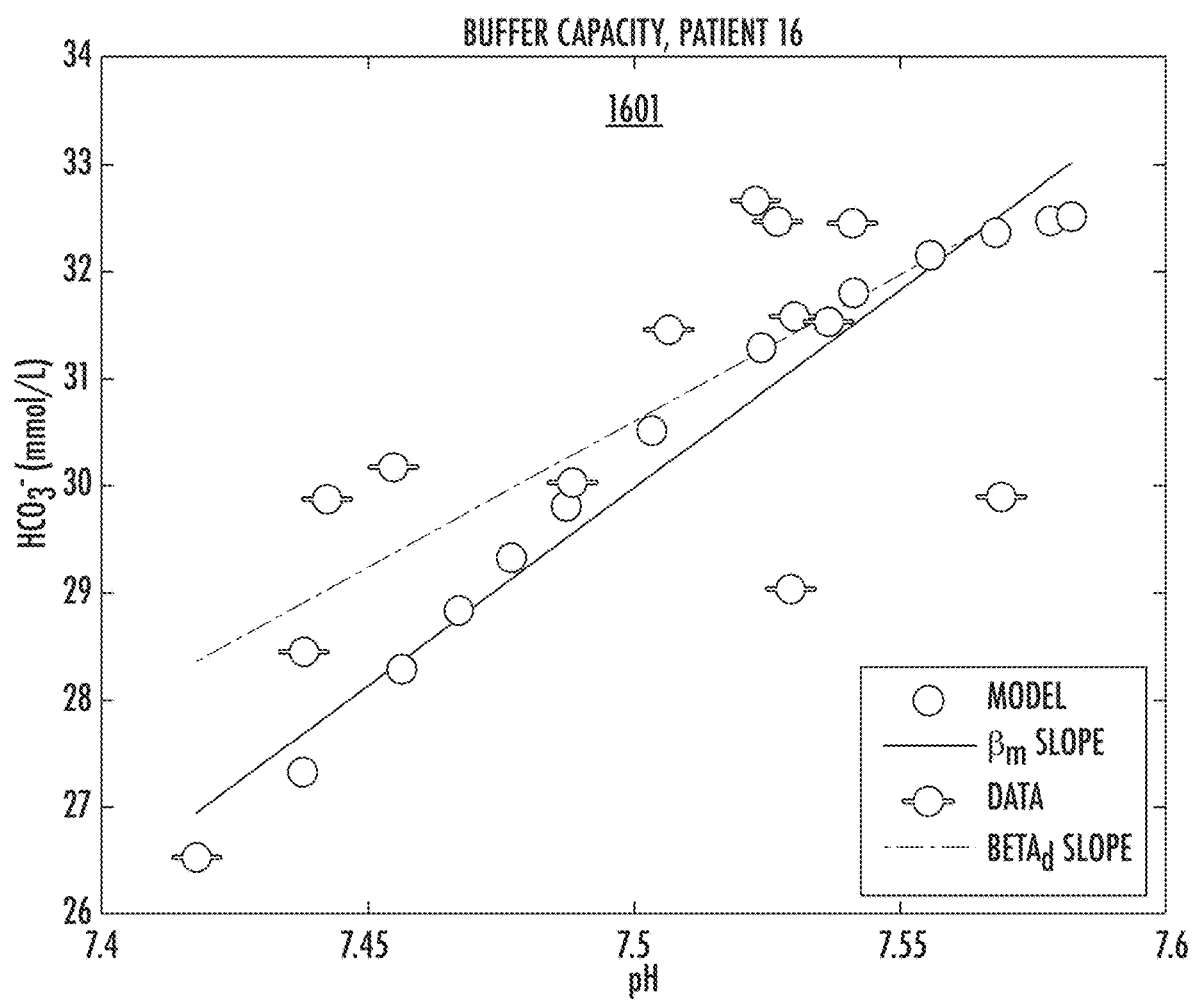
Figure 17:
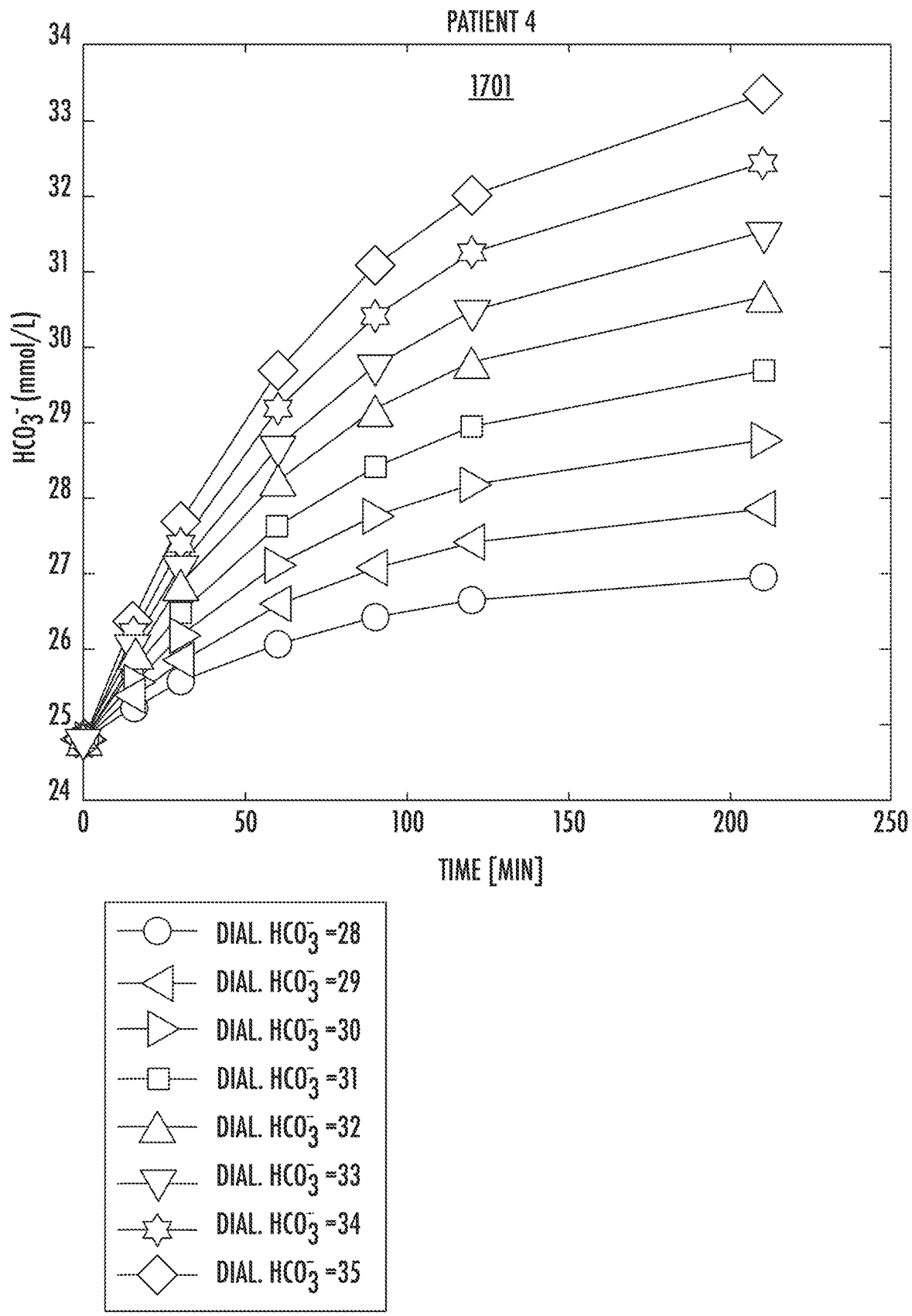
Figure 18:
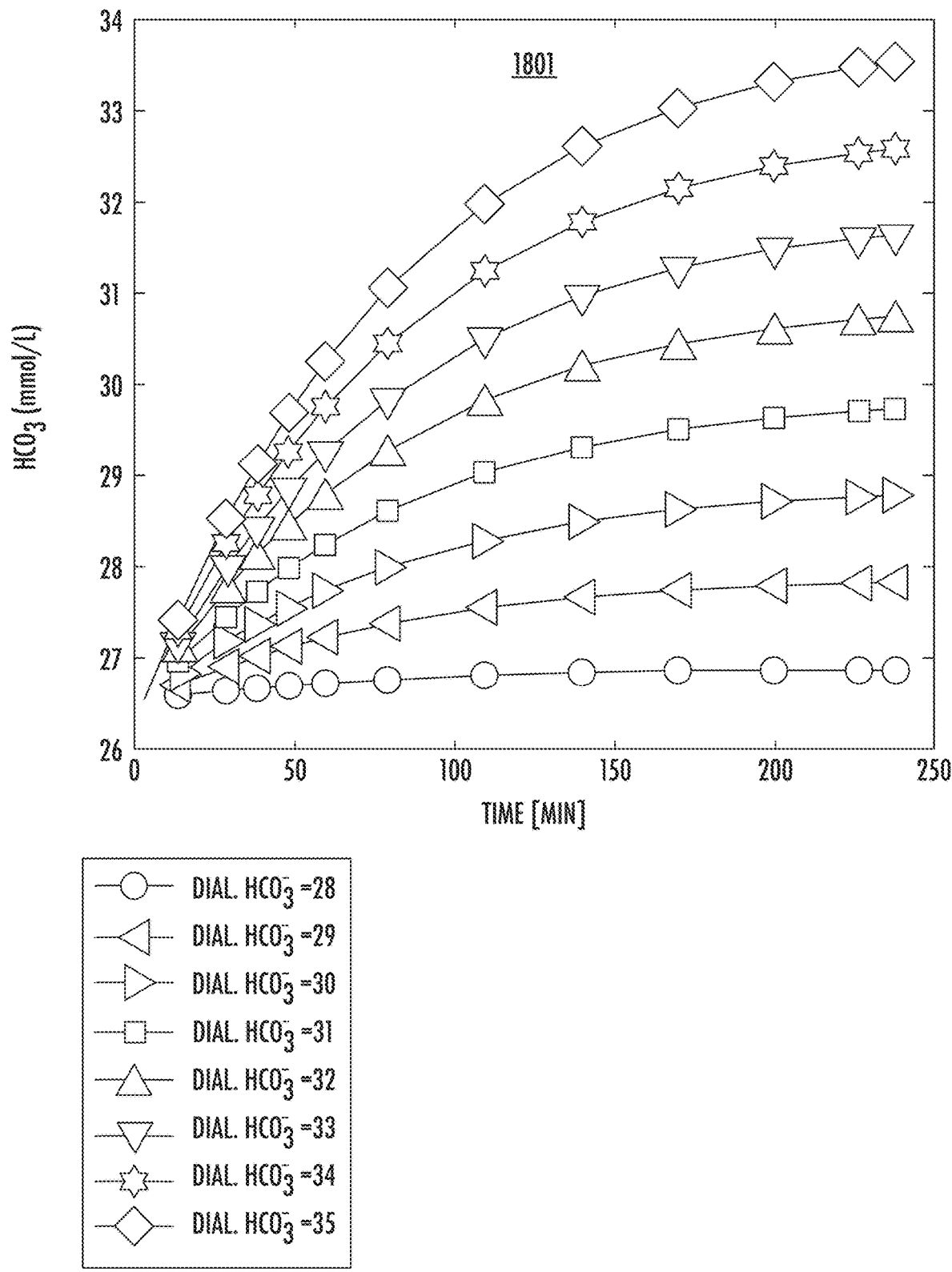

Graph 1501 of FIG. 15 illustrates intradialytic acid-base model validation information of $HCO_3^-$ versus pH for dialysate $HCO_3^-$ of 32 mmol/L for patient 4. Graph 1601 of FIG. 16 illustrates intradialytic acid-base model validation information of $HCO_3^-$ versus pH for dialysate $HCO_3^-$ of 38 mmol/L for patient 16. Graph 1701 of FIG. 17 depicts the effect of dialysate $HCO_3^-$ on intradialytic $HCO_3^-$ for patient 4. Graph 1801 of FIG. 18 depicts the effect of dialysate $HCO_3^-$ on intradialytic $HCO_3^-$ for patient 16.

Figure 19:
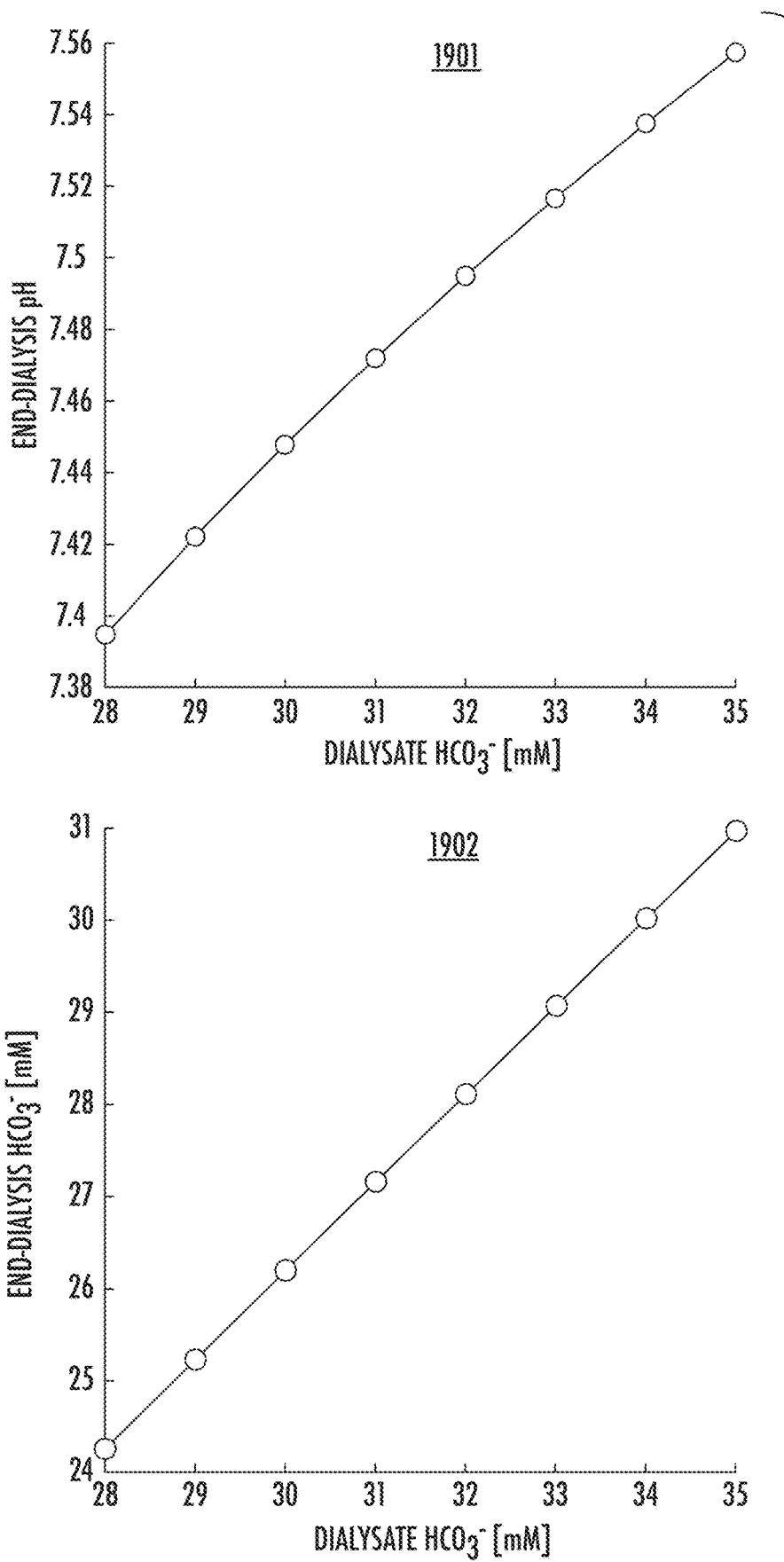

Referring to FIG. 19, graph 1901 depicts the effect of dialysate $HCO_3^-$ on end-dialysis pH for patient 1 and graph 1902 depicts the effect of dialysate $HCO_3^-$ on end dialysis $HCO_3^-$ for patient 1. Referring to FIG. 20, graph 2001 depicts the effect of UFV on end-dialysis pH for patient 1 and graph and graph 2002 depicts the effect of UFV on end dialysis $HCO_3^-$ for patient 1.

Figure 21:
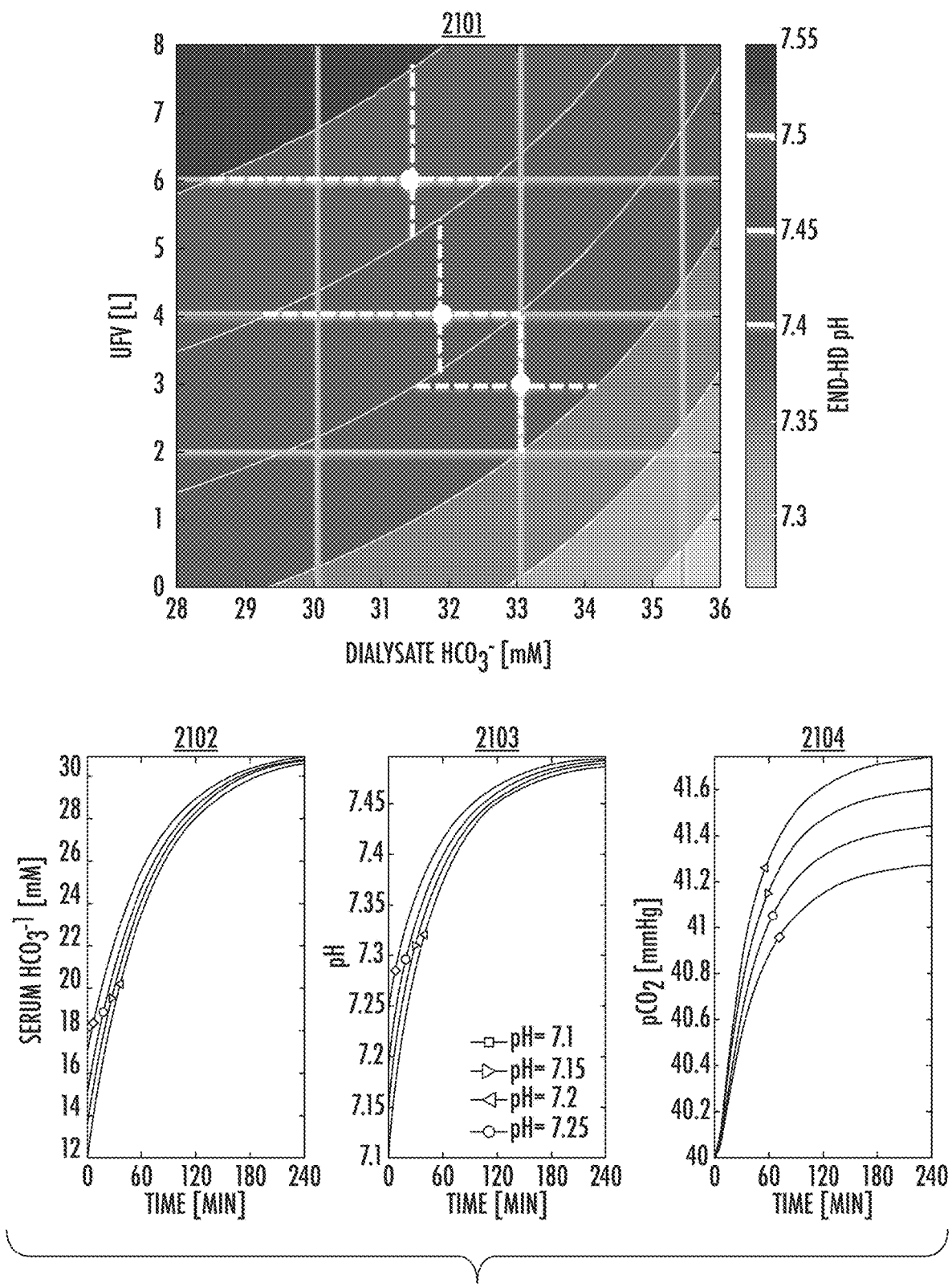
Figure 22:
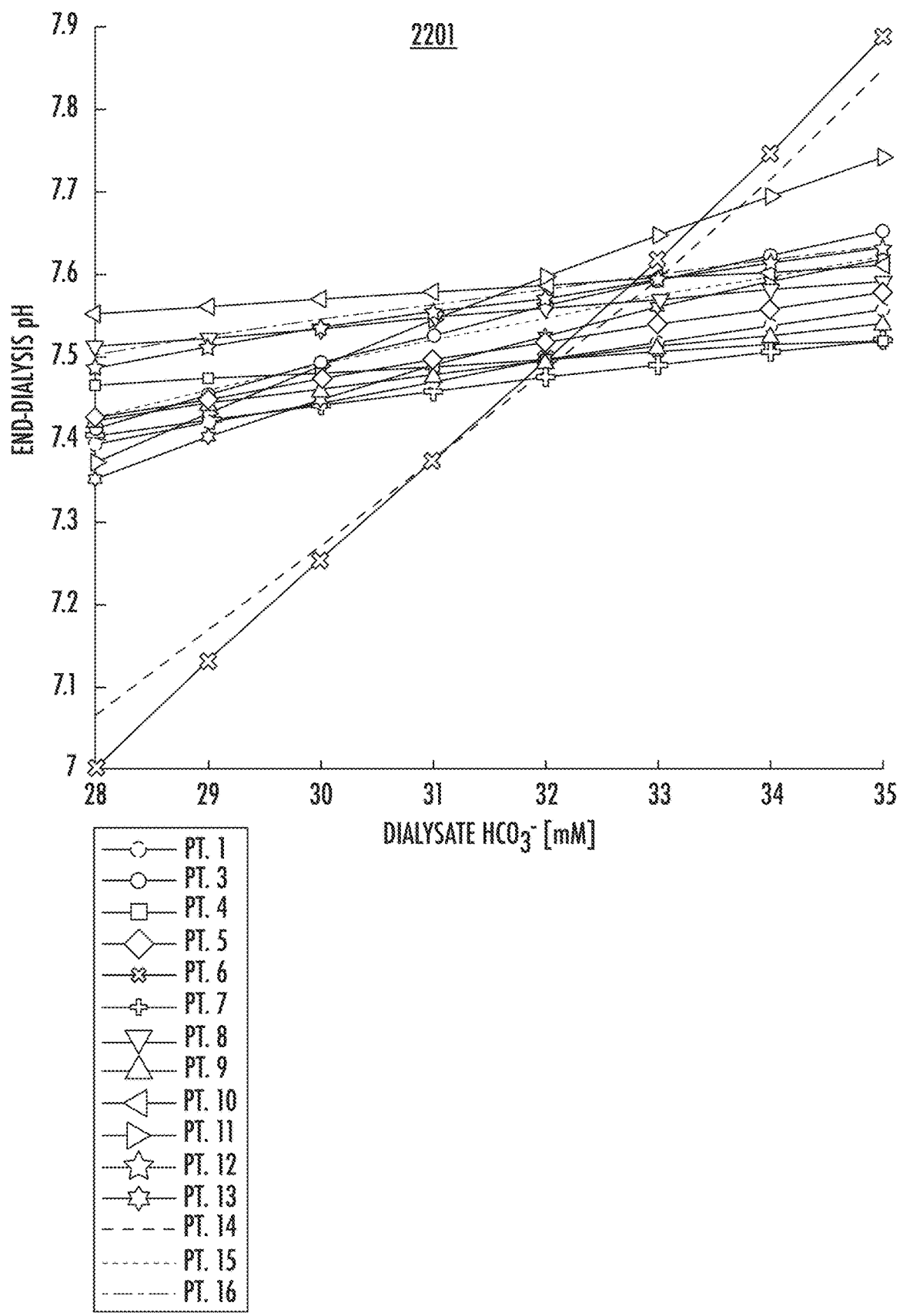
Figure 23:
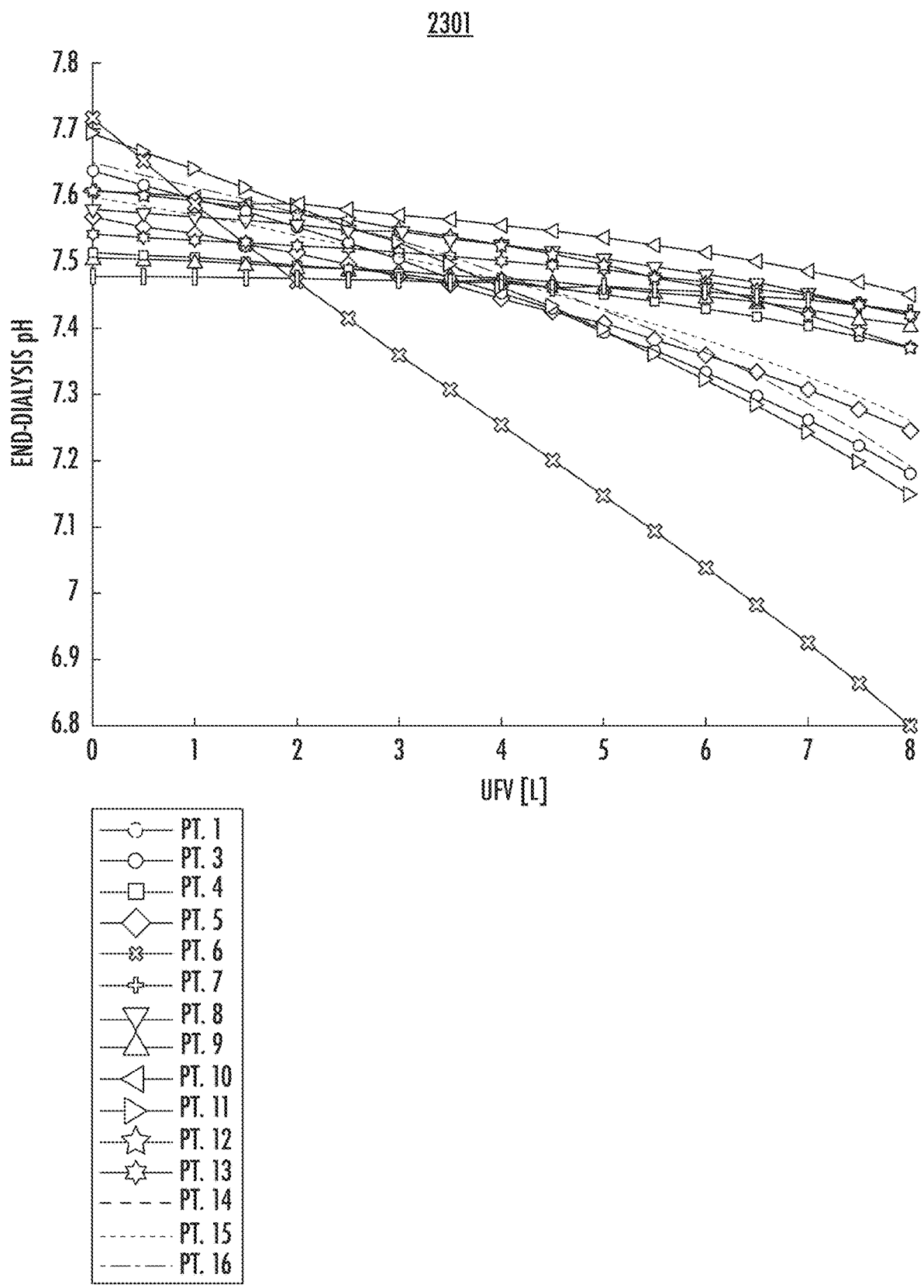
Figure 24:
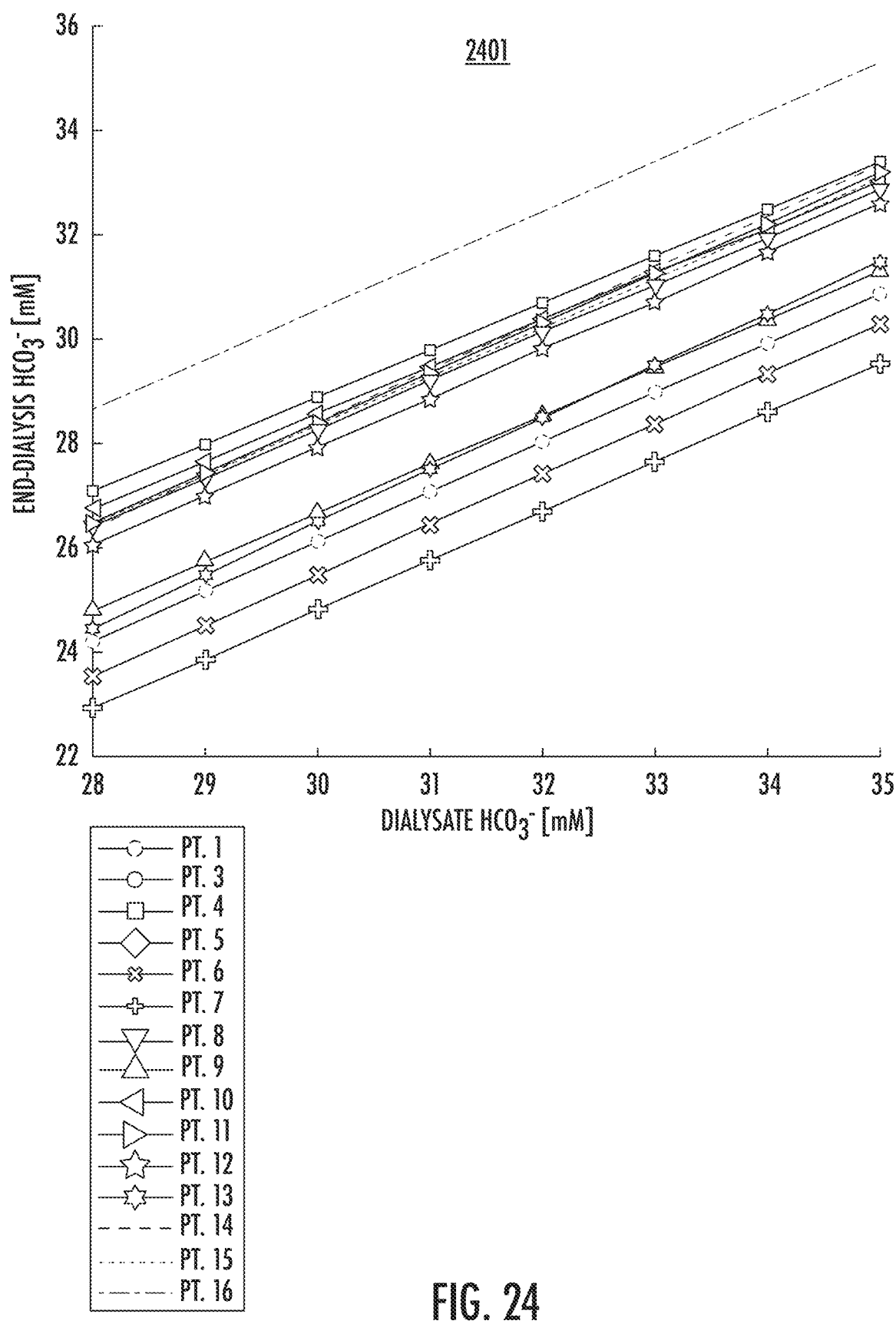
Figure 25:
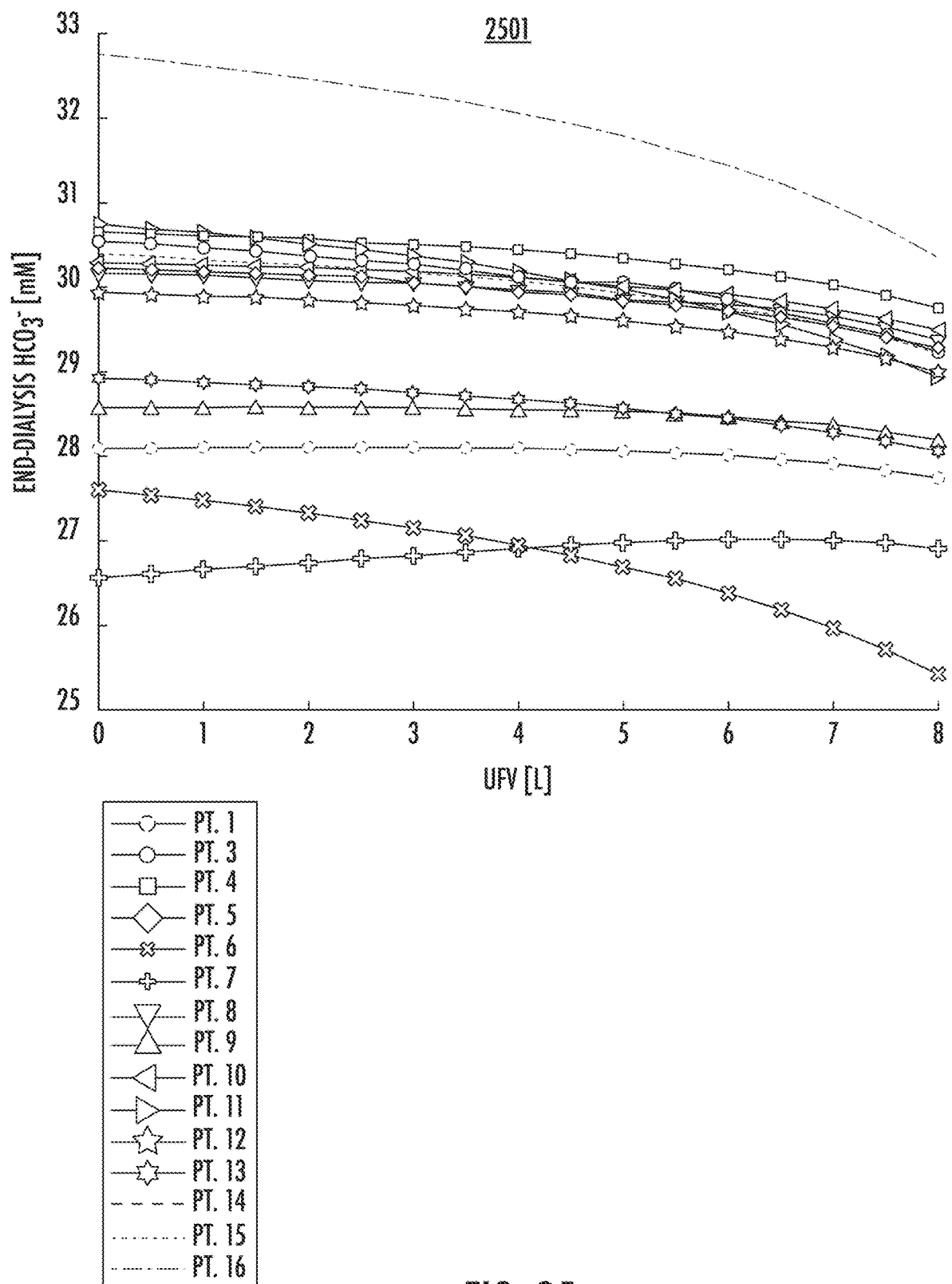

Referring to FIG. 21, graphs 2101-2104 depict acid-base dose responses for patient 1, showing a combined effect of UVF and dialysate $HCO_3^-$ on post-HD pH (graph 2101) and the effect of pre-HD on post HD acid base status (graphs 2102-2104).

The HD dose-response curve computed based on acid-base models according to some embodiments indicates that, for some patients, the slope might be steep while for others it may be more gradual (see, for example, FIGS. 22-25). This implies that for some patients, the prescription of more $dHCO_3^-$ may not necessarily increase the pH level. In 12 patients, $dHCO_3^-$ levels ranging from 28-35 mM yield increases in post-HD pH by from 0.6%-2.6% (28 mM) to 1.9%-4.8% (35 mM) percent change. In 2 patients, a $dHCO_3^-$ below 32 mM results in a decrease in post-HD pH level to a value below the patients' pre-HD pH. Similar pH dynamics can be observed in 2 patients with $dHCO_3^-$ below 29 mM. Graph 1901 of FIG. 19 depicts the absolute pH values for all patients in the validation population. Similar HD dose-response curves for dialysate and ultrafiltration volume (UFV) with post-HD $HCO_3^-$ are shown in graphs 2301, 2401, and 2501 of FIGS. 23-25. More specifically, FIGS. 22-25 depict HD dose-response curves showing achieved post-HD pH (1901) and end-dialysis $HCO_3^-$ (2101) as a function of hypothetically prescribed $dHCO_3^-$ concentrations for each patient given observed pre-HD pH and $HCO_3^-$ levels, and (2501) shows end-dialysis $HCO_3^-$ as a function of ultrafiltration volume (at $dHCO_3^-$ of 32 mM). Accordingly, in some embodiments, acid-base models may be used (for example, via acid-base homeostasis logic 130) to generate patient-specific acid-base response curves.

The results depicted in FIGS. 22-25 show that a uniform $dHCO_3^-$ concentration can result in variable end-HD pH and $HCO_3^-$. Moreover, UFV may have a significant impact on the end-dialysis pH value and should be considered when prescribing the $dHCO_3^-$ (see, for example, FIG. 22).

Figure 26:
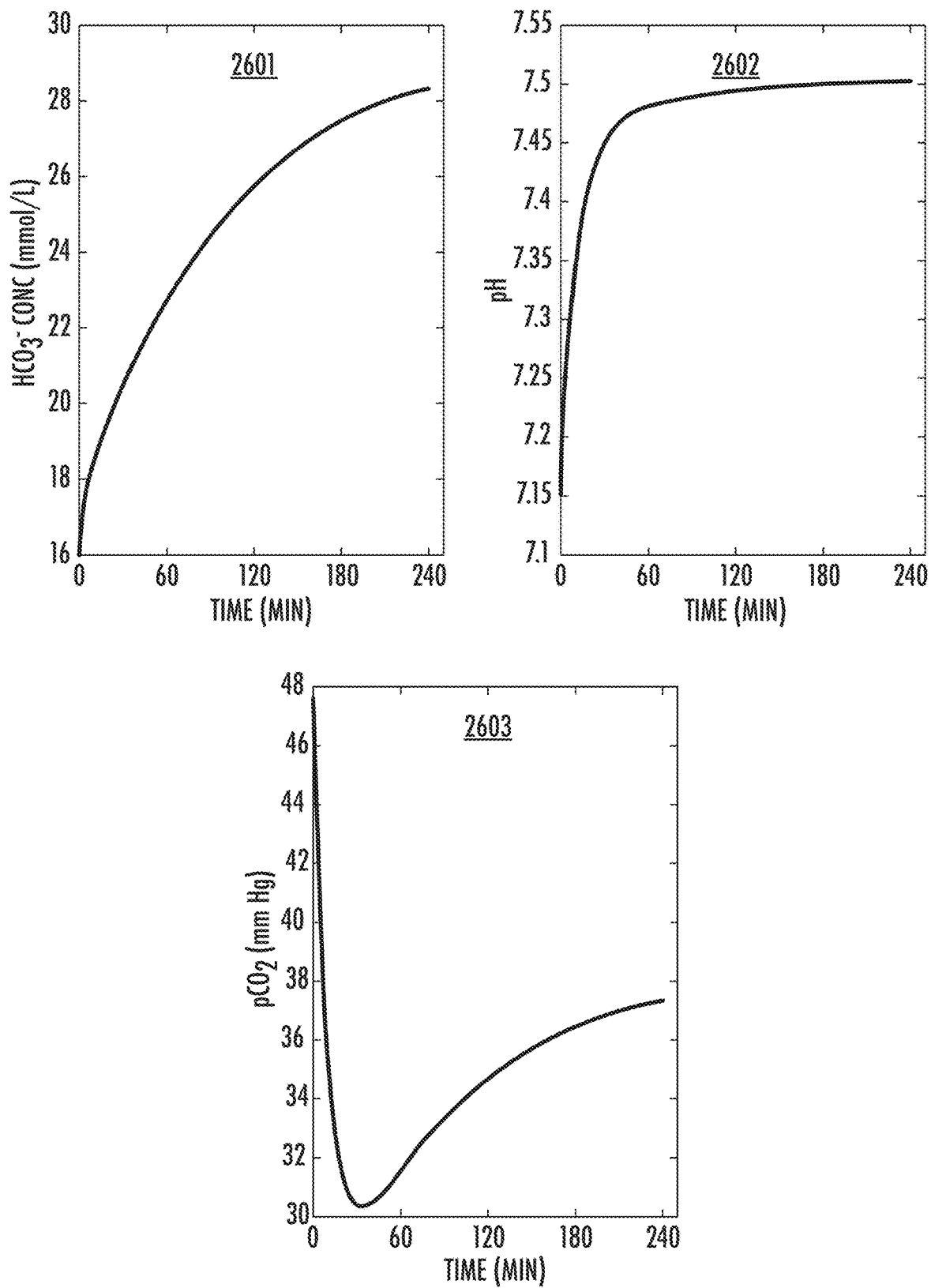

FIG. 26 depicts graphs 2601-2603 for correction of metabolic acidosis for an example patient in which the patient is a male weighing about 72 kg, dialyzed with an Optiflux F180NR dialyzer with a blood flow rate of 300 mL/min, a dialysate flow rate of 800 mL/min, a dialysate $HCO_3^-$ of 32 mM, an EC Volume of 16 L, and a UFV of 2.4 L. FIG. 26 demonstrates the ability of acid-base models according to some embodiments to provide acid-base information, treatment recommendations, predicted patient information, and/or the like that may be used to determine effective treatment regimens and therapeutic courses of treatment for patients with acid-base disorders.

Figure 27:
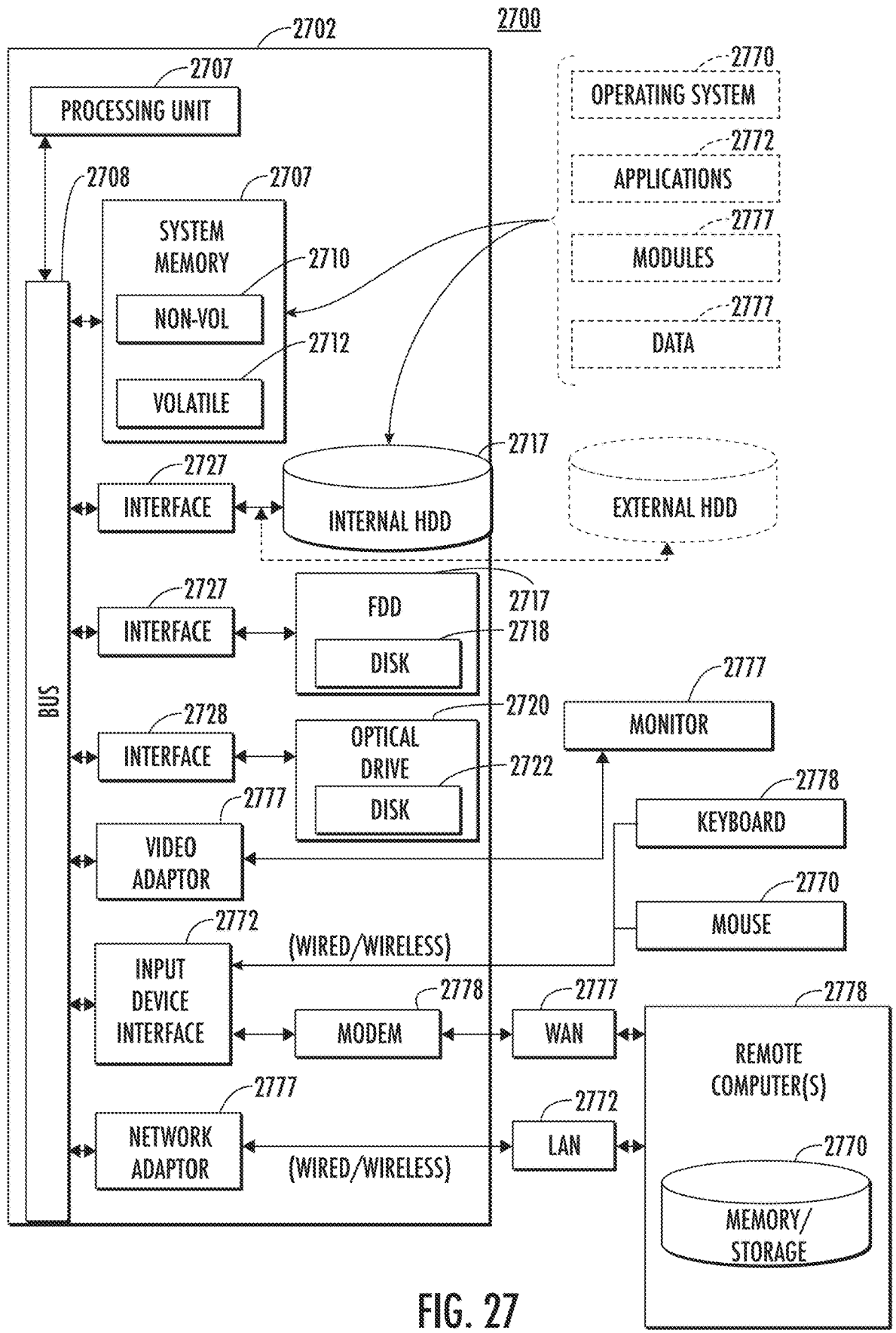
FIG. 27 illustrates an embodiment of a computing architecture in accordance with the present disclosure.

FIG. 27 illustrates an embodiment of an exemplary computing architecture 2700 suitable for implementing various embodiments as previously described. In various embodiments, the computing architecture 2700 may comprise or be implemented as part of an electronic device. In some embodiments, the computing architecture 2700 may be representative, for example, of computing device 110. The embodiments are not limited in this context.

As used in this application, the terms "system" and "component" and "module" are intended to refer to a computer-related entity, either hardware, a combination of hardware and software, software, or software in execution, examples of which are provided by the exemplary computing architecture 2700. For example, a component can be, but is not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server can be a component. One or more components can reside within a process and/or thread of execution, and a component can be localized on one computer and/or distributed between two or more computers.

Further, components may be communicatively coupled to each other by various types of communications media to coordinate operations. The coordination may involve the uni-directional or bi-directional exchange of information. For instance, the components may communicate information in the form of signals communicated over the communications media. The information can be implemented as signals allocated to various signal lines. In such allocations, each message is a signal. Further embodiments, however, may alternatively employ data messages. Such data messages may be sent across various connections. Exemplary connections include parallel interfaces, serial interfaces, and bus interfaces.

The computing architecture 2700 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, are not limited to implementation by the computing architecture 2700.

As shown in FIG. 27, the computing architecture 2700 comprises a processing unit 2704, a system memory 2706 and a system bus 2708. The processing unit 2704 may be a commercially available processor and may include dual microprocessors, multi-core processors, and other multi-processor architectures.

The system bus 2708 provides an interface for system components including, but not limited to, the system memory 2706 to the processing unit 2704. The system bus 2708 can be any of several types of bus structure that may further interconnect to a memory bus (with or without a memory controller), a peripheral bus, and a local bus using any of a variety of commercially available bus architectures. Interface adapters may connect to the system bus 2708 via a slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The system memory 2706 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory, polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (for example, USB memory, solid state drives (SSD) and any other type of storage media suitable for storing information. In the illustrated embodiment shown in FIG. 27, the system memory 2706 can include non-volatile memory 2710 and/or volatile memory 2712. A basic input/output system (BIOS) can be stored in the non-volatile memory 2710. The computer 2702 may include various types of computer-readable storage media in the form of one or more lower speed memory units, including an internal (or external) hard disk drive (HDD) 2714, a magnetic floppy disk drive (FDD) 2716 to read from or write to a removable magnetic disk 2711, and an optical disk drive 2720 to read from or write to a removable optical disk 2722 (for example, a CD-ROM or DVD). The HDD 2714, FDD 2716 and optical disk drive 2720 can be connected to the system bus 2708 by a HDD interface 2724, an FDD interface 2726 and an optical drive interface 2728, respectively. The HDD interface 2724 for external drive implementations can include at least one or both of Universal Serial Bus (USB) and IEEE 1114 interface technologies.

The drives and associated computer-readable media provide volatile and/or nonvolatile storage of data, data structures, computer-executable instructions, and so forth. For example, a number of program modules can be stored in the drives and memory units 2710, 2712, including an operating system 2730, one or more application programs 2732, other program modules 2734, and program data 2736. In one embodiment, the one or more application programs 2732, other program modules 2734, and program data 2736 can include, for example, the various applications and/or components of computing device 110.

A user can enter commands and information into the computer 2702 through one or more wired/wireless input devices, for example, a keyboard 2738 and a pointing device, such as a mouse 2740. These and other input devices are often connected to the processing unit 2704 through an input device interface 2742 that is coupled to the system bus 2708, but can be connected by other interfaces.

A monitor 2744 or other type of display device is also connected to the system bus 2708 via an interface, such as a video adaptor 2746. The monitor 2744 may be internal or external to the computer 2702. In addition to the monitor 2744, a computer typically includes other peripheral output devices, such as speakers, printers, and so forth.

The computer 2702 may operate in a networked environment using logical connections via wired and/or wireless communications to one or more remote computers, such as a remote computer 2748. The remote computer 2748 can be a workstation, a server computer, a router, a personal computer, portable computer, microprocessor-based entertainment appliance, a peer device or other common network node, and typically includes many or all of the elements described relative to the computer 2702, although, for purposes of brevity, only a memory/storage device 2750 is illustrated. The logical connections depicted include wired/wireless connectivity to a local area network (LAN) 2752 and/or larger networks, for example, a wide area network (WAN) 2754. Such LAN and WAN networking environments are commonplace in offices and companies, and facilitate enterprise-wide computer networks, such as intranets, all of which may connect to a global communications network, for example, the Internet.

The computer 2702 is operable to communicate with wired and wireless devices or entities using the IEEE 802 family of standards, such as wireless devices operatively disposed in wireless communication (for example, IEEE 802.16 over-the-air modulation techniques). This includes at least Wi-Fi (or Wireless Fidelity), WiMax, and Bluetooth™ wireless technologies, among others. Thus, the communication can be a predefined structure as with a conventional network or simply an ad hoc communication between at least two devices. Wi-Fi networks use radio technologies called IEEE 802.11x (a, b, g, n, etc.) to provide secure, reliable, fast wireless connectivity. A Wi-Fi network can be used to connect computers to each other, to the Internet, and to wire networks (which use IEEE 802.3-related media and functions).

Numerous specific details have been set forth herein to provide a thorough understanding of the embodiments. It will be understood by those skilled in the art, however, that the embodiments may be practiced without these specific details. In other instances, well-known operations, components, and circuits have not been described in detail so as not to obscure the embodiments. It can be appreciated that the specific structural and functional details disclosed herein may be representative and do not necessarily limit the scope of the embodiments.

Some embodiments may be described using the expression "coupled" and "connected" along with their derivatives. These terms are not intended as synonyms for each other. For example, some embodiments may be described using the terms "connected" and/or "coupled" to indicate that two or more elements are in direct physical or electrical contact with each other. The term "coupled," however, may also mean that two or more elements are not in direct contact with each other, but yet still co-operate or interact with each other.

Unless specifically stated otherwise, it may be appreciated that terms such as "processing," "computing," "calculating," "determining," or the like, refer to the action and/or processes of a computer or computing system, or similar electronic computing device, that manipulates and/or transforms data represented as physical quantities (for example, electronic) within the computing system's registers and/or memories into other data similarly represented as physical quantities within the computing system's memories, registers or other such information storage, transmission or display devices. The embodiments are not limited in this context.

It should be noted that the methods described herein do not have to be executed in the order described, or in any particular order. Moreover, various activities described with respect to the methods identified herein can be executed in serial or parallel fashion.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. It is to be understood that the above description has been made in an illustrative fashion, and not a restrictive one. Combinations of the above embodiments, and other embodiments not specifically described herein will be apparent to those of skill in the art upon reviewing the above description. Thus, the scope of various embodiments includes any other applications in which the above compositions, structures, and methods are used.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, an element or operation recited in the singular and proceeded with the word "a" or "an" should be understood as not excluding plural elements or operations, unless such exclusion is explicitly recited. Furthermore, references to "one embodiment" of the present disclosure are not intended to be interpreted as excluding the existence of additional embodiments that also incorporate the recited features.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A method of treating an acid-base disorder of a human patient, the method comprising:
   determining at least one treatment recommendation for the acid-base disorder for a population of virtual patients using an acid-base model configured to model the acid-base disorder via modelling serum pH regulation of a human bicarbonate ($HCO_2$)/carbon dioxide ($CO_2$) buffering system using human renal and pulmonary regulatory mechanisms to generate predicted patient information, the predicted patient information comprising a serum pH level determined by the acid-base model based on a $HCO_2$ concentration and a $CO_2$ concentration, wherein:
the $HCO_2$ concentration is determined based, at least in part, on a renal filtration rate of $HCO_2$ model parameter, and
the $CO_2$ concentration is determined based, at least in part, on a removal of CO2 through respiratory ventilation model parameter,
accessing the at least one treatment recommendation determined via the acid-base model;
diagnosing that the patient has the acid-base disorder; and
administering a treatment to the patient determined to correspond with the at least one treatment recommendation to treat the acid-base disorder, wherein the acid-base disorder is metabolic acidosis and the patient is treated with at least one of $HCO_2$ therapy or acid-binder therapy.

2. The method of treating the acid-base disorder of the patient of claim 1, wherein the physiological acid-base model is configured to receive a value of at least one operating parameter to disequilibriate one or more of $pCO_2$ and $HCO_2$ to induce the acid-base disorder for the acid-base model, the at least one operating parameter comprising at least one of an acid secretion rate parameter or a renal filtration rate parameter.

3. The method of treating the acid-base disorder of the patient of claim 2, wherein the acid-base disorder is induced by setting the acid secretion rate parameter to zero.

4. The method of treating the acid-base disorder of the patient of claim 3, wherein the acid-base disorder is renal tubular acidosis.

5. The method of treating the acid-base disorder of the patient of claim 2, wherein the acid-base disorder is induced by setting the renal filtration rate parameter to zero.

6. The method of treating the acid-base disorder of the patient of claim 5, wherein the acid-base disorder is proximal tubular acidosis.

7. The method of treating the acid-base disorder of the patient of claim 1, wherein the at least one treatment recommendation is determined to affect at least one primary parameter to treat the acid-base disorder, the primary parameter comprising a parameter correlated with treating the acid-base disorder.

8. The method of treating the acid-base disorder of the patient of claim 7, wherein the at least one primary parameter is determined via a sensitivity analysis of the predicted patient information.

9. The method of treating the acid-base disorder of the patient of claim 1, wherein the removal of $CO_2$ through respiratory ventilation model parameter is determined based, at least in part, on an effective ventilation rate $D_{CO_2} V_0$, where $V_0$ is a minute volume ventilation and $D_{CO_2}$ is a ventilation rate.

10. The method of treating the acid-base disorder of the patient of claim 9, wherein the removal of $CO_2$ through respiratory ventilation model parameter is determined based, at least in part, on the effective ventilation rate $D_{CO_2} V_0$ and a concentration of carbon dioxide $Y_{CO_2}$.

11. The method of treating the acid-base disorder of the patient of claim 1, wherein the bicarbonate concentration is determined using a physiological acid-base model equation comprising the renal filtration rate of $HCO_2$ model parameter, a $HCO_2$ therapy model parameter, an acid secretion rate model parameter, a concentration of carbon dioxide model parameter, a hydration reaction rate model parameter, a de-hydration reaction rate model parameter, a concentration of free hydrogen protons model parameter, and a concentration of carbon dioxide model parameter.

12. The method of treating the acid-base disorder of the patient of claim 1, the carbon dioxide concentration determined using a physiological acid-base model equation comprising the removal of $CO_2$ through respiratory ventilation model parameter, a body or cellular production of $CO_2$ model parameter, a hydration reaction rate model parameter, a de-hydration reaction rate model parameter, a concentration of free hydrogen protons model parameter, and a concentration of bicarbonate model parameter.

13. The method of treating the acid-base disorder of the patient of claim 1, wherein the bicarbonate concentration is determined via the following:

$$\frac{dY_{HCO_3^-}}{dt} = J_{HCO_3^-} + \phi_{CO_2} Y_{CO_2} - D_{HCO_3^-} Y_{HCO_3^-} - K_{H^+,HCO_3^-} Y_{H^+} Y_{HCO_3^-} + K_{CO_2} Y_{CO_2}.$$

where $Y_{HCO_3^-}$ is a concentration of bicarbonate, $J_{HCO_3^-}$ represents $HCO_3^-$ therapy and/or supplementation, $\phi_{CO_2}$ is an acid secretion rate, is a concentration of carbon dioxide, $D_{HCO_3^-}$ is a renal filtration rate of $HCO_3^-$, $K_{H^+,HCO_3^-}$ is a hydration reaction rate, $K_{CO_2}$ is a de-hydration reaction rate, $Y_{H^+}$ is a concentration of free hydrogen protons, and $Y_{CO_2}$ is a concentration of carbon dioxide.

14. The method of treating the acid-base disorder of the patient of claim 1, wherein the carbon dioxide concentration is determined via the following:

$$\frac{dY_{CO_2}}{dt} = P_{CO_2} - D_{CO_2} V_0 Y_{CO_2} + K_{H^+,HCO_3^-} Y_{H^+} Y_{HCO_3^-} - K_{CO_2} Y_{CO_2},$$

where is a concentration of carbon dioxide, $P_{CO_2}$ is a body or cellular production of $CO_2$, $D_{CO_2} V_0$ is an effective ventilation rate, $Y_{CO_2}$ is a concentration of carbon dioxide, $K_{H^+,HCO_3^-}$ is a hydration reaction rate, $K_{CO_2}$ is a de-hydration reaction rate, $Y_{H^+}$ is a concentration of free hydrogen protons, and $Y_{HCO_3^-}$ is a concentration of bicarbonate.

15. The method of treating the acid-base disorder of the patient of claim 1, wherein the free hydrogen ions concentration is determined via the following:

$$\frac{dY_{H^+}}{dt} = P_{H^+} - \gamma_{H^+} Y_{H^+} - K_{H^+,HCO_3^-} Y_{H^+} Y_{HCO_3^-} + K_{CO_2} Y_{CO_2},$$

where $Y_{H^+}$ is a concentration of free hydrogen protons, $P_{H^+}$ is a cellular production of $H^+$, $\gamma_{H^+}$ is H loss, $K_{H^+,HCO_3^-}$ is a hydration reaction rate, $K_{CO_2}$ is a de-hydration reaction rate, and $Y_{CO_2}$ is a concentration of carbon dioxide.

* * * * *

UNITED STATES PATENT AND TRADEMARK OFFICE
CERTIFICATE OF CORRECTION

PATENT NO. : 12,230,403 B2
APPLICATION NO. : 16/815366
DATED : February 18, 2025
INVENTOR(S) : Alhaji Cherif et al.

It is certified that error appears in the above-identified patent and that said Letters Patent is hereby corrected as shown below:

In the Claims

Column 32, Claim 1, Line 64, please remove "(HCO2)" and insert -- $(HCO_3^-)$ --.

Column 33, Claim 1, Line 2, please remove "HCO2" and insert -- $HCO_3^-$ --.

Column 33, Claim 1, Line 4, please remove "HCO2" and insert -- $HCO_3^-$ --.

Column 33, Claim 1, Line 5, please remove "HCO2" and insert -- $HCO_3^-$ --.

Column 33, Claim 1, Line 8, please remove "CO2" and insert -- $CO_2$ --.

Column 33, Claim 1, Line 17, please remove "HCO2" and insert -- $HCO_3^-$ --.

Column 33, Claim 2, Line 23, please remove "HCO2" and insert -- $HCO_3^-$ --.

Column 33, Claim 11, Line 63, please remove "HCO2" and insert -- $HCO_3^-$ --.

Column 34, Claim 11, Line 1, please remove "HCO2" and insert -- $HCO_3^-$ --.

Signed and Sealed this
Third Day of June, 2025

Coke Morgan Stewart
*Acting Director of the United States Patent and Trademark Office*